US011904289B2

(12) United States Patent
Eshima et al.

(10) Patent No.: US 11,904,289 B2
(45) Date of Patent: *Feb. 20, 2024

(54) SYSTEMS, METHODS AND DEVICES FOR PRODUCING, MANUFACTURING AND CONTROL OF RADIOPHARMACEUTICALS

(71) Applicant: Cardinal Health 414, LLC, Dublin, OH (US)

(72) Inventors: Dennis Eshima, Phoenix, AZ (US); Mehmet Husnu, Phoenix, AZ (US); James Stone, Alpharetta, GA (US); Derrick Alcaide, Los Angeles, CA (US); Joseph E. Zambanini, Delaware, OH (US); Thomas A. Klausing, Powell, OH (US); Chad E. Bouton, Powell, OH (US); Henry Padgett, Dublin, OH (US); Brian C. Kelley, Pataskala, OH (US); Scott N. Danhof, Plain City, OH (US); David A. Holley, Lancaster, OH (US); Jeffrey T. Stroup, Upper Arlington, OH (US); James B. Gleeson, Westerville, OH (US); Eric Hassenpflug, Westerville, OH (US); James A. Prescott, Columbus, OH (US); Herman Benecke, Columbus, OH (US); Daniel B. Garbark, Blacklick, OH (US)

(73) Assignee: Cardinal Health 414, LLC, Dublin, OH (US)

( * ) Notice: Subject to any disclaimer, the term of this patent is extended or adjusted under 35 U.S.C. 154(b) by 540 days.

This patent is subject to a terminal disclaimer.

(21) Appl. No.: 17/131,420

(22) Filed: Dec. 22, 2020

(65) Prior Publication Data

US 2021/0187467 A1 Jun. 24, 2021

Related U.S. Application Data

(63) Continuation of application No. 14/871,287, filed on Sep. 30, 2015, now Pat. No. 10,906,020, which is a
(Continued)

(51) Int. Cl.
*B01J 19/00* (2006.01)
*G21G 1/10* (2006.01)
(Continued)

(52) U.S. Cl.
CPC ....... *B01J 19/0006* (2013.01); *A61K 51/0491* (2013.01); *B01J 19/004* (2013.01);
(Continued)

(58) Field of Classification Search
CPC ...... B01J 19/0006; B01J 19/004; B01J 19/08; B01J 19/081; B01J 2219/00927;
(Continued)

(56) References Cited

U.S. PATENT DOCUMENTS

| 10,906,020 | B2 * | 2/2021 | Eshima | A61K 51/0491 |
| 2006/0245980 | A1 * | 11/2006 | Kiselev | B01J 19/004 422/130 |
| 2011/0150714 | A1 * | 6/2011 | Elizarov | B01J 19/0093 422/159 |

FOREIGN PATENT DOCUMENTS

WO WO-2008083313 A2 * 7/2008 ............. A61B 5/055

* cited by examiner

*Primary Examiner* — Jill A Warden
*Assistant Examiner* — Dwayne K Handy
(74) *Attorney, Agent, or Firm* — ArentFox Schiff LLP

(57) ABSTRACT

Systems, methods, and devices for generating radionuclides for use in production of radiopharmaceuticals; synthesizing the radionuclides generated and removing any unwanted products; measuring the quantity and activity level of the synthesized radionuclides; distributively delivering the (Continued)

radionuclides in appropriate quantities to modular cassette synthesis units in a modular cassette subsystem for contemporaneous/parallel production of radiopharmaceutical output and that allow reuse and/or quick, safe, and disposable replacement of portions of the subsystem; delivering non-radionuclide components to the modular cassette synthesis units as part of production of radiopharmaceutical output; measuring the quantity and activity level of each stream of radiopharmaceutical output; purifying the radiopharmaceutical output; dispensing individual doses in sterile vial(s); automatically producing labeling and dose related information; performing automated quality control on extracted samples of produced radiopharmaceutical output; and providing software and hardware controls for overall and subportion operation for optional remote data collection, communication, and/or control.

20 Claims, 57 Drawing Sheets

Related U.S. Application Data continuation-in-part of application No. 14/635,343, filed on Mar. 2, 2015, now Pat. No. 9,480,962, which is a continuation of application No. 13/550,026, filed on Jul. 16, 2012, now abandoned, said application No. 14/871,287 is a continuation-in-part of application No. 13/550,425, filed on Jul. 16, 2012, now abandoned.

(60) Provisional application No. 61/553,029, filed on Oct. 28, 2011, provisional application No. 61/508,373, filed on Jul. 15, 2011, provisional application No. 61/508,359, filed on Jul. 15, 2011, provisional application No. 61/508,394, filed on Jul. 15, 2011, provisional application No. 61/508,402, filed on Jul. 15, 2011, provisional application No. 61/508,349, filed on Jul. 15, 2011, provisional application No. 61/508,409, filed on Jul. 15, 2011, provisional application No. 61/508,294, filed on Jul. 15, 2011, provisional application No. 61/508,382, filed on Jul. 15, 2011, provisional application No. 61/508,464, filed on Jul. 15, 2011, provisional application No. 61/508,353, filed on Jul. 15, 2011, provisional application No. 61/508,374, filed on Jul. 15, 2011, provisional application No. 61/508,383, filed on Jul. 15, 2011, provisional application No. 61/508,367, filed on Jul. 15, 2011, provisional application No. 61/508,408, filed on Jul. 15, 2011.

(51) Int. Cl.
| | |
|---|---|
| *A61K 51/04* | (2006.01) |
| *B65B 3/00* | (2006.01) |
| *B65B 1/00* | (2006.01) |
| *G21G 1/00* | (2006.01) |
| *A61J 3/00* | (2006.01) |

(52) U.S. Cl.
CPC ............... *B65B 1/00* (2013.01); *B65B 3/003* (2013.01); *G21G 1/10* (2013.01); *A61J 3/002* (2013.01); *B01J 19/0046* (2013.01); *B01J 2219/00049* (2013.01); *B01J 2219/0072* (2013.01); *B01J 2219/00351* (2013.01); *B01J 2219/00355* (2013.01); *B01J 2219/00585* (2013.01); *B01J 2219/00693* (2013.01); *B01J 2219/00702* (2013.01); *B01J 2219/00722* (2013.01); *B01J 2219/00759* (2013.01); *G21G 2001/0015* (2013.01)

(58) Field of Classification Search
CPC ..... C07B 59/00; C07B 59/002; C07B 59/005; C07B 2200/05
See application file for complete search history.

| process map step ID | purpose | fluid | volume | current volume (uL) | scaled volume (uL) | reagent type | dry? | cold? | entry point | module source |
|---|---|---|---|---|---|---|---|---|---|---|
| Process starts here if QMA doesn't need conditioning: | | | | | | | | | | |
| 3 | product | F-18 in H2O | 3 mL | 3,000 | 3,000 | n/a | | | QMA column | splitter |
| 4 | elution | K222,K2CO3, in ACN/H2O | 0.8 mL | 800 | 800 | QMA Eluent | N | N | QMA colun | n/a |
| 5 | evaporation | Nitrogen (high & low pressure) | n/a | | | n/a | | | Reaction Vessel | N2 |
| 6,7,8 | drying | ACN | 2.4 mL | 2,400 | 600 | ACN | | | Reaction Vessel | n/a |
| 9a | labeling | ACN | 4.0 mL | 4,000 | 4,000 | Precursor | | | Reaction Vessel | n/a |
| 9b | labeling | Mannose Triflate (ACN from 9a dissolves) | | | | | Y | Y | | |
| 10 | SPE conditioning (2 columns) | EtOH | 3 mL | 3,000 | 750 | n/a | | | SPE column 1 : exit below SPE column 2 | n/a |
| 11 | SPE conditioning (2 columns) | H2O | 22 mL | 22,000 | 5,500 | n/a | | | SPE column 1 : exit below SPE column 3 | H2O |
| 12 | sample dilution | H2O | 22 mL | 22,000 | 5,500 | n/a | | | Reaction Vessel, or after | H2O |
| 13 | rinse RV walls | H2O | 4 mL | 4,000 | 1,000 | n/a | | | Reaction Vessel | H2O |
| 14 | Transfer fluid onto TC18 column | sum of steps 4,6,7,8,9,12,13: | | 33,200 | 8,300 | | | | | |
| 15 | washing | H2O | 46 mL | 46,000 | 11,500 | n/a | | | TC18 column | H2O |
| 16 | hydrolysis / elution | NaOH, 2N | 0.75 mL | 750 | 188 | NaOH | | | TC18 column | n/a |

FIG.9A

| | | | | | | | neutralizing reagent | N | neutralizing chamber | |
|---|---|---|---|---|---|---|---|---|---|---|
| 17 | neutralize pH | citrate buffer + HCl + EtOH + H2O | 6.4 mL | 6,400 | 1,600 | | | | n/a | |
| 18 | Transfer fluid onto TC18 column | sum of steps 16,17: | | 7,150 | 1,788 | | | | | |
| 19 | Push fluid through Alumina cartridge and 0.22 micron filter | n/a | n/a | n/a | n/a | | | | n/a | |
| 20 | Transfer fluid to hot cell | depends on whether TC18 is eluted | TBD | | | | | | | |
| 21 | flush cassette | H2O | TBD | | | | | | TBD: possibly several H2O | |
| | | volume totals | | | | | | | | |
| | | Flows into Neutralizing Chamber | uL | 1,788 | | | | | | |
| | | Flows through to waste | uL | 21,970 | | | | | | |
| | | stored in reagent pack | uL | 17,350 | 4,330 | | | | | |
| | | pumped from module | uL | 94,000 | 23,500 | | | | | |
| | | combined | uL | 111,350 | 27,830 | | | | | |

FIG. 9B

| process map step ID | purpose | fluid | volume | current volume (uL) | scaled volume (uL) | reagent name | dry? | cold? | entry point | module source |
|---|---|---|---|---|---|---|---|---|---|---|
| 2 | product | F-18 in H2O-18 | 3 mL | 3,000 | 3,000 | splitter bolus | | | QMA column | splitter |
| 3 | elution | K222,K2CO3, in ACN/H2O | 0.6ml | 600 | 150 | QMA Eluent | N | N | QMA column | n/a |
| | raise temp in RV to 70C for 1 min, then to 110C for 5 min, then to | | | | | | | | | |
| 4 | 110C (see step 6) | n/a | n/a | n/a | n/a | n/a | | Y | n/a | n/a |
| 5a | powder for mixing precursor | 2.0 mg AV105 | n/a | | | Precursor | Y | | mixed in Reagent Pack | n/a |
| 5b | solvent for mixing precursor | DMSO | 2-2.6mL | 2,300 | 575 | Precursor | | | Reaction Vessel | n/a |
| 6 | Labeling, 7min @110C | n/a | n/a | n/a | n/a | n/a | | | n/a | n/a |
| 7 | hydrolysis | HCl 3N | 0.7mL | 700 | 175 | Hydrolyzer | | | Reaction Vessel | n/a |
| 8 | 5 min @ 120C | n/a | n/a | n/a | n/a | n/a | | | n/a | n/a |
| | Cool RV to 50C | Coolant fluid (H2O or N2) | TBD | n/a | n/a | n/a | | | n/a | H2O/N2 |
| 9 | neutralization | NaOH 1N | 2.3 mL | 2,300 | 575 | Neutralizer | | | Reaction Vessel | n/a |
| 10 | HLB conditioning | EtOH | 5 mL | 5,000 | 1,250 | HLB conditioner1 | | | HLB column | n/a |
| 11 | HLB conditioning | 5% sodium ascorbate / H2O | 5 mL | 5,000 | 1,250 | HLB conditioner2 | Y | N | HLB column | n/a |
| 12 | Transfer fluid onto TC18 Column | sum of steps 3,5,7,9,12z | | 5,900 | 1,475 | n/a | | | n/a | n/a |
| 13 | HLB washing | 5% sodium ascorbate / H2O | 5 mL | 5,000 | 1,250 | HLB wash | Y | N | HLB column | n/a |
| | | 55% ACN/45% 25.2 mM ssd | | | | | | | | |

FIG. 11A

| | | | | | | Y | N | |
|---|---|---|---|---|---|---|---|---|
| 14a | Dilution formulation for HPLC | ascorbate +5% sod ascorbate/H2O | 3.0 mL | 3,000 | 750 | mobile phase match | | dilution vial | n/a |
| 14b | HLB elution | ACN | 1.5 mL | 1,500 | 375 | HLB eluent | | HLB column | n/a |
| 15 | Transfer fluid to HPLC | sum of steps 14a,14b | | 4,500 | 1,125 | | | HPLC | n/a |
| 16 | inject sample and acquire data | n/a | n/a | n/a | n/a | n/a | | HPLC | n/a |
| 17a | solvent rinse | H2O | 30 mL | 30,000 | 7,500 | solvent rinse | | C18 column | H2O |
| 17b | remove water | N2 | n/a | | | blow dry | | C18 column | |
| 18a | tC18 conditioning | EtOH | 5 mL | 5,000 | 1,250 | tC18 conditioner1 | | C18 column | n/a |
| 18b | tC18 conditioning | 5% sodium ascorbate / H2O | 5 mL | 5,000 | 1,250 | tC18 conditioner2 | Y | | |
| | Dilution for C18 for binding of | | | | | | | Dilution for C18 for | |
| 19a | product | 0.5% sodium ascorbate / H2O | 20 mL | 20,000 | 5,000 | Pre-SPE Diluent | Y | binding of product | n/a |
| 19b | product | product identified in HPLC | 4 - 12 mL | 8,000 | 2,000 | n/a | | mixing vial | n/a |
| 20 | Transfer fluid onto tC18 column | sum of steps 19a,19b | | 28,000 | 7,000 | | | | |
| 21 | washing | 0.5% sodium ascorbate / H2O | 15 ml | 15,000 | 3,750 | tC18 wash | Y | C18 column | n/a |
| 22 | elution | EtOH | 1 ml | 1,000 | 250 | tC18 eluent | | C18 column | n/a |
| 23 | reformulation for dosing | 0.5% sodium ascorbate in saline | 9 mL | 9,000 | 2,250 | Final Diluent | Y | final syringe | n/a |
| 24 | Transfer fluid to hot cell | sum of steps 22,23 | | 10,000 | 2,500 | | | | |
| 25 | flush cassette | H2O | TBD | | | | | TBD, possible several | H2O |
| | clear line | Nitrogen (high & low pressure) | n/a | | | n/a | | inlet reservoir | N2 |
| | cooling - external | compressed air | n/a | | | n/a | | Reaction Vessel | N2 |
| | | | | | | | | | |
| | | stored in reagent pack | uL | 75,400 | 18,850 | | | | |
| | | pumped from module | uL | 35,000 | 8,750 | | | | |
| | | combined | uL | 110,400 | 27,600 | | | | |

FIG. 11B

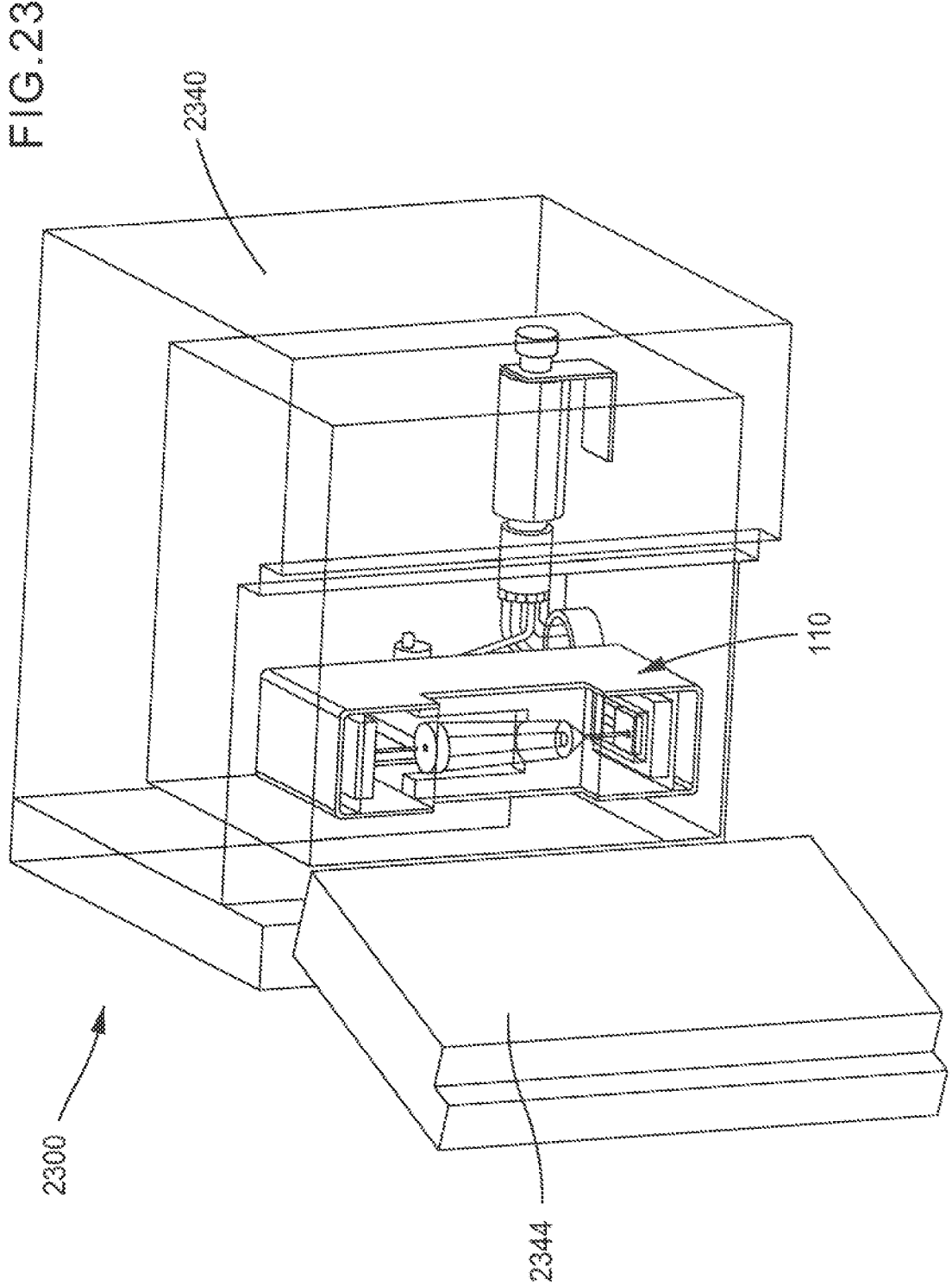

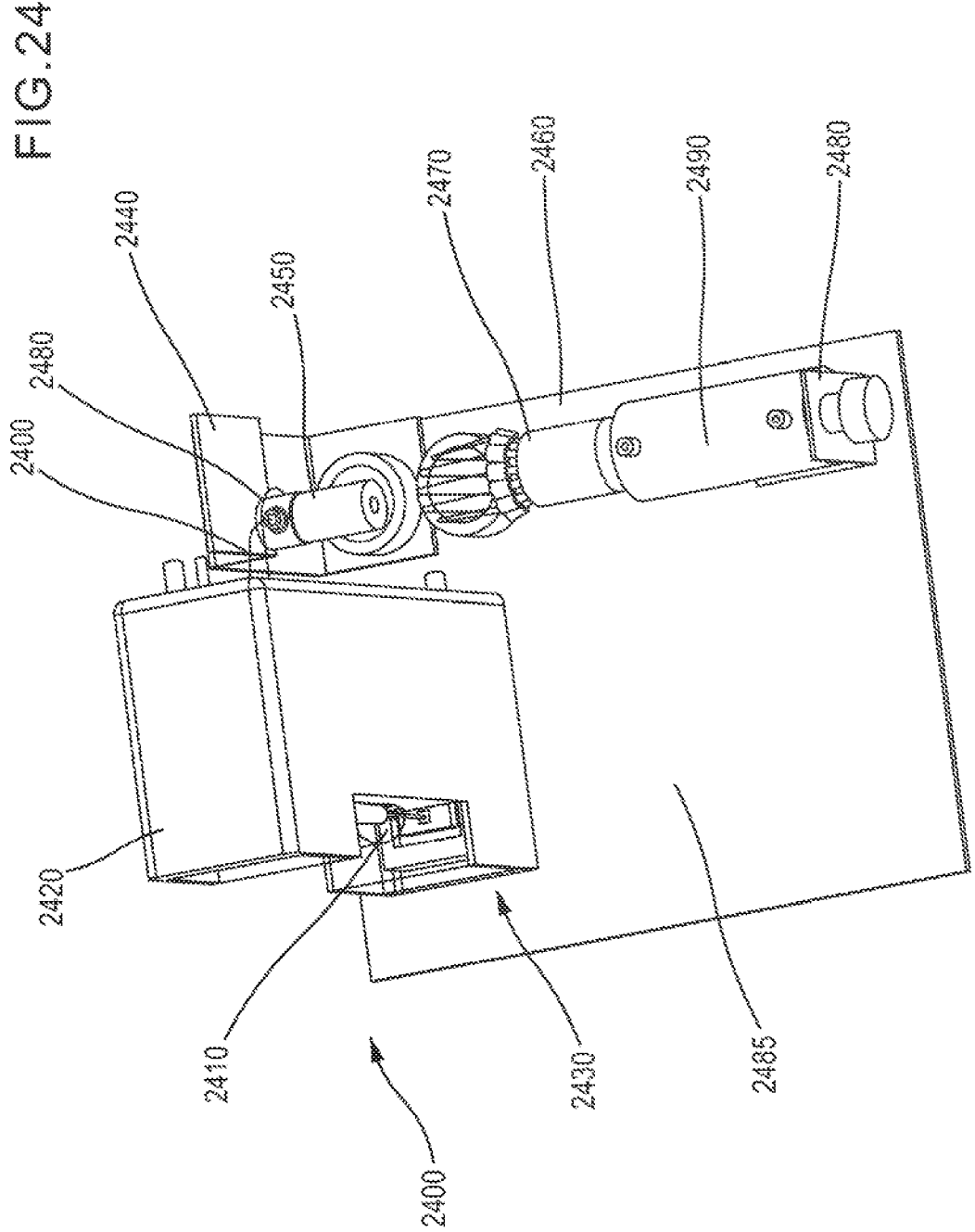

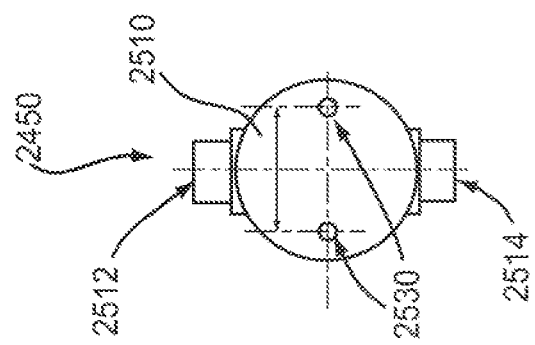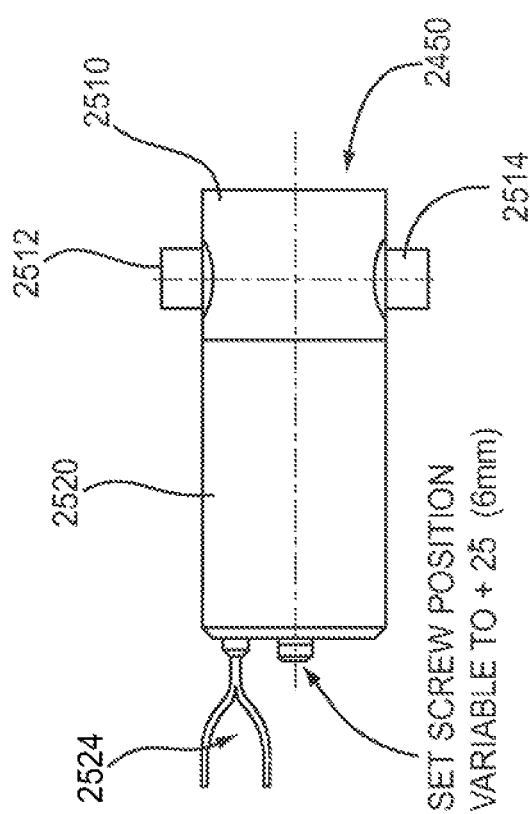

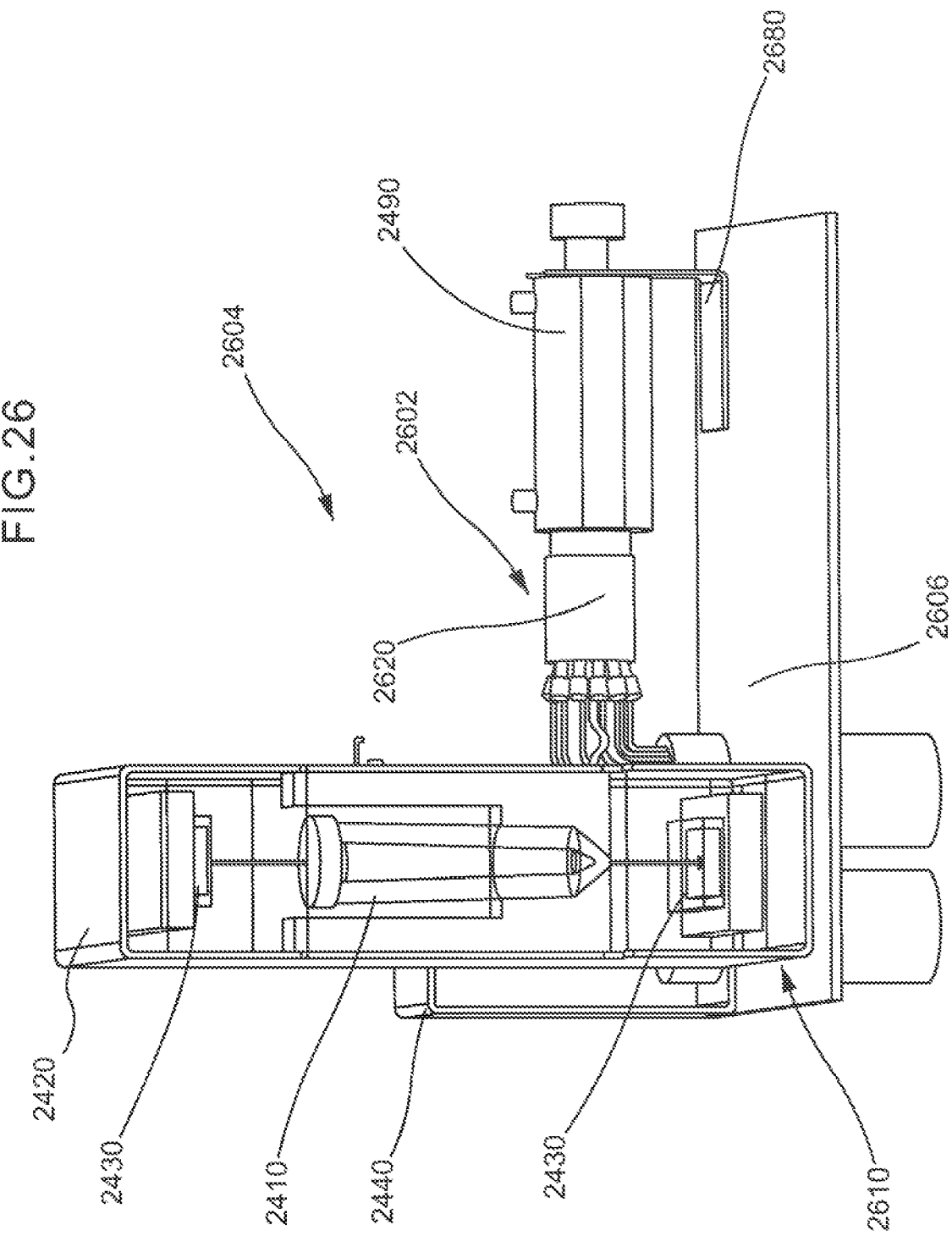

SYSTEMS, METHODS AND DEVICES FOR PRODUCING, MANUFACTURING AND CONTROL OF RADIOPHARMACEUTICALS

CLAIM OF PRIORITY UNDER 35 U.S.C. § 119 AND 35 U.S.C. § 120

This application is a continuation of U.S. patent application Ser. No. 14/871,287, entitled "SYSTEMS, METHODS AND DEVICES FOR PRODUCING, MANUFACTURING AND CONTROL OF RADIOPHARMACEUTICALS" filed on Sep. 30, 2015, which is a continuation of U.S. patent application Ser. No. 13/550,425 entitled "SYSTEMS, METHODS AND DEVICES FOR PRODUCING, MANUFACTURING AND CONTROL OF RADIOPHARMACEUTICALS-FULL" filed on Jul. 16, 2012, now abandoned, which claims priority to U.S. Provisional Application No. 61/508,294 entitled "SYSTEMS, METHODS, AND DEVICES FOR PRODUCING, MANUFACTURING, AND CONTROL OF RADIOPHARMACEUTICALS" filed on Jul. 15, 2011; U.S. Provisional Application No. 61/508,383 entitled "METHODS AND APPARATUS FOR FACILITATING THE PRODUCTION AND DISTRIBUTION OF RADIOPHARMACEUTICALS" filed on Jul. 15, 2011; U.S. Provisional Application No. 61/508,374 entitled "SPLITTER SYSTEM AND METHODS OF USE THEREOF" filed on Jul. 15, 2011; U.S. Provisional Application No. 61/508,382 entitled "MEMBRANE PUMPING SYSTEM AND METHOD IN A SURFACE CHANNEL FLUIDIC SYSTEM" filed on Jul. 15, 2011; U.S. Provisional Application No. 61/508,402 entitled "RADIOPHARMACEUTICAL CZT SENSOR AND APPARATUS" filed on Jul. 15, 2011; U.S. Provisional Application No. 61/508,394 entitled "ON-DEMAND PRODUCTION OF RADIONUCLIDES" filed on Jul. 15, 2011; U.S. Provisional Application No. 61/508,359 entitled "CASSETTE REACTION VESSEL USING A CASCADE OF VALVELESS PRESSURE PUMPS" filed on Jul. 15, 2011; U.S. Provisional Application No. 61/508,367 entitled "CASSETTE REACTION VESSEL" filed on Jul. 15, 2011; U.S. Provisional Application No. 61/508,464 entitled "METHODS AND COMPOSITIONS FOR DRYING IN THE PREPARATION OF RADIOPHARMACEUTICALS" filed on Jul. 15, 2011; U.S. Provisional Application No. 61/508,353 entitled "METHOD AND SYSTEM FOR AUTOMATED QUALITY CONTROL PLATFORM" filed on Jul. 15, 2011; U.S. Provisional Application No. 61/553,029 entitled "METHOD AND SYSTEM FOR AUTOMATED QUALITY CONTROL PLATFORM—PART 2" filed on Oct. 28, 2011; U.S. Provisional Application No. 61/508,408 entitled "METHOD FOR SYNTHESIZING LABELED COMPOUNDS" filed on Jul. 15, 2011; U.S. Provisional Application No. 61/508,349 entitled "SYSTEM FOR RADIOPHARMACEUTICAL PREPARATION INCLUDING HIGH PERFORMANCE LIQUID CHROMATOGRAPHY MODULE" filed on Jul. 15, 2011; and U.S. Provisional Application No. 61/508,409 entitled "CLOSED VIAL FILL SYSTEM FOR ASEPTIC DISPENSING" filed on Jul. 15, 2011. U.S. patent application Ser. 14/871,287 is also is a continuation-in-part of U.S. patent application Ser. No. 14/635,343 entitled "MODULAR CASSETTE SYNTHESIS UNIT" filed on Mar. 2, 2015, now issued as U.S. Pat. No. 9,480,962, which is a continuation of U.S. patent application Ser. No. 13/550,026 entitled "MODULAR CASSETTE SYNTHESIS UNIT" filed on Jul. 16, 2012, now abanonded, which claims priority to U.S. Provisional Application No. 61/508,373 entitled "MODULAR CASSETTE SYNTHESIS UNIT" filed on Jul. 15, 2011; U.S. Provisional Application No. 61/508,294 entitled "SYSTEMS, METHODS, AND DEVICES FOR PRODUCING, MANUFACTURING, AND CONTROL OF RADIOPHARMACEUTICALS" filed on Jul. 15, 2011; and U.S. Provisional Application No. 61/508,359 entitled "CASSETTE REACTION VESSEL USING A CASCADE OF VALVELESS PRESSURE PUMPS" filed on Jul. 15, 2011. Each of the preceding applications is incorporated by reference herein in its entirety.

FIELD

Aspects presented herein relate to the field of fully or partially automated production of radiopharmaceuticals, and in particular to systems, methods, and devices for safe, secure, reusable, and flexible: 1) production of radionuclides; 2) accurate measurement and combination of produced radionuclides with other radiopharmaceutical raw materials to produce one or more output streams of radiopharmaceuticals; 3) delivery of the output streams for individual dose level distribution; and 4) provision of quality control contemporaneously with radiopharmaceutical dose production and distribution.

BACKGROUND

Diagnostic techniques in nuclear medicine use radioactive tracers which emit gamma rays from within the body. These tracers are generally short-lived isotopes linked to chemical compounds which permit specific physiological processes to be studied. These compounds, incorporating radionuclides, are known as radiopharmaceuticals. They can be given by injection, inhalation or orally. In some diagnostic techniques, single photons are detected by a gamma ray sensitive camera, which can view organs from many different angles. The camera builds up an image from the points from which radiation is emitted; this image is enhanced by a computer and viewed by a physician on a monitor for indications of abnormal conditions.

Another recent development is Positron Emission Tomography (PET) which is a more precise and sophisticated technique using isotopes produced in a cyclotron, in which protons are introduced to the nucleus of a radioisotope, resulting in a deficiency of neutrons (i.e., becoming proton rich).

The nucleus of a radioisotope usually becomes stable by emitting an alpha and/or beta particle (or a positron). These particles may be accompanied by the emission of energy in the form of electromagnetic radiation known as gamma rays. This process is known as radioactive decay.

A positron-emitting radionuclide is introduced, usually by injection, and accumulates in the target tissue. As it decays, it emits a positron, which promptly combines with a nearby electron in the target tissue, resulting in the simultaneous emission of two identifiable gamma rays in opposite directions, each having an energy of 511 keV. These are conventionally detected by a PET camera and give a very precise indication of their origin. PET's most important clinical role is in oncology, with fluorine-18 (F-18) as the tracer, since it has proven to be the most accurate non-invasive method of detecting and evaluating most cancers. Fluorine-18 (F-18) is one of several cyclotron producible positron emitters (including also, Carbon-11, Nitrogen-13, and Oxygen-15) used in PET for studying brain physiology and pathology, in particular for localizing epileptic focus, and in dementia, psychiatry and neuropharmacology studies. They also have a significant role in cardiology. F-18 in FDG (fluorodeoxyglucose) has become very important in detection of cancers and the monitoring of progress in their treatment, using PET. A radioactive product such as F-18 in FDG is a specific example of a radiopharmaceutical. Other radiopharmaceutical agents include, but are not limited to, F-18 Fluorothymidine (FLT), F-18 Fluoromisonidazole-3-fluoro-1-(2 '-nitro-1'-imidazolyl)-2-propanol (MISO), F-18 Fluor Choline (FCH), and C-11 Acetate.

It is known in the related art to provide shielded containment systems for use in combining cyclotron produced radionuclides with non-radionuclide components to produce radiopharmaceuticals.

There are many drawbacks of these related art systems, including: 1) cyclotron production is often limited and does not allow the rapid production and distribution of short half-life radionuclides that are often needed; 2) typically only one radiopharmaceutical may be produced in a production run, after which various radionuclide raw material components and physical system components must be replaced and/or decontaminated, which can greatly delay the production process and/or make the process much less efficient; 3) many aspects of production of radiopharmaceuticals in such related art systems are not automated and/or may require time-consuming and/or awkwardly controlled hand production steps; 4) the radioactivity and/or quantities of the raw radionuclide and/or the produced radiopharmaceutical may be inaccurate and/or difficult to determine precisely; 5) necessary quality control to be performed on the output radiopharmaceutical products may be time-consuming, inaccurate, and/or require high levels of worker input/skill, further hampering production and/or timely delivery of the produced radiopharmaceuticals; 6) some or many aspects of the control, monitoring, and/or other production aspects may lack and/or hamper development of appropriate protections, such as shielding to minimize damage and maximize service life; 7) production/dispensing may be imprecise and/or inefficient for individual doses and/or may require inefficient or time consuming human intervention, as well as inefficient reuse of components and/or decontamination requirements; 8) control system software and hardware for overall operation and/or subsystem operation may be insufficient or not implementable; and/or 9) such existing systems may not provide or support use of remote and/or centralized data collection, control, and operation.

SUMMARY

Aspects presented herein overcome the above identified problems, as well as others, by providing systems, methods, and devices for producing radiopharmaceuticals that include: 1) generating radionuclides for use in production of radiopharmaceuticals, such as via use of a cyclotron (including enhanced systems, devices, and methods over the related art); 2) using the radionuclides generated to synthesize radiopharmaceuticals, and removing any unwanted products included with the generated radionuclides or radiopharmaceuticals or intermediate compounds in the synthesis (e.g., drying the generated radionuclides); 3) measuring the quantity and/or activity level of the synthesized radionuclides; 4) distributively delivering the radionuclides in appropriate quantities to a plurality of modular cassette synthesis units in a modular cassette subsystem for contemporaneous/parallel production of radiopharmaceutical output and to allow reuse and/or quick, safe, and disposable replacement of portions of the subsystem; 5) delivering appropriate quantities of non-radionuclide components to the plurality of modular cassette synthesis units as part of the contemporaneous/parallel production of radiopharmaceutical output; 6) upon production of the radiopharmaceutical output from the plurality of modular cassette synthesis units, measuring the quantity and activity level of each stream of radiopharmaceutical output (e.g., one or more radioactivity sensors or dose calibrators); 7) purifying the radiopharmaceutical output (e.g., removing any unwanted products included with the generated radionuclides, such as by drying and/or deprotecting the generated radionuclides and/or radiopharmaceuticals or intermediate compounds, which may optionally include use of one or more disposable columns); 8) distributively dispensing bulk product in one or more sterile vials or manufactured dose containers; 9) optionally automatically producing labeling and/or dose related information for use with the doses; 10) performing automated quality control on one or more extracted samples from the produced radiopharmaceutical output; and 11) providing software and/or hardware controls for overall and various sub-portion operation that include suitable radiation and other damage and contaminant resistant features and that allow for optional remote data collection and troubleshooting, communication, and/or control.

In one example implementation, a related art housing and other features typically used to produce a single radiopharmaceutical production run that may include significant human intensive input is used to house a plurality of modular subsystem components that automate and improve speed and accuracy of production, allow multiple radionuclide products to be produced contemporaneously/in parallel, and enable efficient and quick substitution of product runs.

In one example implementation, for reagent and synthesis operation, internal related art shielded openings used for components for a single product run are replaced with multiple subsystems that two or more contemporaneous/parallel production operations. In addition, cooperation among other system components allows increased production by allowing increased efficiency of feed and accuracy of both characteristics and volume of radionuclide and other raw material input to the production process.

Aspects presented herein include enhanced and/or alternative systems, devices, and methods for production and improved quality and quantity of raw radionuclides usable in the manufacture of radiopharmaceuticals.

Increase in automation of portions of operation, as well as improvement, reduction of size and cost, and advancement of operation of cooperating portions of reagent and synthesis operations results in the both increased speed and accuracy of production and decreased human exposure during the process. Subsystem components may be modularized, such by use of cassettes, and designed to allow interactive use that enables quick and simplified replacement/disposal of modules to, among other things, reduce contamination, enable quick and simplified input of selected raw material feeds, and enable simplified substitution of entire radiopharmaceutical processes.

Aspects include devices, systems, and methods for both measuring activity level of radionuclides and accurately determining the volume of such materials throughout the system increase both efficiency and quality of output. Such devices and systems also have enhanced robustness of operation in radiation and contaminant exposed environments.

In one example implementation, 10 of 11 steps in a quality control process are automated to run in parallel/contemporaneously and to run contemporaneously with dispensing and/or other operations of the manufacturing process, so as to reduce the time from manufacture to delivery of each radiopharmaceutical. This automated approach reduces delay, decreases the need for human resources (and thereby costs associated with human resource skills, as well as resulting in reduction in human errors), and enables more standardized quality control output.

In one example implementation, post radiopharmaceutical production manufacturing and/or purification processes are used to produce higher quality products more quickly than the related art. Such features may include, for example, use of high performance liquid chromatography (HPLC), low pressure chromatography, flash chromatography as well as types of Sep-Pak purification and isolation processes, and disposable columns.

In one example implementation, dose dispensing is automated and highly accurately controlled through use of subsystem components, and may be modularized, such as via use of cassettes, to allow interactive use that enables quick and simplified replacement/disposal of modules to, among other things, enable quick and simplified substitution of portions of or entire dose dispensing processes. In some variations, the accuracy of feeds is enhanced by use of robust detection devices, systems, and methods in conjunction with automated generation of information that enable accurate dose dispensing, for example, contemporaneously with accurate labeling and other information generation for dose dispensation over the lifetime of the radiopharmaceutical.

In example implementations, operations of the overall system, as well as subsystem features, may be controlled by one or more software and hardware control systems and methods of operation. Various operations, inputs, and/or output may thereby easily be centrally/remotely collected and/or controlled.

Additional advantages and novel features relating to aspects presented herein will be set forth in part in the description that follows, and in part will become more apparent to those skilled in the art upon examination of the following or upon learning by practice thereof.

BRIEF DESCRIPTION OF THE DRAWINGS

Aspects presented herein will become fully understood from the detailed description given herein below and the accompanying drawings, which are given by way of illustration and example only and thus not limited with respect to aspects of the present invention, wherein:

FIGS. 9A and 9B show an example FDG process chart, in accordance with aspects of the present invention;

FIGS. 11A and 11B show an example process chart for Example F-18 Product 1A, in accordance with aspects of the present invention;

FIGS. 22-28 show examples of a splitter subsystem in accordance with aspects of the present invention;

DETAILED DESCRIPTION

Aspects presented herein overcome the above identified problems, as well as others, by providing systems, methods, and devices for producing radiopharmaceuticals that include: 1) generating radionuclides for use in production of radiopharmaceuticals, such as via use of a cyclotron (including enhanced systems, devices, and methods over the related art); 2) using the radionuclides generated to synthesize radiopharmaceuticals, and removing any unwanted products included with the generated radionuclides or radiopharmaceuticals or intermediate compounds in the synthesis (e.g., drying the generated radionuclides); 3) measuring the quantity and/or activity level of the synthesized radionuclides; 4) distributively delivering the radionuclides in appropriate quantities to a plurality of modular cassette synthesis units in a modular cassette subsystem for contemporaneous/parallel production of radiopharmaceutical output and to allow reuse and/or quick, safe, and disposable replacement of portions of the subsystem; 5) delivering appropriate quantities of non-radionuclide components to the plurality of modular cassette synthesis units as part of the contemporaneous/parallel production of radiopharmaceutical output; 6) upon production of the radiopharmaceutical output from the plurality of modular cassette synthesis units, measuring the quantity and activity level of each stream of radiopharmaceutical output (e.g., via one or more hot cells); 7) purifying the radiopharmaceutical output (e.g., removing any unwanted products included with the generated radionuclides, such as by drying and/or deprotecting the generated radionuclides and/or radiopharmaceuticals or intermediate compounds, which may optionally include use of one or more disposable columns); 8) distributively dispensing individual doses in one or more sterile vials; 9) optionally automatically producing labeling and/or dose related information for use with the doses; 10) performing automated quality control on one or more extracted samples from the produced radiopharmaceutical output; and 11) providing software and/or hardware controls for overall and various sub-portion operation that include suitable radiation and other damage and contaminant resistant features and that allow for optional remote data collection, communication, and/or control.

In a radiopharmaceutical production facility, a cyclotron or linear accelerator may be used to prepare a material containing a radioisotope of interest which is delivered to a synthesis system. The radioisotope may emit one or more kinds of radiation, including electrons, positrons, gamma rays/x-rays, protons, neutrons, alpha particles, and other possible nuclear ejecta. In one example, a radioisotope, when added to other materials to be administered to a subject, may emit a positron, which then annihilates with an electron, for example, in human tissue, to produce gamma rays.

Figure 1:
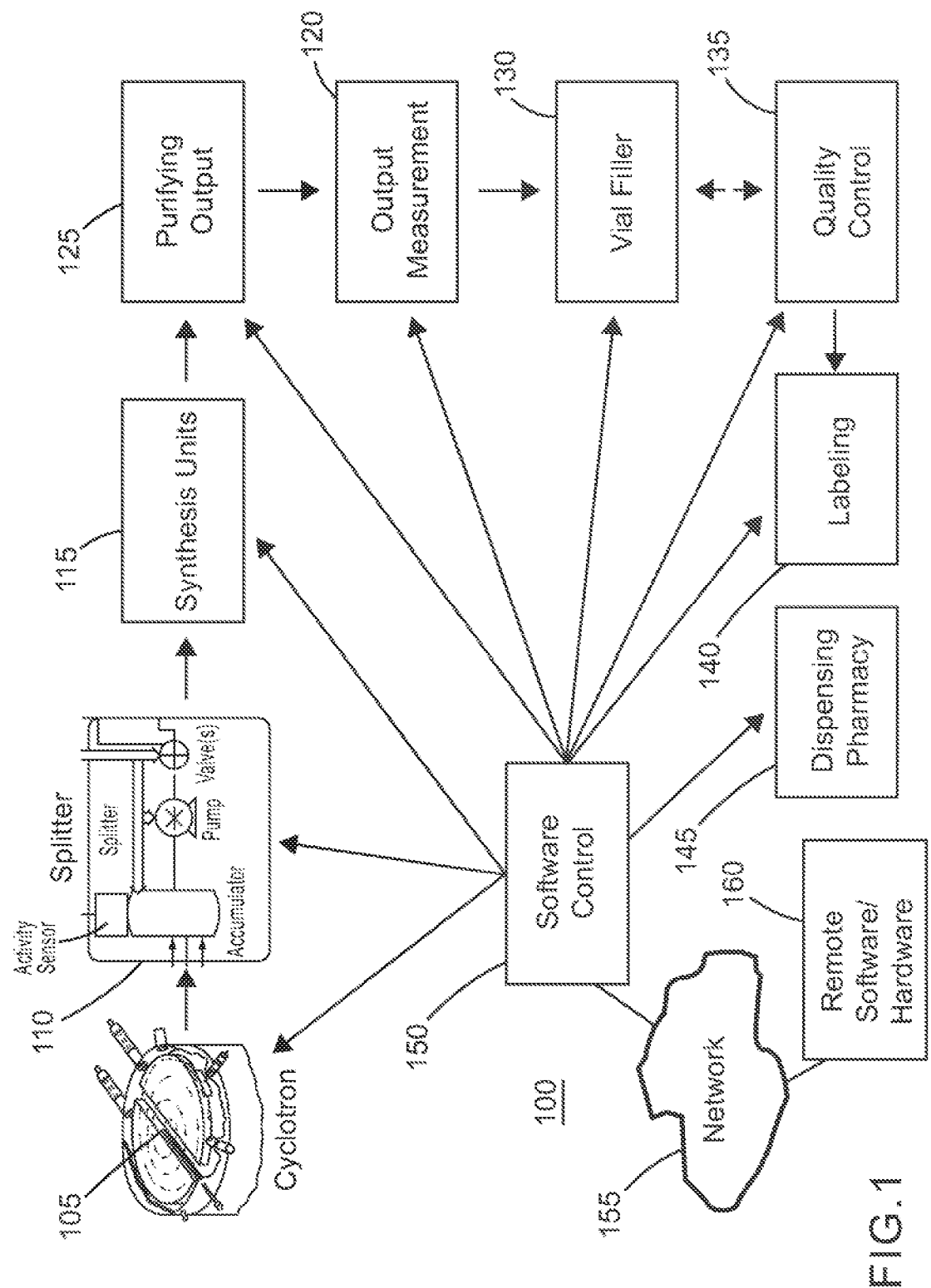
FIG. 1 presents a representative diagram of various portions of an example system in accordance with aspects of the present invention.

FIG. 1 presents a representative diagram of various portions of an example system in accordance with aspects presented herein. As shown in FIG. 1, the example system 100 includes a cyclotron or other device 105 for generating radionuclides (e.g., F-18) for use in production of radiopharmaceuticals; a splitter 110 for measuring (e.g., quantity and radioactivity) and accurately dividing the generated radionuclides into split streams for further production; one or more synthesis units 115 for further processing the radionuclides and/or other products to be combined with the radionuclides (e.g., modular cassette unit(s) to produce a radiopharmaceutical containing the radionuclides); an output measurement component 120 for measuring (e.g., quantity and radioactivity) the output from the synthesis unit(s); a purifying component for purifying the output (e.g., removing any unwanted products included with the generated radionuclides, such as by drying and/or deprotecting the generated radionuclides and/or radiopharmaceutical or intermediate compound, which may optionally include use of one or more disposable columns); one or more dispensing units 130, such as for distributively dispensing individual doses into one or more sterile vials; a quality control unit 135 for performing automated quality control on one or more extracted samples from the produced radiopharmaceutical output; an optional labeling component 140 for automatically producing labeling and dose related information for use with the doses output; an optional connection to a dispensing pharmacy that may be located remotely; and software and hardware control features 150, including network 155 (e.g., the Internet) and remote hardware and/or software components 160 for overall and various sub-portion operational control that optionally may allow for remote data collection, communication, and/or control.

For example, the amount of radiopharmaceutical product needed in a predetermined amount of time may be determined, the determined amount of radiopharmaceutical product may be produced using any combination of cyclotron 105, splitter 110, synthesis unit 115, purifying output 125, output measurement 120, vial filler, quality control, and labeling. The predetermined period of time may be a day. Thus, orders for the following day may be determined so that the correct amount of radiopharmaceutical product can be determined, produced, and distributed for use within the following day. The amount of radiopharmaceutical product produced for a corresponding remote dispensing pharmacy 145 may be transmitted to the dispensing pharmacy 145 in bulk quantity, and the corresponding amounts may be indicated to a pharmacist in order to draw the correct individual doses. Using software control 150, the dose may be automatically drawn and corresponding information provided to the pharmacist. Software control may receive information for a plurality of doses that will be required in the predetermined period of time and automatically begin the radiopharmaceutical production process without further user input. However, a user interface may be provided to receive user input regarding the desired amounts at the location of the splitter 110 and synthesis units 115. Software control 150 may receive information for required doses from a plurality of remote locations and combine the received information in order to produce the total amount of required radiopharmaceutical product. Thereafter, information for each of the required doses may be forwarded to the corresponding dispensing pharmacy 145 from which the dose should be drawn. As radio decay information is critical for the dispensing pharmacist to draw the correct individual dose, the automated system may take into account the production information for the radiopharmaceutical product was finished when indicating the amount for the individual dose. The automated system may further take into account the day or time at which each of a plurality of individual dose are intended to be used when determining the amount to be produced.

Hardware and/or software components 150 and 160 may comprise, for example, one or more personal computers (PCs), minicomputers, mainframe computers, microcomputers, telephonic devices, or wireless devices, such as a personal digital assistants ("PDA") or other hand-held wireless devices for receiving, storing, and processing data. The hardware and/or software may include a processor and a repository for data and/or couplings to a repository for data, via, for example, a network, such as the Internet or an intranet. The couplings may include, for example, wired, wireless, or fiberoptic links.

In one example implementation in accordance with aspects presented herein, the overall system architecture may include three major subsystems: a drug synthesis subsystem that may include a plurality of modules and cassettes, a fluid supply, a gas supply, a vacuum supply, and fluid recovery components; a splitter that may be housed outside/behind the mini-cell; and power and control electronics unit that may be housed outside/behind the mini-cell.

Figure 2:
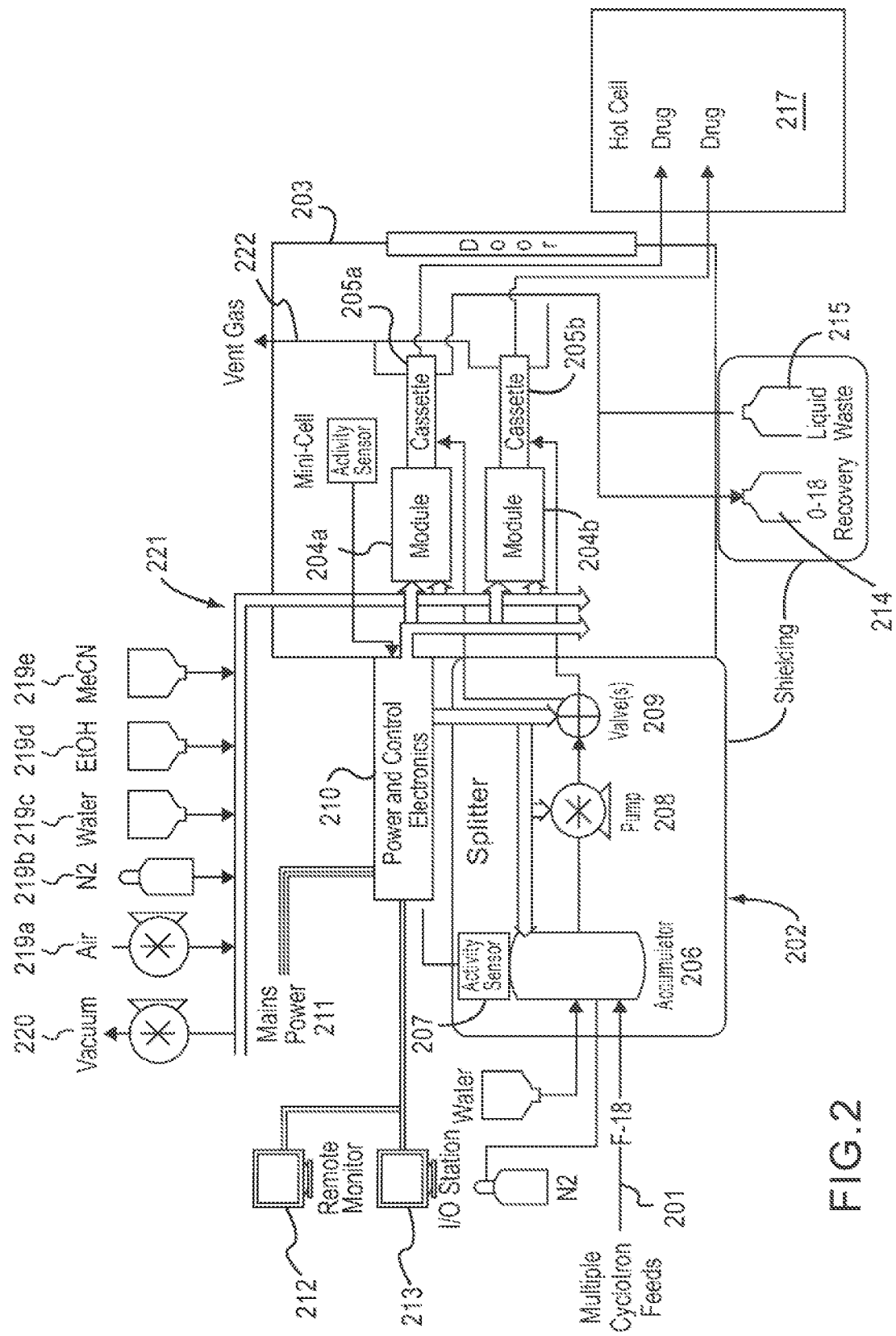
FIG. 2 shows a basic system schematic of one example of an overall system architecture, in accordance with aspects of the present invention.

FIG. 2 shows a basic system schematic 200 in accordance with one such example implementation. FIG. 2 illustrates a supply line 201 that receives radionuclides from a radionuclide generator, e.g., a cyclotron, and supplies the radionuclides to a splitter 202. Supply line 201 may be replaceable. Splitter 202 is illustrated adjacent to mini cell 203, and may be located in any shielded area outside of the mini cell 203. Splitter receives radionuclides from one or more cyclotrons and divides and routes the solution to a plurality of modules 204 and modular cassettes 205 comprised in the synthesis unit. Splitter may comprise an accumulator 206 for accumulating the received radionuclides, and a sensor such as an activity sensor 207, that measure the liquid volume and activity level of the received radionuclides. Activity sensor may comprise a CAV sensor as described in further detail in connection with FIGS. 12-18.

Once received, the radionuclide may remain in the accumulator until a product demand is identified. At that point, the volume of liquid required may be calculated and routed, e.g., pumped, to one of the plurality of cassettes in the synthesis unit or mini cell 203. Splitter may comprise a pump 208 and valve 209 for routing the required amount of radionuclides to the appropriate cassette. An example splitter is described in additional detail in FIGS. 22-28.

Mini cell 204, also referred to interchangeably herein as a synthesis unit, may comprise a plurality of modules 204 and cassettes 205 that are used to formulate the product. For example, six modules 204 and six cassettes 205 may be installed in a mini-cell 204. Mini-cell 204 may comprise a bulk fluid supply 218a, b, c, and d, a gas supply 219, and a vacuum supply 220. Mini cell 204 may also comprise a vent line 222 connecting each of the cassettes 205 to the exterior of the mini cell 204. A synthesis unit supply line 221 may connect each of these sources to each of a plurality of synthesis modules 204. The components comprised within the synthesis cassette may be configured in a lab-on-a-chip architecture, comprising all necessary reagents and supporting all synthesis reaction processes. The cassettes may receive radionuclides as a primary input and provide the pharmaceutical product as the primary output. Each cassette 205 is supported by a corresponding module 204 that provides the necessary connections for required bulk gases or fluids, along with proximity or physical interfaces for heating, cooling, and sensing. The provision of common solvents that tend to be used in large quantities via bulk containers reduces the required volume for each of the cassettes. This minimizes the size of each of the cassettes and maximizes the number of cassettes that can be provided in each mini cell.

Mini cell 203 may further comprise a sensor, e.g., an activity sensor 223.

At least one of the plurality of cassettes 205 and/or the plurality of modules 204 may comprise HPLC components for performing product purification. The HPLC component, therefore, may also comprise a connection to at least one of the other cassettes for receiving an output product from the cassette for purification.

Exit lines 214 and 215 may connect directly to each of the cassettes 205. One exit line 215 may receive liquid waste from each of the cassettes, and another exit line 214 may recover $H_2^{18}O$.

A product supply line 216 may connect each of the cassettes internal to the mini cell to the exterior of the mini cell, e.g., to a vial filler 217 exterior to the mini cell 204.

The system 200 may further include power and control electronics 210. The power and control electronics is illustrated in a location outside mini-cell 203 and splitter 202. The power and electronics 210 provide power to system components, receive sensor signals from system components, provides command/control signals to system components, executes system command and control, and provides a system user interface. This component 210 may interface the system 200 with a main power supply 211, a remote monitor 212, and component 213 for receiving user input and outputting information to users.

The supply lines throughout the system may be replaceable in order to prevent contamination and to enable quick turnaround between different products. For example, supply lines 201, exit lines 214 and 215, product supply lines 216, and synthesis unit supply line 221 may comprise a replaceable line.

Fluid recovery may comprise separate compartment for waste and for ---water.

The system may comprise an off state when no power is supplied to the system components, a standby state when power is supplied to the system components and system functions are not available to the splitter 202 and product synthesis subsystems, an operational state when system functions are available to the splitter 202 and product synthesis subsystems, and a service state during which system subsystems are not available to the splitter 202 and product synthesis subsystems and during which system components are selectively enabled and disabled in order to perform tests, repair components, or perform maintenance actions. The power and control electronics 210 may exist at the operational system level, as one of its functional roles may be to command and control the operation of the splitter 202 and the modules 204 within the synthesis product subsystems.

At the product synthesis subsystem level, the components comprised in the mini cell 203 may likewise comprise at least a standby state, an operational state, and a service state. At the Module 204 level, the components may comprise at least a standby state a ready state where module functions are available for performing product synthesis, and operational state, and a service state. At the splitter 202 level, the components may likewise comprise a standby state, a ready state, an operational state, and a service state.

Among others, such radiopharmaceutical products may include Fluordioxyglucose (FDG), F-18 Product 1A, Fluorothymidine (FLT), Fluoromisonidazole (F-Miso), F-18 Product 2, F-18 Product 1B, and F-18 Product 3.

Synthesis for certain products may be accomplished without the use of HPLC columns, such as the synthesis of FDG.

Figure 3:
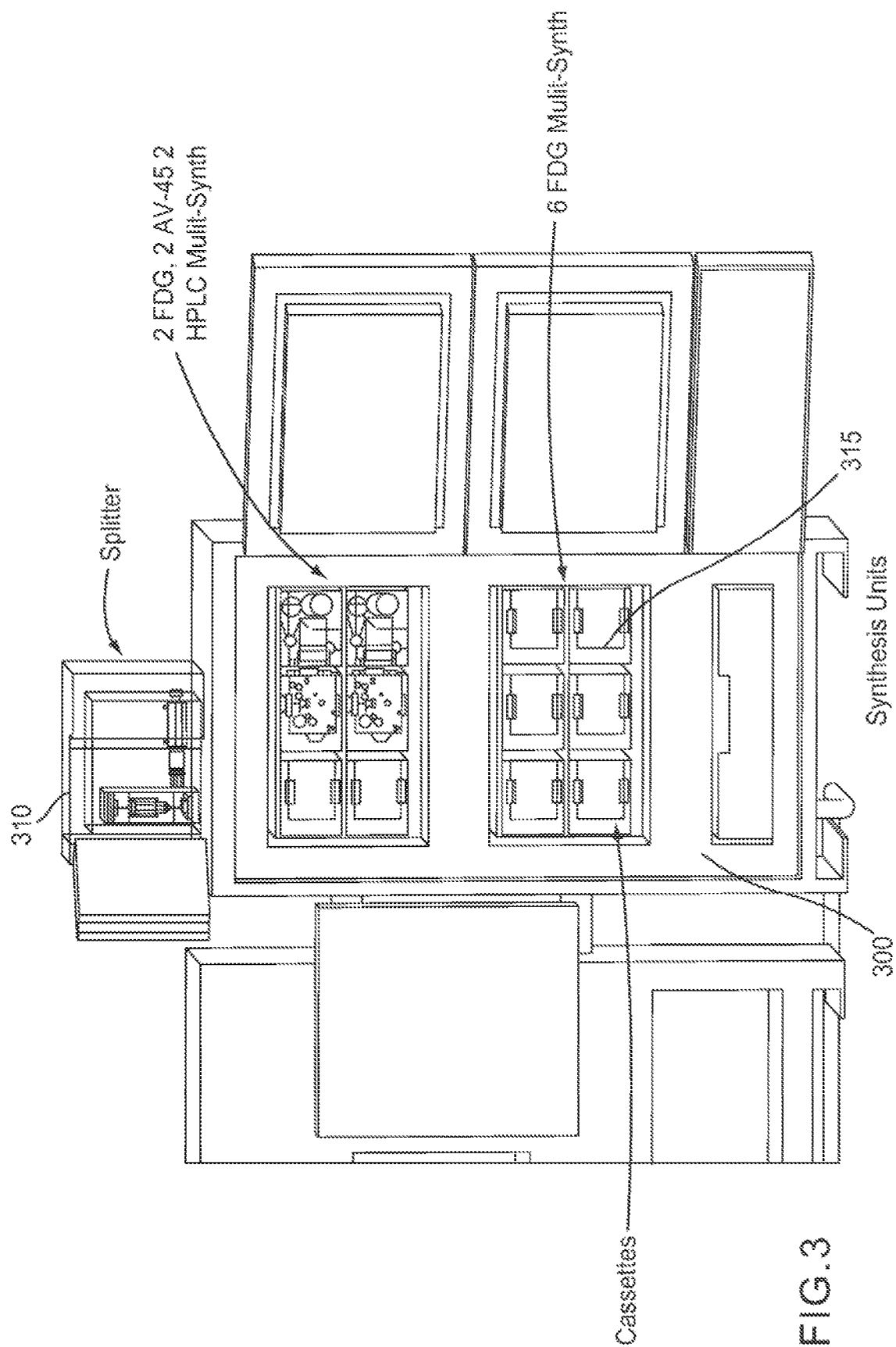
FIG. 3 shows a view of example synthesis units in an example housing and including an example splitter in accordance with aspects of the present invention.

FIGS. 3-6 show views of example implementations of various aspects in accordance with the example system of FIG. 1. FIG. 3 shows an example splitter 310 located atop a housing 300 that contains a plurality of synthesis units 315. The housing 300 may, for example, have been originally designed for handling a single synthesis portion, and, in accordance with aspects presented herein, multiple synthesis units 315, which may, for example, include cassette and other interchangeable subportions, may be sized and designed to fit the space originally designed for a single synthesis unit. Among other things, this approach to using multiple synthesis units within a single housing may allow multiple parallel processing of one or more radiopharmaceuticals, the same or different, for example, to be produced contemporaneously.

Figure 4A:
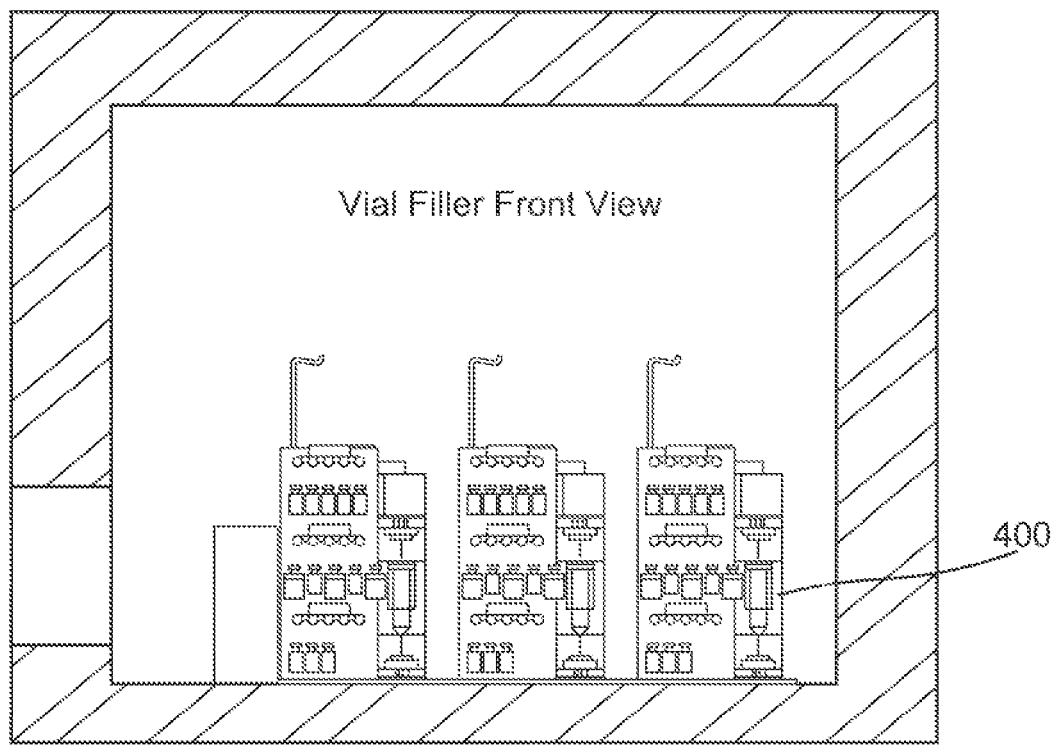
FIGS. 4A and 4B contain partial cutaway views of example shielded hot cells housing vial filler units for use in determination of final product activity (e.g., radiation) levels and dispensing production vials, in accordance with aspects of the present invention.
Figure 4B:
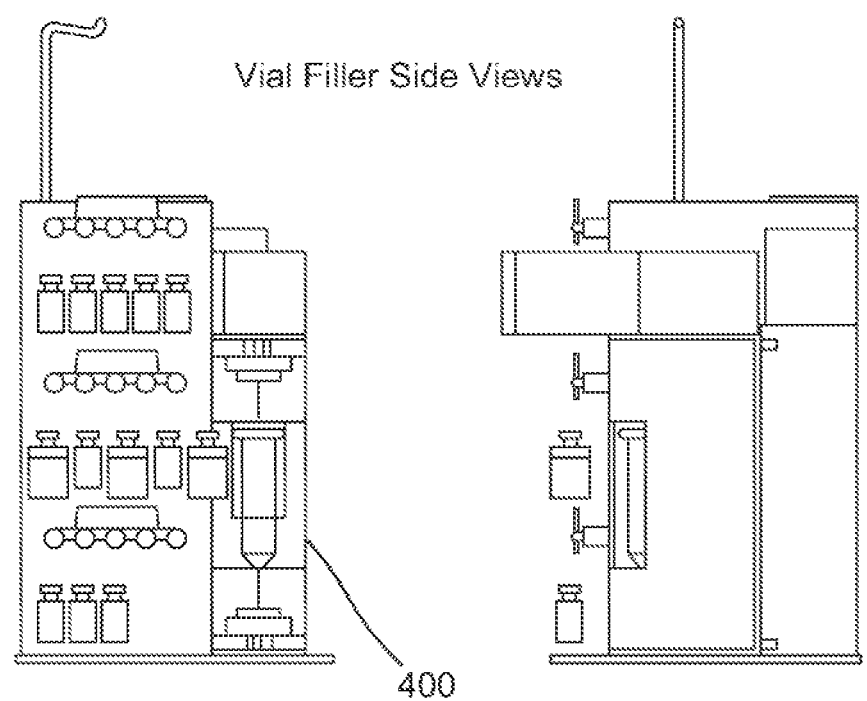

FIGS. 4A and 4B contain partial cutaway views of example vial fillers for use in determination of final product activity (e.g., radiation) levels, in accordance with aspects presented herein. The example hot cells may contain, for example, one or more component or subsystems for measuring product activity, such as by using containers for which activity level may be monitored using monitoring devices to determine activity level and volume (via relative activity level at differing locations). Such monitoring devices may include, for example, one or more specially designed CdZnTe ("CZT") solid state detectors for columnally measuring radiation contained within a container. The example hot cells may also contain dispensing units.

Figure 5:
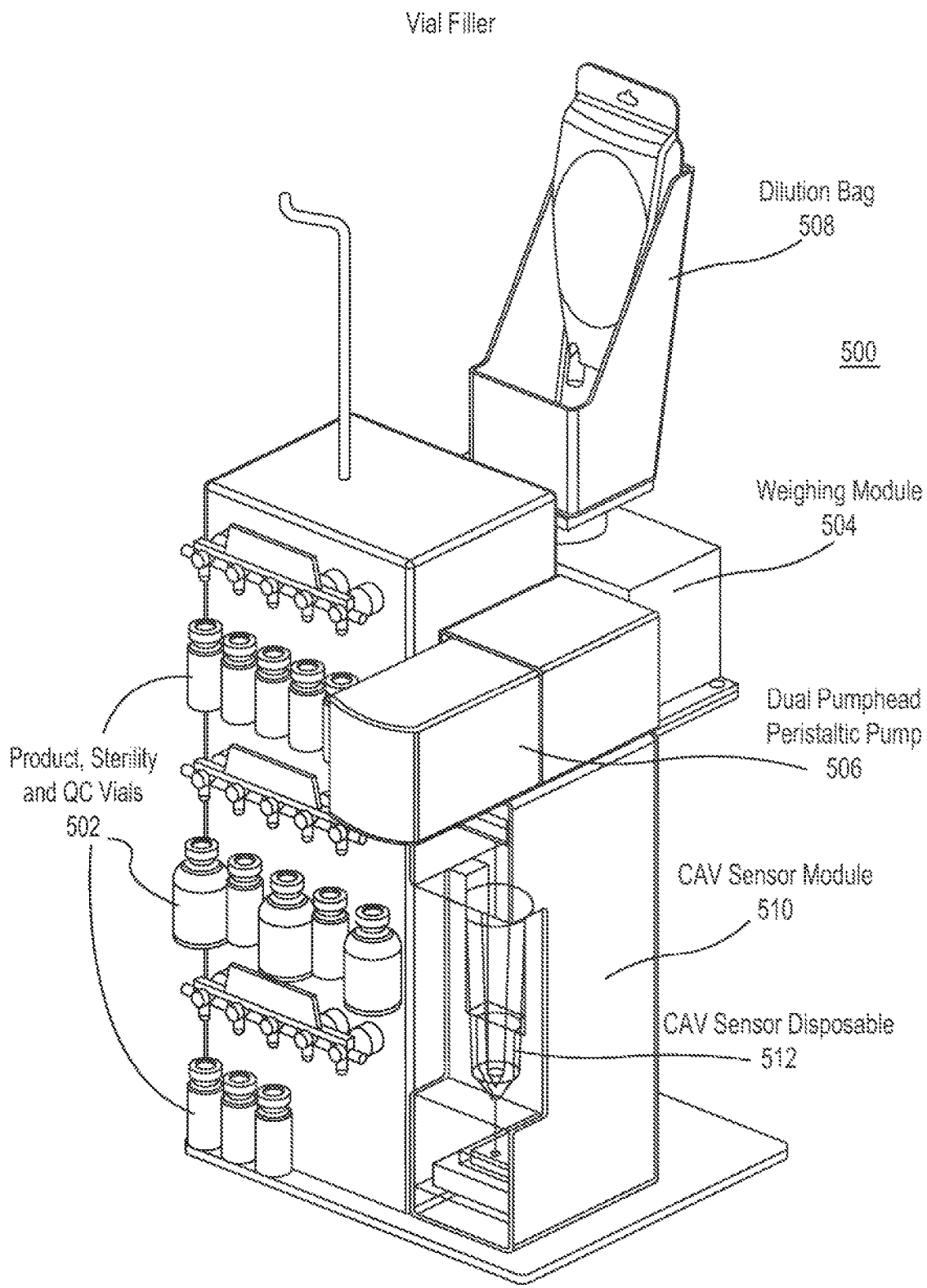
FIG. 5 shows an example dispensing unit, in accordance with aspects of the present invention.
Figure 6:
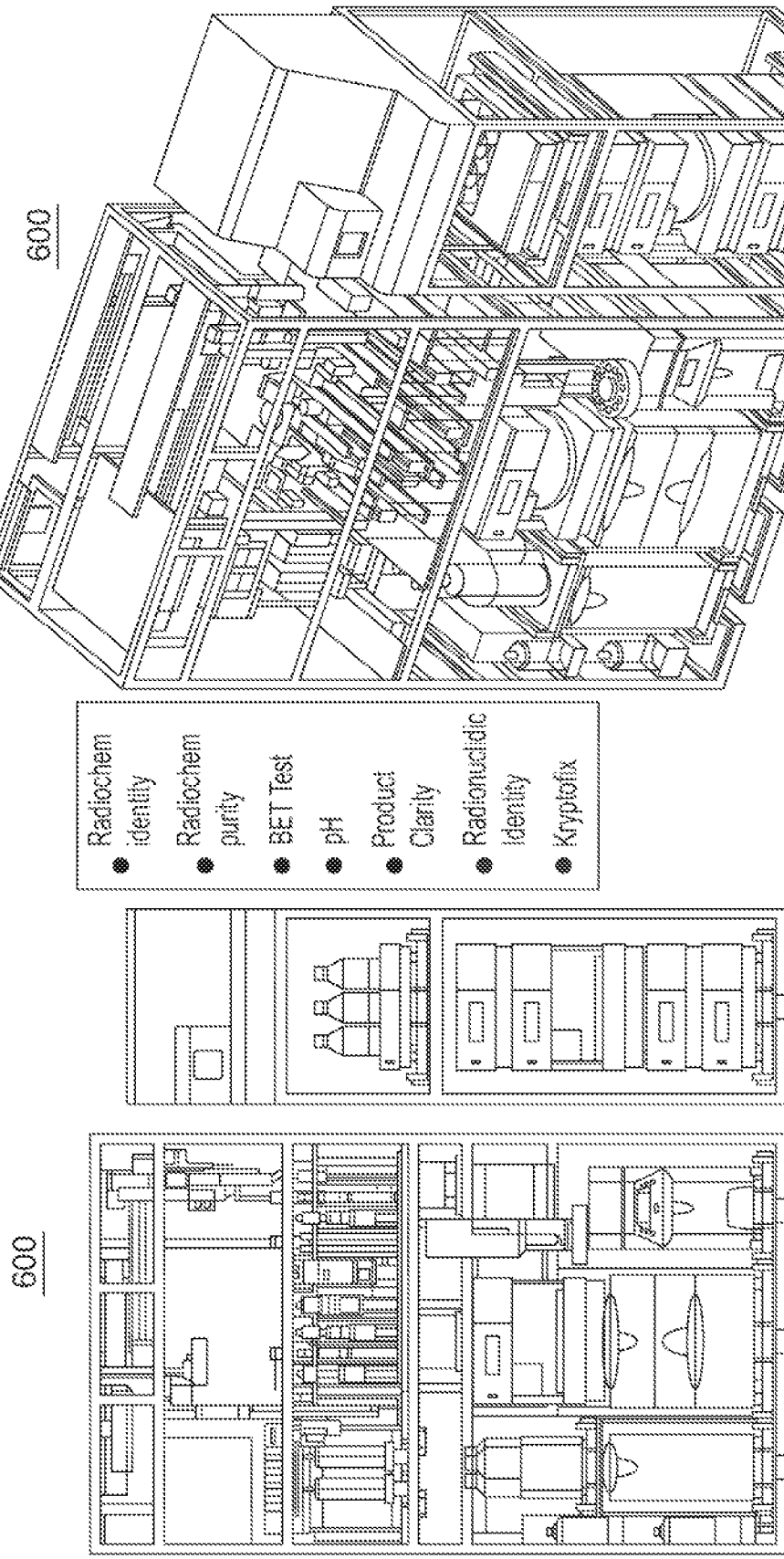
FIGS. 6A and 6B present cutaway views of an example quality control unit or subsystem for performing automated quality control on one or more samples extracted from the produced radiopharmaceutical output, in accordance with aspects of the present invention.
Figure 21A:
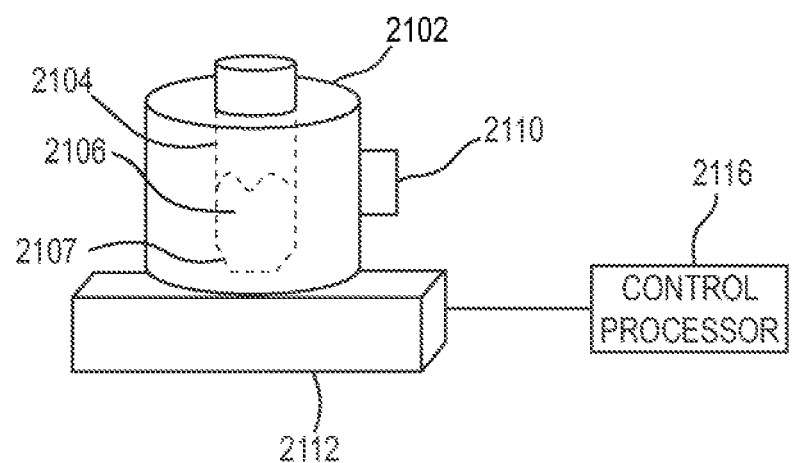
Figure 21B:
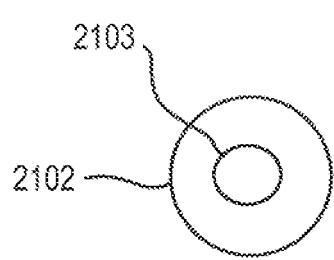
Figure 21C:
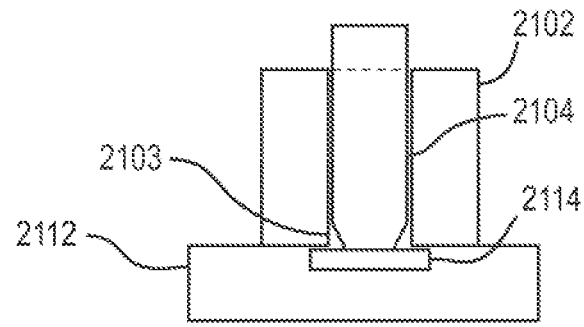

FIG. 5 shows another example dispensing unit 500, in accordance with aspects presented herein, such as a vial filling device or subsystem. The vial filling device is illustrated having a plurality of vials 502 that may be in different sizes. The vial filler 500 may include a weighing module 504, a pump 506 for filling a vial with a predetermined amount of radiopharmaceutical product, a dilution bag for diluting the radiopharmaceutical product, and a sensor 510. The sensor may comprise a CAV sensor module and a CAV sensor disposable portion. FIGS. 21a-c, for example, illustrate an example sensor and weighing component. The pump 506 may comprise a dual pumphead peristaltic pump.

FIGS. 6A and 6B present cutaway views of an example quality control unit or subsystem 600 for performing automated quality control on one or more samples extracted from the produced radiopharmaceutical output, in accordance with aspects presented herein. Among others, such quality control may comprise tests to confirm radiochem identity, radiochem purity, pH, product clarity, radionuclidic identity, kryptofix, and a BET test. Additional aspects of a quality control platform are disclosed in additional detail in U.S. Provisional Application No. 61/508,353 titled "Method and System for Automated Quality Control Platform," filed on Jul. 15, 2011, the entire contents of which are hereby incorporate by reference herein.

Figure 7:
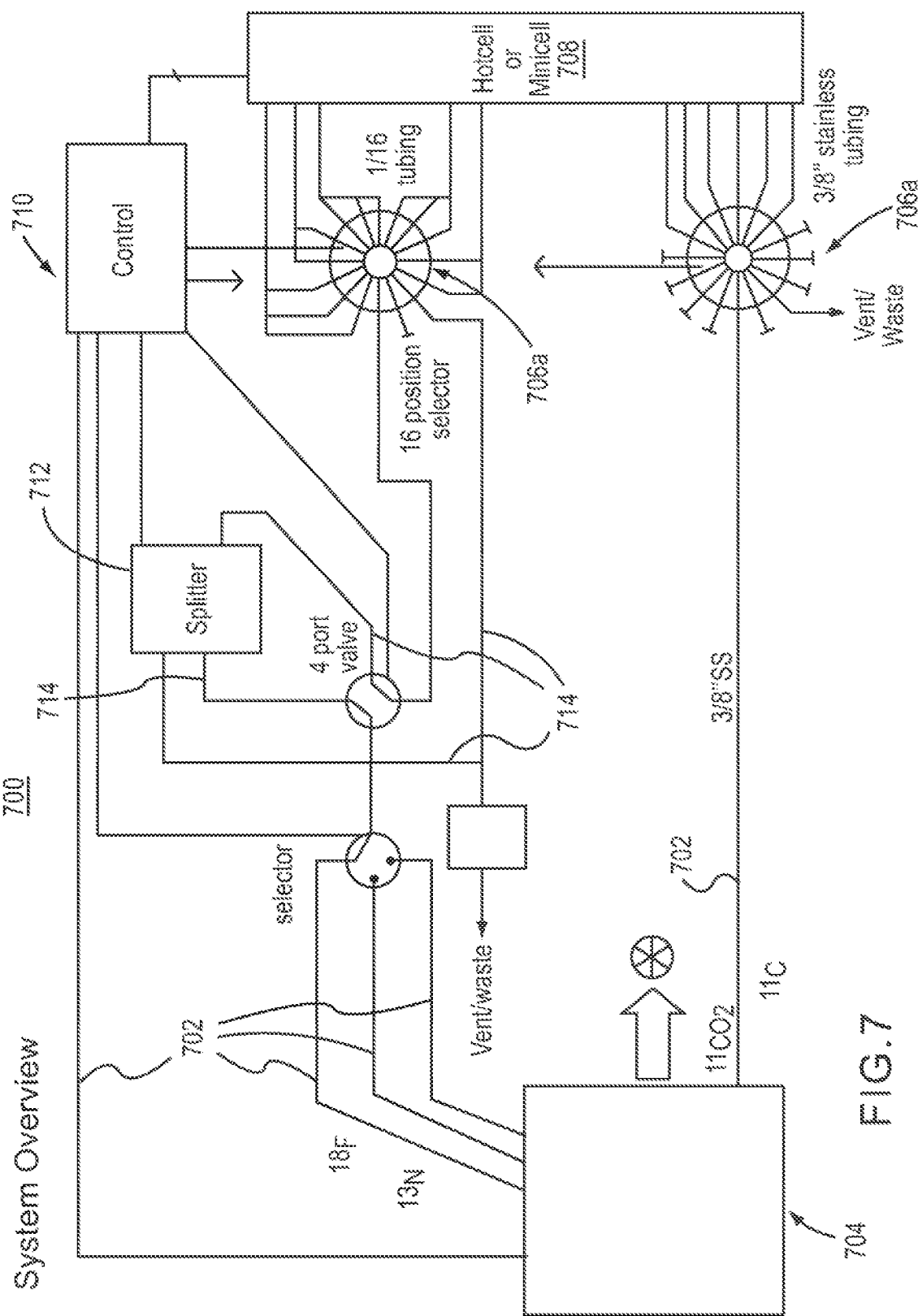
FIG. 7 illustrates a system diagram in accordance with aspects presented herein.

FIG. 7 illustrates a system overview diagram 700. FIG. 7 illustrates multiple lines 702 extending from a radionuclide generator 704, such as a cyclotron. The different lines 702 correspond to different radionuclides. For example, 11C is illustrated as connecting directly to a synthesis box selector 706a that distributes the active product comprising 11C to a minicell 708.

A control unit 710 controls each of the radionuclide generator, the splitter, the synthesis unit selectors 706a, 706b, and the minicell 708. Selectors 706a and 706b may be provided between the radionuclide generator 704 and selector 706a and between the splitter 712 and the synthesis unit selector 706b. The synthesis unit selector 706a and 706b then supplies the amount of active product received from splitter 712 to the appropriate module and cassette combination within the minicell 708. Although a single box is shown for the minicell 708, the minicell may represent multiple minicells or components provided in different room and having different production areas. Thus, the synthesis unit selectors 706a and 706b may supply active product to separate locations. The system 700 may also include rinse and gas supply lines 714, as further described in connection with aspects of a splitter.

Process Flow Charts and Schematics

Process maps for producing example radiopharmaceutical synthesis products are illustrated in FIGS. 8-11. These maps describe one or more of the steps and details that define each process For FDG, F-18 Product 1A, FLT, F-Miso, F-18 Product 2, F-18 Product 1B, and F-18 Product 3. Cassette schematics are illustrated in FIGS. 30-44 corresponding to the process maps. FIGS. 9 and 11 provide a list of fluid volumes at each step to accompany the cassette schematics for an FDG example and an F-18 Product 1A.

Common process fluids, such as water, acetonitrile, and ethanol, which appear in many places in the process maps and/or may be used in multiple different processes, may be provided as bulk utilities to each module, as illustrated in FIG. 2. In contrast, reagents, for example, which often have different concentrations of solutes in different process steps, may be packaged in a disposable reagent pack that is attached to the disposable synthesis cassette. In one variation, fluids that could mix with the process fluids during synthesis may also originate in the reagent pack, for example, to simplify quality assurance.

The cassette schematics and volume tables for the provided examples of the FDG and Example F-18 Product 1A processes, may be mapped onto example cassette schematic designs. The lists of fluid volumes incorporate a scaling down of each process to use ¼ of the volume of fluid currently used at each step. This approach may be used, for example, to size the reaction vessel and mixing chambers. The volumes required, and other process details, may be adjusted depending on circumstances.

Figure 8A:
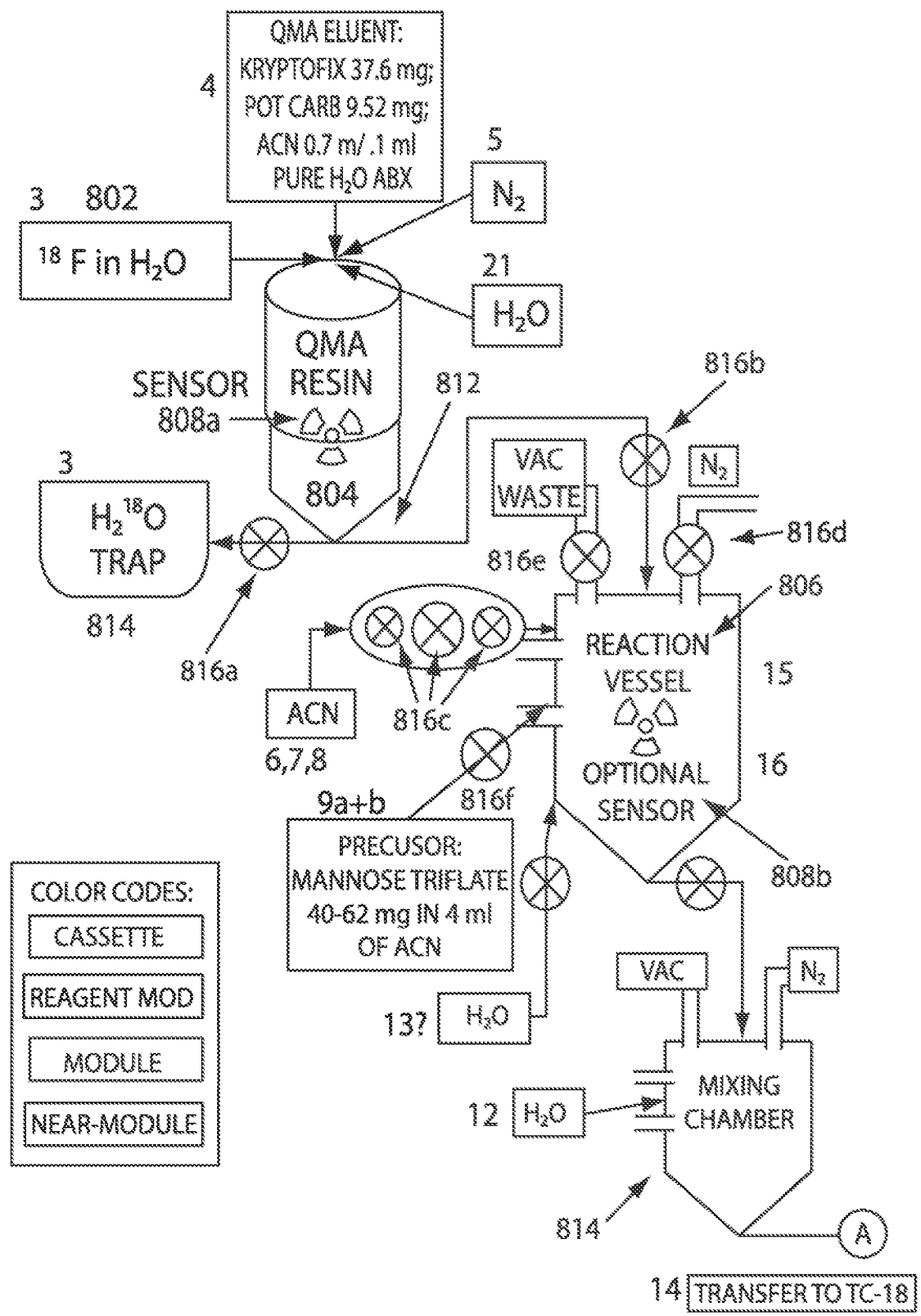
FIGS. 8A and 8B show an example FDG schematic using isolation valves around a reaction vessel and pressure pumping for fluid transfer, in accordance with aspects of the present invention.
Figure 8B:
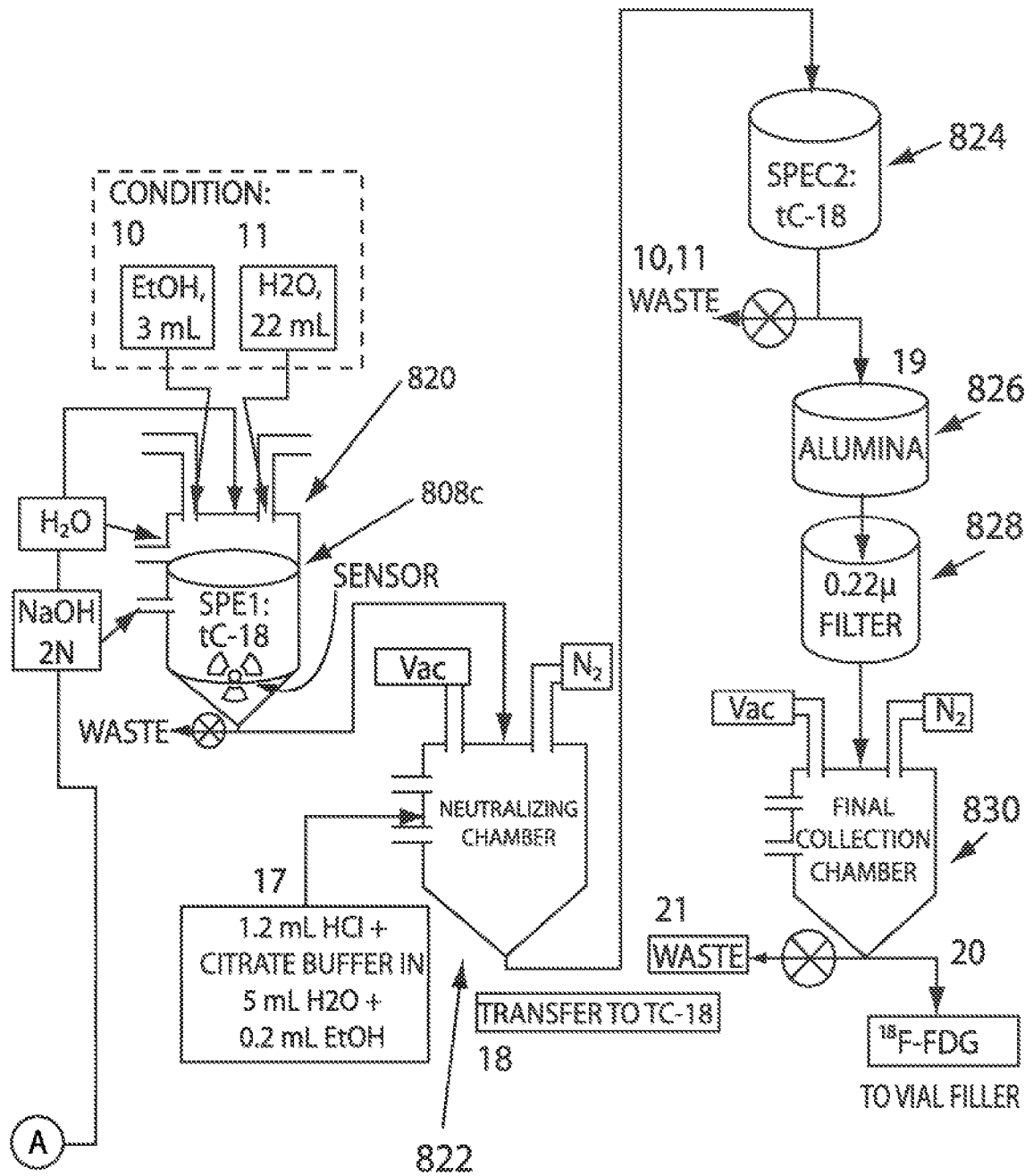

FIG. 8 shows an example FDG schematic 800 using isolation valves around a reaction vessel and pressure pumping for fluid transfer, in accordance with aspects presented herein. Schematic 800 illustrates components comprised in the synthesis unit 115, e.g., mini cell 203. In the schematic, active product 802, e.g., 18F in water is supplied to a first compartment 804. The active product 802 may be received from a cyclotron or splitter, as illustrated in FIG. 1. Additional materials, e.g., $N_2$, water, and eluent 806, may be added to the active product 802 in the first compartment 804, and the combined material is thereafter supplied to a reaction vessel 806. A first sensor 808a may measure the activity and/or volume of the material in the first compartment. At the exit of the first compartment 804, a supply line may be provided to the reaction vessel, and a second line 812 may lead to a fluid trap 814 for recycling at least part of the fluid, e.g., $H_2^{18}O$.

An isolation valve 816a may be provided between the exit of the first compartment and the fluid trap, and another isolation valve 816b may be provided between the reaction vessel 806 and the first compartment 804. Reaction vessel 806 may comprise connections to receive additional materials, e.g., $N_2$, water, ACN, and a precursor and to connect to a vacuum for waste 818. Each of these connections may comprise an isolation valve 816c-h. A second sensor 808b may also be provided at reaction vessel for measuring activity and/or volume. The material exits the reaction vessel and is supplied to a mixing chamber 818. Mixing chamber may have additional connections, e.g., to receive water and $N_2$, and a vacuum. The mixing chamber may enable post mixing for dilution or hydrolysis. The material may be provided from the mixing chamber 818 to a fourth compartment 820. The fourth compartment may include connections to receive additional material, a vacuum, and to distribute waste. A third sensor 808c may be provided to measure activity and/or volume for the fourth compartment 820. The material may be supplied from the fourth compartment 820 to a neutralizing chamber 822. The neutralizing chamber 822 may include connections to receive additional material, and a vacuum. The material may be supplied from the neutralizing chamber through additional compartments 824 and 826 or filters 828. The end product is then supplied to a final collection chamber 830. Final collection chamber may comprise connections to receive additional material, to a vacuum, and to a waste line. The final collection chamber 830 then supplies the final product to a vial filler, e.g. 130, 217, 400, and 500. The compartments and lines illustrated in schematic 800 are comprised in the cassette or module within the synthesis unit.

FIG. 9 shows an example FDG process chart corresponding to the schematic in FIG. 8, in accordance with aspects presented herein.

Figure 10A:
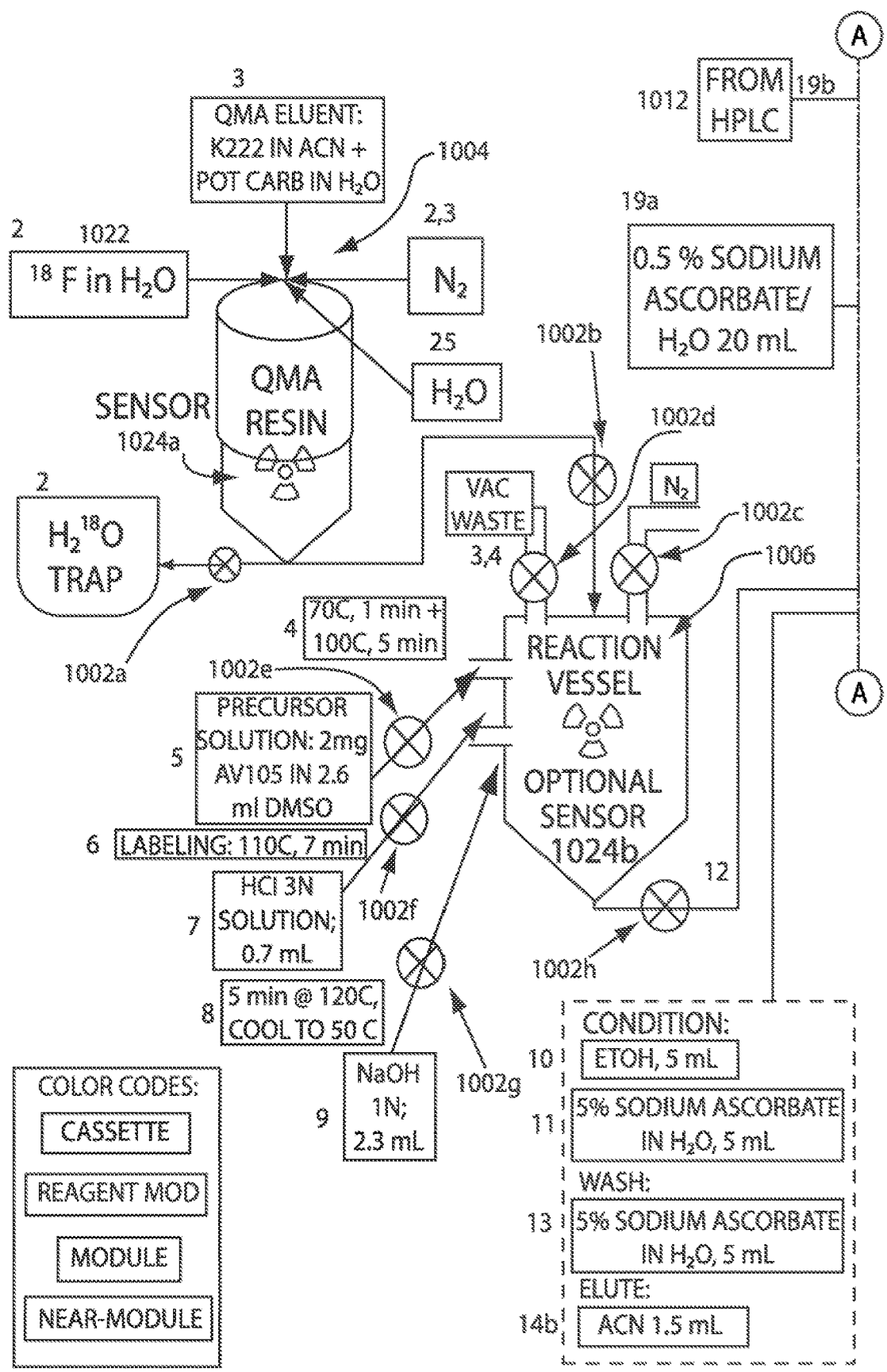
FIGS. 10A and 10B show the Example F-18 Product 1A process schematic using isolation valves around a reaction vessel and pressure pumping for fluid transfer, in accordance with aspects of the present invention.
Figure 10B:
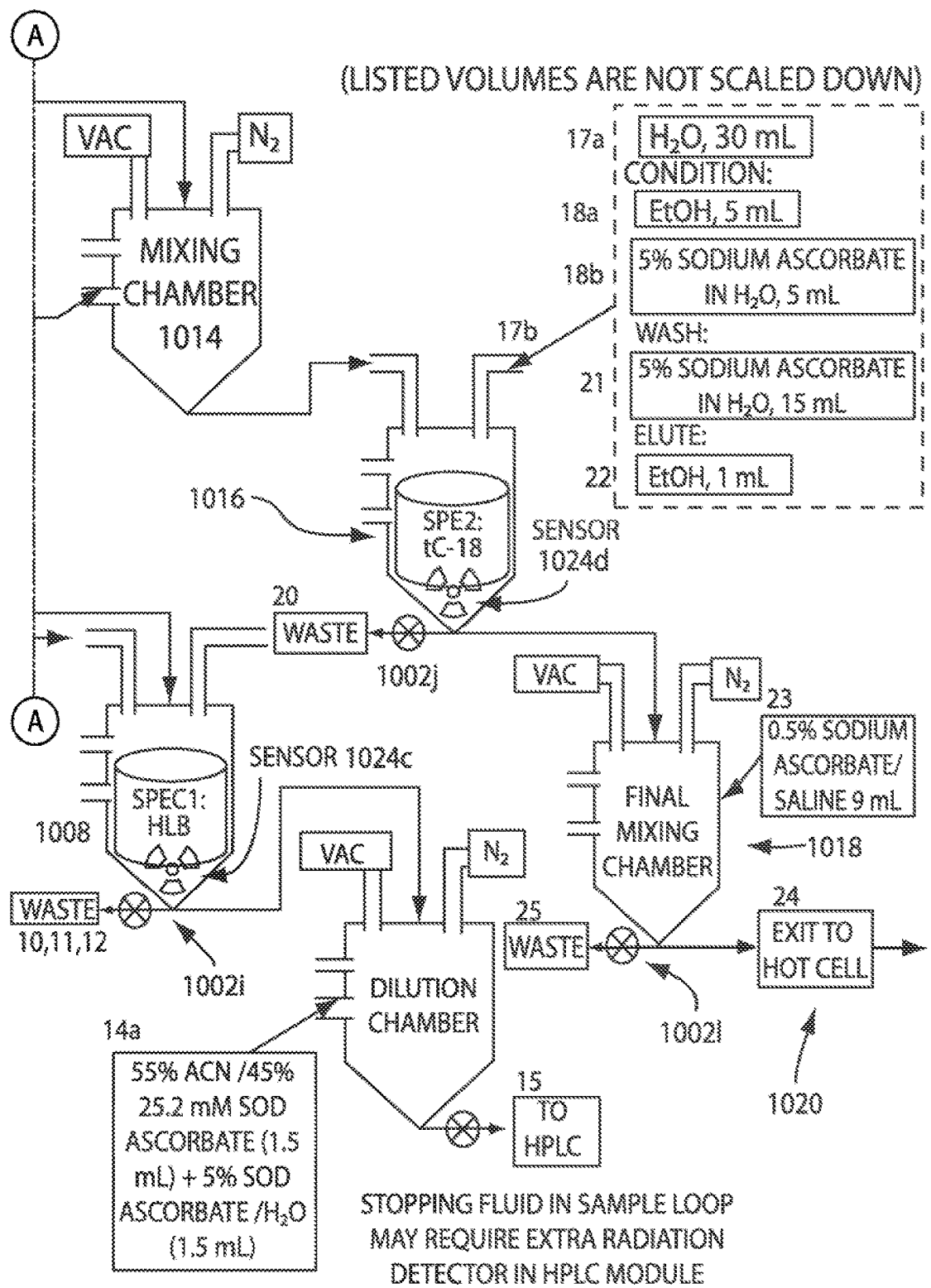

FIG. 10 shows the Example F-18 Product 1A process schematic 1000 using isolation valves 1002 *a-l*, e.g., around a reaction vessel and pressure pumping for fluid transfer, in accordance with aspects presented herein. The schematic illustrates a first compartment 1004, a reaction vessel 1006, a third compartment 1008, a dilution chamber 1010, a mixing chamber 1014, a sixth compartment 1016, and a final mixing chamber 1018. The active product 1022 is received in the first compartment 1004. The active product 1022 may be received from a cyclotron or splitter. The active product is combined with additional materials and transferred to the various compartments. Between the dilution chamber 1012 and the mixing chamber 1014, the material may be transferred to an HPLC 1012 for purification. After the final mixing chamber 1018, the final product may be supplied to a vial filler 1020. Any of a first sensor 1024a, second sensor 1024b, third sensor 1024c, and fourth 1024d may be provided at the first compartment 1004, reaction vessel 1006, third compartment 1008, and sixth compartment 1016, respectively, in order to measure activity and/or volume at those locations. As described in more detail in connection with FIG. 8, each of the compartments or vessels may comprise additional connections for receiving additional materials or a vacuum connection, or for disposing of waste material.

FIG. 11 shows an example process chart for Example F-18 Product 1A corresponding to the schematic in FIG. 10, in accordance with aspects presented herein.

Cyclotron Increased Production Process

Figure 12:
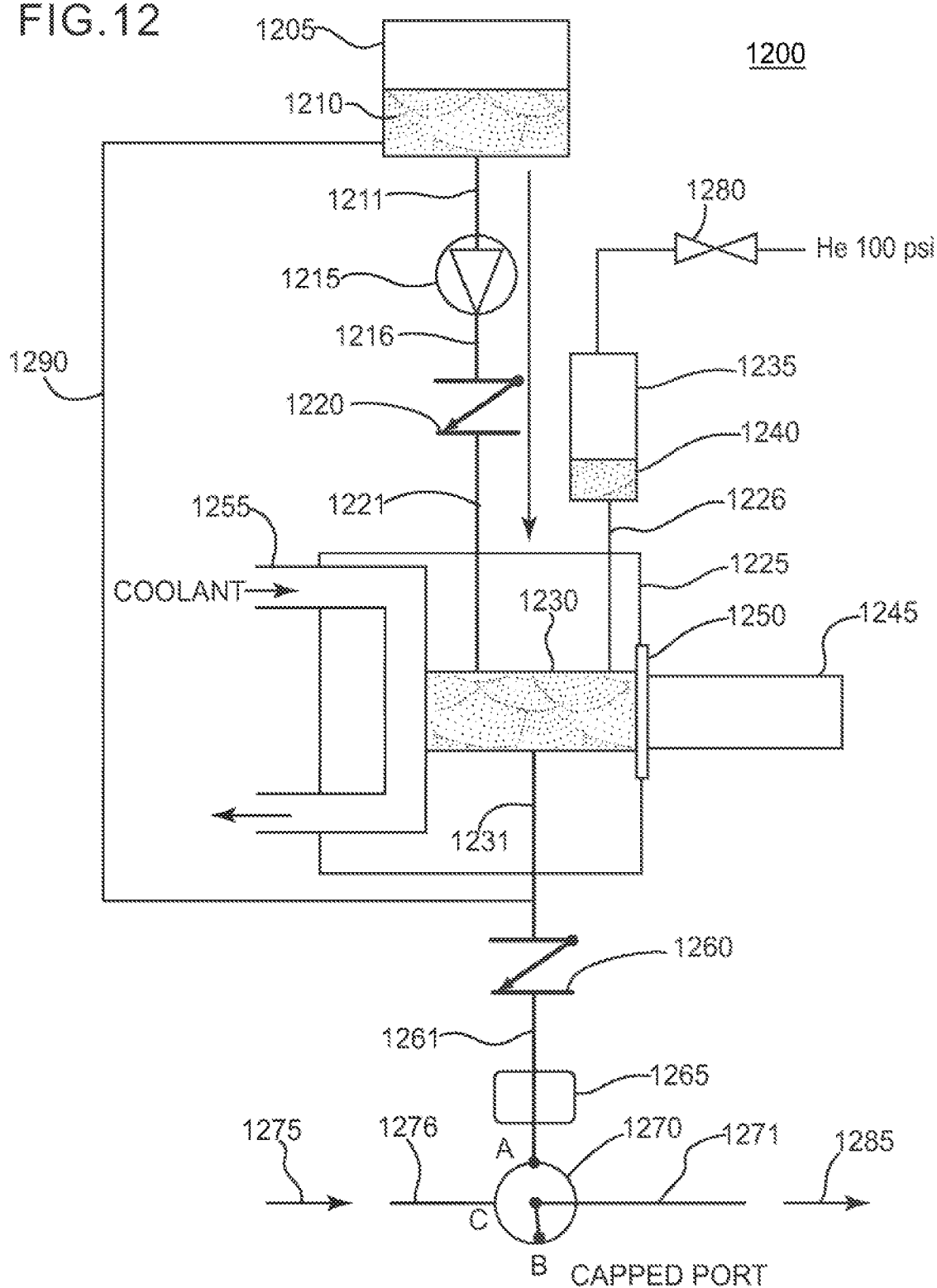
FIG. 12 shows an example device for enhanced generation of F-18 radionuclide on demand, in accordance with aspects of the present invention.

Aspects presented herein include methods and systems for enhanced generation of a radionuclide, such as F-18, on demand, as shown in FIG. 12. F-18 has a half-life of approximately 110 minutes, which is beneficial in that it does not pose a long-term environmental or health hazard. For example, after 24 hours, the radioactivity level is approximately 0.01% of the product when freshly produced in a cyclotron. Consequently, transport time from the production source to clinical use should be minimized to retain a maximum potency for accurate diagnostic value.

Conventionally, F-18 radionuclide is prepared in batches by radiating O-18 with protons from a cyclotron. Each batch must be synthesized with a pharmaceutical chemical that is preferentially absorbed by tumors. For example, F-18 FDG is a glucose-like molecule that is preferentially absorbed in tissue with high metabolic activity, which is common for some types of tumors. The radionuclide, when synthesized with a carrier molecule, may be diluted, subdivided and distributed to containers of specific volume, and therefore, of specific activity for infusion to a patient, where enhanced absorption in certain tissue, especially tumors, enables PET imaging.

The synthesis of a radiopharmaceutical such as F-18 FDG begins with a supply of O-18 rich water ($H_2^{18}O$). Because O-18 occurs with a natural abundance of approximately 0.2%, a concentrated supply of O-18 rich water (as $H_2^{18}O$) may be costly. Currently 10 g of 98% $H_2^{18}O$ may cost on the order of $400-$500. Therefore, efficient use of $H_2^{18}O$ to synthesize F-18 FDG, and timely supply for diagnostic use once the radionuclide is created is both a cost and time driven process.

Some tumors, such as prostatic tumors, are much less active, and therefore a glucose-like radiopharmaceutical is not as selectively absorbed. In that case, C-11 acetate is a radiopharmaceutical that is preferably used to image evidence of prostate cancer. However, C-11 has a half-life of 20 minutes, which requires a diagnostic imaging system to be closely co-located with a cyclotron to quickly deliver the synthesized radiopharmaceutical to the patient with sufficient efficacy. It is not uncommon for C-11 to decay by several half-lives before diagnostic application for imaging. Therefore, timing is an even more critical element in production.

There is a need, therefore, for a method and apparatus to timely generate and deliver a radionuclide as needed, rather than to provide it from prepared batches which lose efficacy with batch storage for delayed application.

The on-demand system illustrated in FIG. 12 addresses these needs by providing a system for continuous production of a radionuclide on demand. This system and related methods include a pump and a first check valve to control delivery of a metered amount of a fluid containing O-18 atoms to a target cell irradiated by a proton beam, wherein the proton beam converts O-18 to radioactive F-18. A second check valve may be coupled to the target cell to control continuous removal of a portion of the solution enriched with F-18. A gas pressurized switching valve chases the portion of the solution enriched with F-18 from the system.

FIG. 12 shows a schematic illustration of a radionuclide continuous production system 1200 capable of producing an amount of radionuclide on demand. The radionuclide, may then be provided to a synthesizing system to bind the radionuclide to a molecule that is preferentially absorbed in a specified tissue, such as a tumor, relative to normal tissue or other differentiated organ tissues. The exemplary case described is with respect to proton conversion of oxygen-18 to fluorine-18 in a nuclear reaction with protons. The oxygen-18 is provided in the form of $H_2^{18}O$, which is bombarded in a cell with protons from a cyclotron having several MeV energy. However, the system 1200 may be adapted to generate other radionuclides, where the source nucleus for conversion, bombarding particle and carrier solution transporting the source nucleus may be chosen appropriately.

In an aspect of the disclosure, the production system 1200 illustrated in FIG. 12 may include a storage vessel 1205 that contains a quantity of O-18 in the form of stored $H_2^{18}O$ 110. The vessel 1205 may include a low positive pressure level of He gas to maintain a non-reactive environment in the vessel, and further to pressurize the $H_2^{18}O$ 1210 through a transfer line 1211. A metering pump 1215 may draw $H_2^{18}O$ from the storage vessel 1205 through the transfer line 1211 at a selected rate, or to maintain a line pressure of, for example, 100 psi downstream. A check valve 1220 coupled to the metering pump 1215 via a transfer line 1216 maintains pressure in the lines, e.g., at 100 psi, opening to continue transfer of $H_2^{18}O$ to a target cell 1230 contained in a target housing 1225 via a transfer line 1221 when the line pressure is sufficient. The target cell 1230 may be on the order of 1-5 ml in volume, thereby enabling irradiation of a small volume of H$_2$$^{18}$O and consequent conversion of the small amount of O-18 to F-18, as determined by the volume of the target cell, to a concentration and an activity level determined by an amount of time of exposure to the proton beam.

The target cell 1230 interfaces with an evacuated tube 1245 via a foil 1250. The foil 1250 may comprise Havar™, a heat treatable cobalt base alloy, which can provide sufficient strength to withstand the pressure differential between the target cell 1230 and the evacuated tube 1245 at elevated temperatures, is corrosion resistant and non-magnetic. In accordance with an aspect of the disclosure, Havar™ may be used as a pressure diaphragm foil 1250 to retain the H$_2$$^{18}$O in the target cell 1230. The evacuated tube 11245 on an opposite side of the foil 1250 from the target cell may interface with a cyclotron (not shown) to introduce a beam of protons at several MeV energy. Energy losses of the proton beam in passing through the foil 1250 may be on the order of 1 Mev or more.

Because the beam energy may be on the order of 10-20 MeV, and the proton beam current may be on the order of 10-200 μamperes or more, the power deposited in the target cell 1230 may be on the order of 100-4000 watts, or greater, which can result in heating and boiling of the H$_2$$^{18}$O within the target cell 1230, and consequent over pressurization. An expansion chamber 1235 may be coupled to the target cell 1230 via a transfer line 1226 to relieve overpressure due to boiling expansion.

Additionally, a cooling heat exchanger 1255 may be coupled to the target housing 1225 and target cell 1230 to remove accumulated heat and maintain the target housing 1225, target cell 1230 and foil 1250 at or below a selected temperature. The cooling heat exchanger may be a water line, where the water is chilled to absorb heat from the target housing 1225 and target cell 1230. Alternatively, the heat exchanger may be a cooling or refrigeration system based on heat exchange other than water cooling.

A check valve 1260 following the target cell 1230 coupled to the target cell 1230 via a transfer line 1231 maintains line pressure upstream at, for example, 100 psi (cracking pressure 100 psi), and opens to permit transfer of irradiated fluid—which now contains F-18—to pass through a flow-through radiation detector 1265 via a transfer line 1261 when valve 1280 is closed and valve 1270 moves to position A. The flow through radiation detector 1265 measures a radiation activity level of the transferring fluid. By integrating the activity level over the transferred volume, it is possible to determine the accumulated activity level and total dose passing the radiation detector 1265. A 4-way valve 1270 is normally in position B so that no fluid or gas is admitted. When the valve 1270 moves to position A when ready for delivery, the metering pump 1215 runs for so a predetermined level of F-18 activity passes the detector 1265. The valve 1270 then moves to position C to provide for He chase gas to push an amount of F-18 enriched H$_2$$^{18}$O water through a transfer line 1271 for delivery 1285 to a separate system for synthesizing the radiopharmaceutical. The He pressure may be, for example about 80 psi, but may vary.

It may be appreciated that using the described system, the cyclotron beam may be run continuously. Different concentration levels of F-18 may be obtained by exposing the portion of H$_2$$^{18}$O in the target cell 130 for varying amounts of time. As a result, preparation of different doses of radiopharmaceutical may begin with the irradiation process, and may require less complicated dilutions during the synthesis process.

The system may also include a reprocessing line 1290 that recycles and returns H$_2$$^{18}$O to vessel 1205 for reuse. The system may use electrochemical components to separate, clean, and pump H$_2$$^{18}$O back to the vessel 1205.

The flow through radiation detector 1265 may use, for example, a CZT sensor, as described below.

CZT

Figure 13:
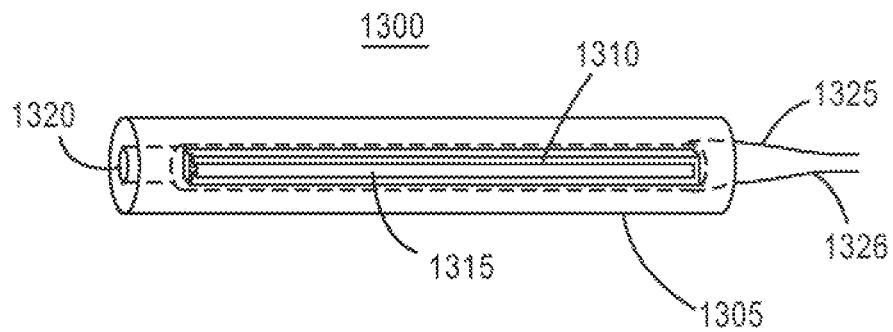
FIGS. 13-20 and 21A-21C illustrate examples of activity and/or volume sensors in accordance with aspects presented herein.

FIG. 13 shows a schematic illustration of a gamma ray collimated detector 1300. The sensor 1300 may include a cadmium zinc telluride (CdZnTe, or CZT) element 1310, however, other solid state materials currently available or yet to be discovered may be used. CZT is a direct bandgap semiconductor and can operate in a direct-conversion (e.g., photoconductive) mode at room temperature, unlike some other materials (particularly germanium) which may require cooling, in some cases, to liquid nitrogen temperature. The relative advantages of CZT over germanium or other detectors include a high sensitivity for x-rays and gamma-rays, due to the high atomic numbers and masses of Cd and Te relative to other detector materials currently in use, and better energy resolution than scintillator detectors. A gamma ray (photon) traversing a CZT element 1310 liberates electron-hole pairs in its path. A bias voltage applied across electrodes 1315 and 1316 (not shown in FIG. 13, but both shown in a side view in FIG. 14) on the surface of the element 1310 causes charge to be swept to the electrodes 1315, 1316 on the surface of the CZT (electrons toward an anode, holes toward a cathode). Wires 1325 and 1326 connect, respectively from electrodes 1315 and 1316 to a source of the applied voltage.

The sensor 1300 can function accurately as a spectroscopic gamma energy sensor, particularly when the element 1310 is CZT. However, geometric aspects may be considered. In conventional use of CZT as a gamma ray detector, the CZT element 1310 may be a thin platelet, sometimes arranged in multiples to form arrays for imaging, generally perpendicularly facing the source of gamma ray emission. Therefore, gamma rays of differing energies all traverse a detector element of substantially the same thickness. While absorption of the gamma ray may generally be less than 100% efficient, higher energy gamma rays will liberate more electron-hole pairs than lower energy gamma rays, producing a pulse of greater height. The spectrum and intensity of gamma ray energies may thus be spectroscopically determined by counting the number of pulses generated corresponding to different pulse heights.

Because higher energy photons may travel a greater distance in the CZT rod 1310 before complete absorption, it is advantageous for the CZT rod 1310 to be greater in length in a direction longitudinally (i.e., a long axis) intersecting a known source volume of radionuclide being measured. Gamma rays incident on the CZT rod off or transverse to the long axis may not be fully absorbed, and thus, the CZT rod will not be as sensitive a detector of such gamma rays as a result. Thus, elongating the CZT rod in one direction introduces a degree of collimation and directional sensitivity along the extended direction.

The absorption coefficient for 511 keV gamma ray absorption in CZT is $\mu=0.0153$ cm$^2$/gm. The absorption probability as a function of $\mu$, density $\rho(=5.78$ gm/cm$^3)$ and penetration distance h is $$P(\mu,h)=1-e^{-\mu\rho h}.$$

Therefore, the ratio of absorption in a 10 mm length of CZT to a 1 mm length is $$\frac{P(\mu, 10 \text{ mm})}{P(\mu, 1 \text{ mm})} \sim 9.613.$$

That is, the directional sensitivity for gamma ray detection of CZT at 511 keV along the 10 mm length of the detector is nearly 10 times greater than in the 1 mm thick transverse direction.

Figure 14:
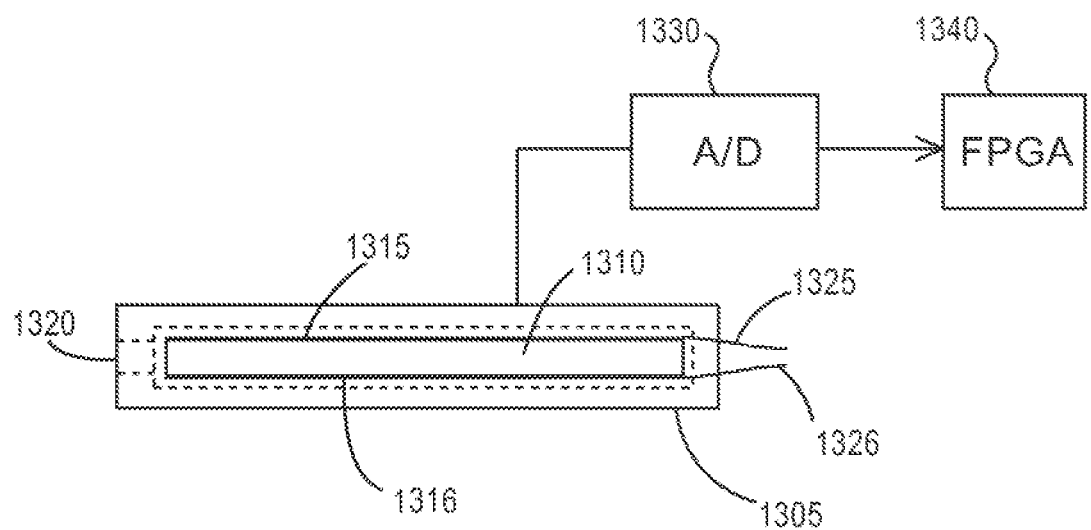

Referring to FIG. 14, the sensor may be a CZT rod 1310 as just described, encased in a shielded case 1305 (e.g., tungsten) with an aperture 1320 open and directed toward the transfer line 1261 to expose the CZT rod 1310 along the long dimension of the rod 1310, while shielding the CZT rod 1310 from gamma rays incident laterally to the long dimension of the rod 1310, e.g., from directions other than along the long dimension. Therefore, the combination of shielding, aperture and extended length of the CZT detector 1300 in direction of gamma ray emission from a portion of the radionuclide sample provides a substantial directional "virtual" collimation of the CZT detector's sensitivity to gamma rays incident from the container in a volume of radionuclide defined by the collimation and the size (e.g., diameter) of the container and the collimation of the acceptance aperture 1320 of the detector 1300. On the basis that the volume of the radionuclide "observable" by the sensor is constant from measurement to measurement, the concentration and total activity of the dose can be determined, after calibration, by the integrated volume of radionuclide that passes through the transfer line 1261. In the case of the present disclosure, by knowing the flow rate and flow aperture, one can calculate the integrated dose on an ongoing basis.

The detector 1300 may also be connected to an Analog-to-Digital (A/D) converter 1330 that separate pulses of radiation so that the relevant radiation can be identified. The A/D converter may separate the pulses into separate energy brackets based on the height of the pulse for each instance of radiation received and the CZT crystal. The A/D converter may then be connected to a processing component 1340 that identifies the amount of activity in the sample based on the amount of relevant pulses identified by the A/D converter. For example, the processing component 1340 may comprise a Field Programmable Gate Array (FPGA) having code instructions setting its state to process the information for the pulses. Using an FPGA enables faster processing speeds than software run via a processor. This enables accurate and timely processing of the pulses measured by the CZT sensor.

Figure 15:
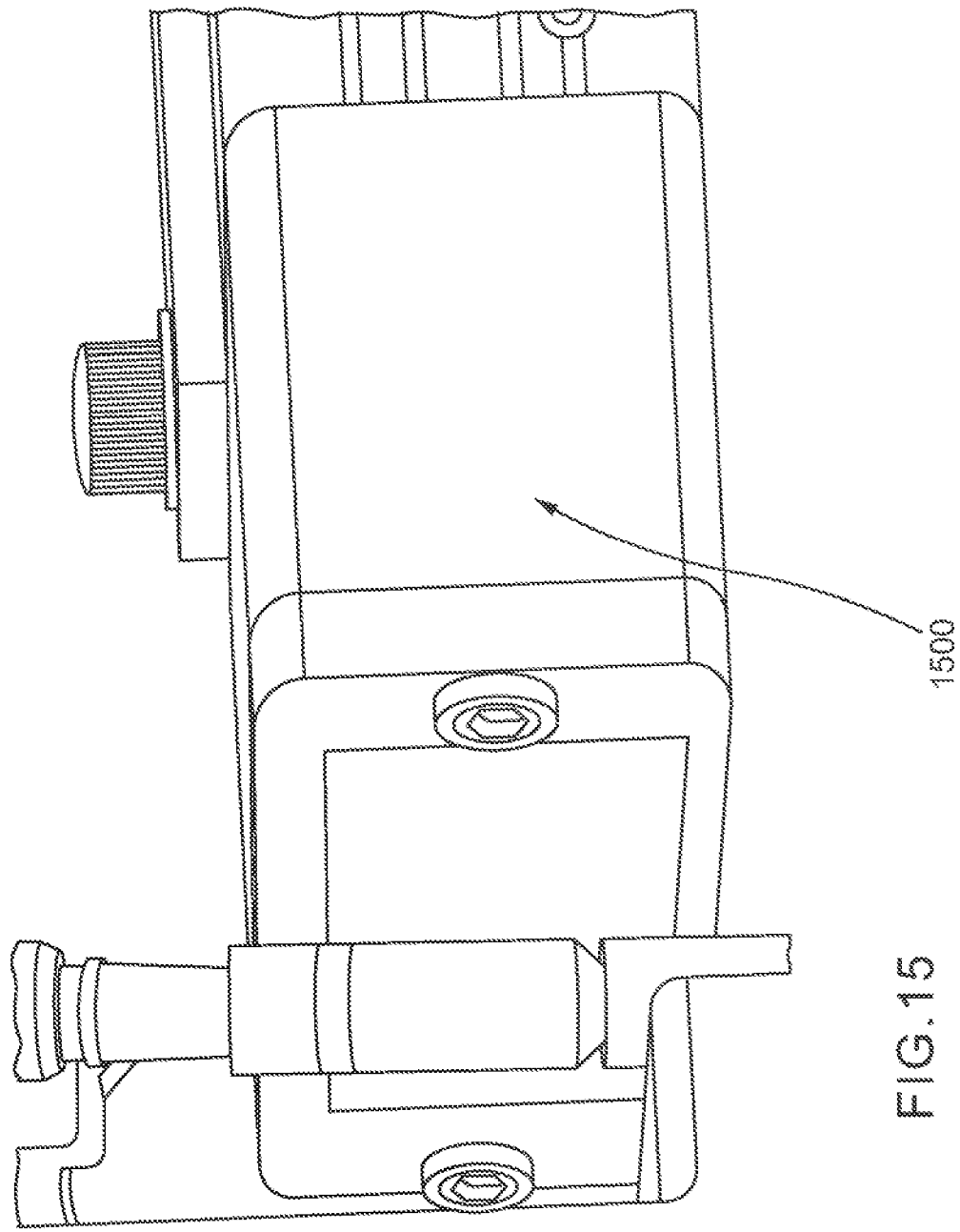

The use of CZT solid state detectors in accordance with aspects presented herein, among other things, may allow stable measurements over time and reduction in handling and environmental (humidity) concerns by removing the need for scintillators. Furthermore, these detector elements may be compact and therefore may be packaged in smaller housings. The stopping power of CZT is also suitable for 511 keV (typical for F-18 emissions, for example) and can withstand exposure to this radiation energy level. CZT sensors may be used in any of the splitter, synthesis modules, HPLC, Low Pressure, flash chromatography or Solid phase extraction module, and in the vial filler subsystems, for example. FIG. 15 shows an example Photostat of such an example CZT sensor in accordance with aspects presented herein.

Figure 16:
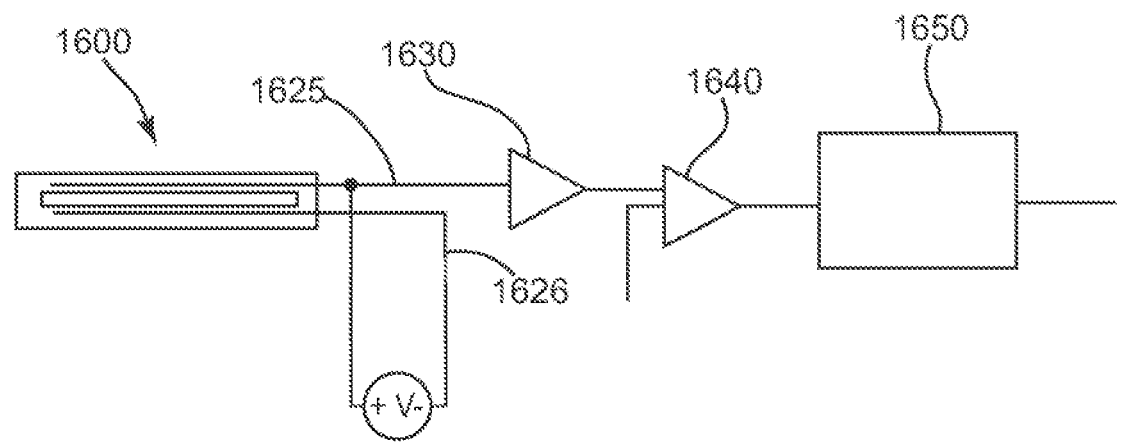

FIG. 16 shows a conceptual circuit diagram for measuring gamma rays with the detector 1600. A charge amplifier 1630 coupled to the electrodes 1615, 1616 amplifies the charge. A pulse generator 1640 converts the sensed charge to a pulse, where the pulse height is proportional to the energy of the gamma ray. A counting circuit 1650 determines the number of pulses as a function of energy.

Concentration-Activity Volume Sensor

One example type of CZT sensor usable, for example, in splitter and vial filler applications in accordance with aspects presented herein is referred to interchangeably herein as a Concentration-Activity-Volume (CAV) sensor. This sensor uses a slender column with two CZT sensors (e.g., which may be collimated) to measure radioactivity, and may also be used to determine volume and concentration of fluid held in the column. In one example such method for measuring volume and concentration, two sensors are oriented in an arrangement such that one sensor is located at or near the top of a vessel containing a volume to be measured, and the other is located at or near the bottom of the container. See FIG. 17, where the elements 1300 $t$ and 1300 $b$, are representative of example CZT crystals usable in a CAV sensor in accordance with aspects presented herein (the actual crystals may be a different shape and aspect ratio as shown in this figure).

Figure 17:
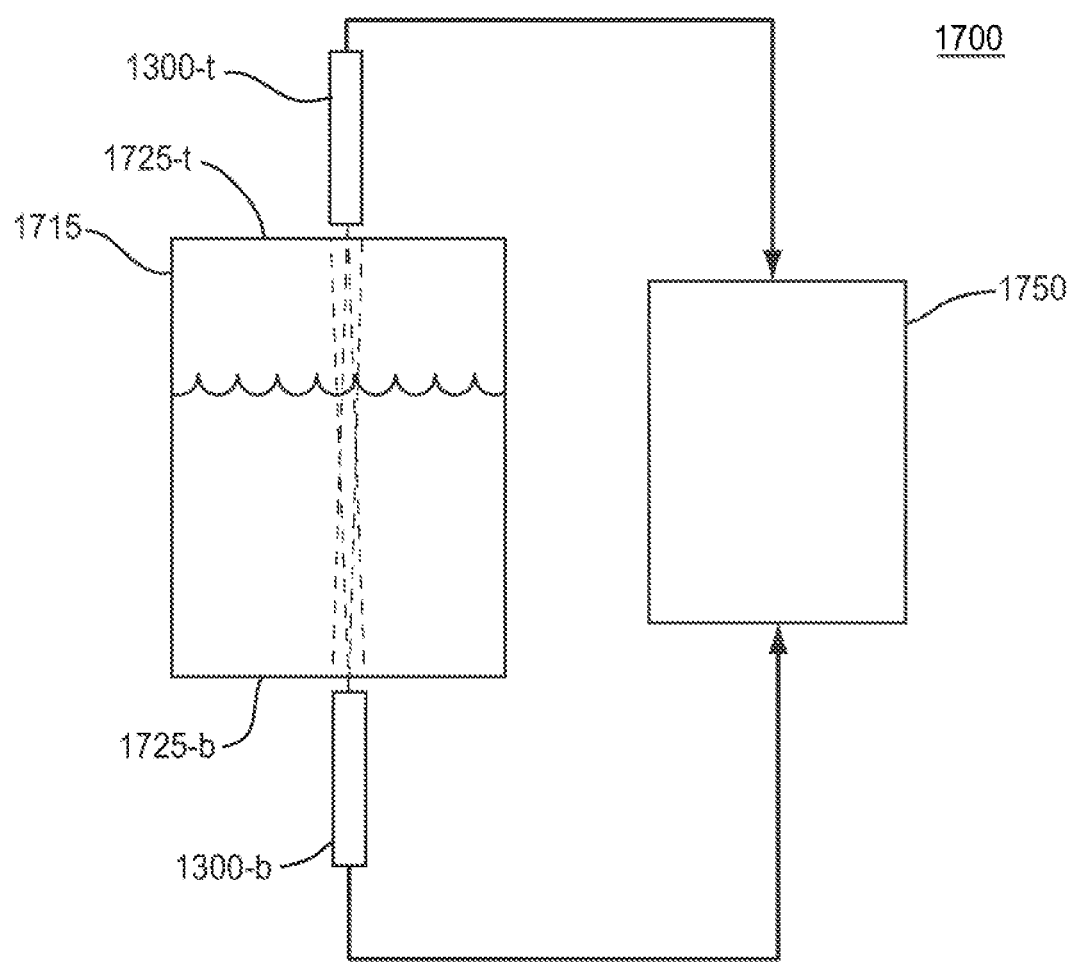

In contrast with some related art devices, CAV sensors in accordance with aspects presented herein do not require a concentration sensor or an optical sensor array to measure volume. As shown in FIG. 17, when the vessel 1715 is full, the two sensors 1300$t$ and 1300$b$ will have nearly equal measurements (in the case where they are both essentially equidistant from the effective center of the radiation). In cases where the fluid volume of the vessel 1715 is less than full, the bottom sensor 1300$b$, as shown in FIG. 17, will have a higher reading than the top sensor 1300$t$. This differential measurement may be used to determine volume information. By removing nonlinearity and subtracting background offsets in the readings, the readings from the two sensors 1300$t$ and 1300$b$ may, for example, be divided to find the volume of the fluid in the column. The total activity may then be found, and therefore the concentration, as well. The vessel has a known inner diameter and is centered with respect to the sensors (which may be mounted accurately in a fixed fashion in the vessel shielding). The vessel, which may be plastic or glass, for example, may be slid into brackets in the shielding to provide a repeatable location. Another advantage of the CAV Sensor method is that it may be less sensitive to air bubbles than a concentration sensor of the related art (which may utilize sensed information at a small cross-section of the fluid, for example).

FIG. 17 is a conceptual illustration of an apparatus 1700 for measuring concentration, activity and content volume in a container 1715 containing a radionuclide such as F-18 in solution or a radiopharmaceutical such as F-18 in FDG using the detector 1300 and circuitry of FIGS. 13-16. The container 1715 may have known dimensions, and therefore is known to be able to hold a specified maximum volume of the radionuclide in a liquid form. A first detector 1300-$b$ may be located opposite a bottom face 1725-$b$ of the container 1715. Similarly, a second detector 1300-$t$ may be located opposite a top face 1725-$t$ of the container, and is similarly configured to detect gamma radiation from the container 1715. The two detectors 1300-$b$, 1300-$t$ may be similar or substantially the same. Preferably, the two detectors are identical. Therefore a description of one sensor is sufficient. Each detector, 1300-$t$, 1300-$b$ is coupled to a differential measurement processing system 1750, shown in greater detail in FIG. 18.

Figure 18:
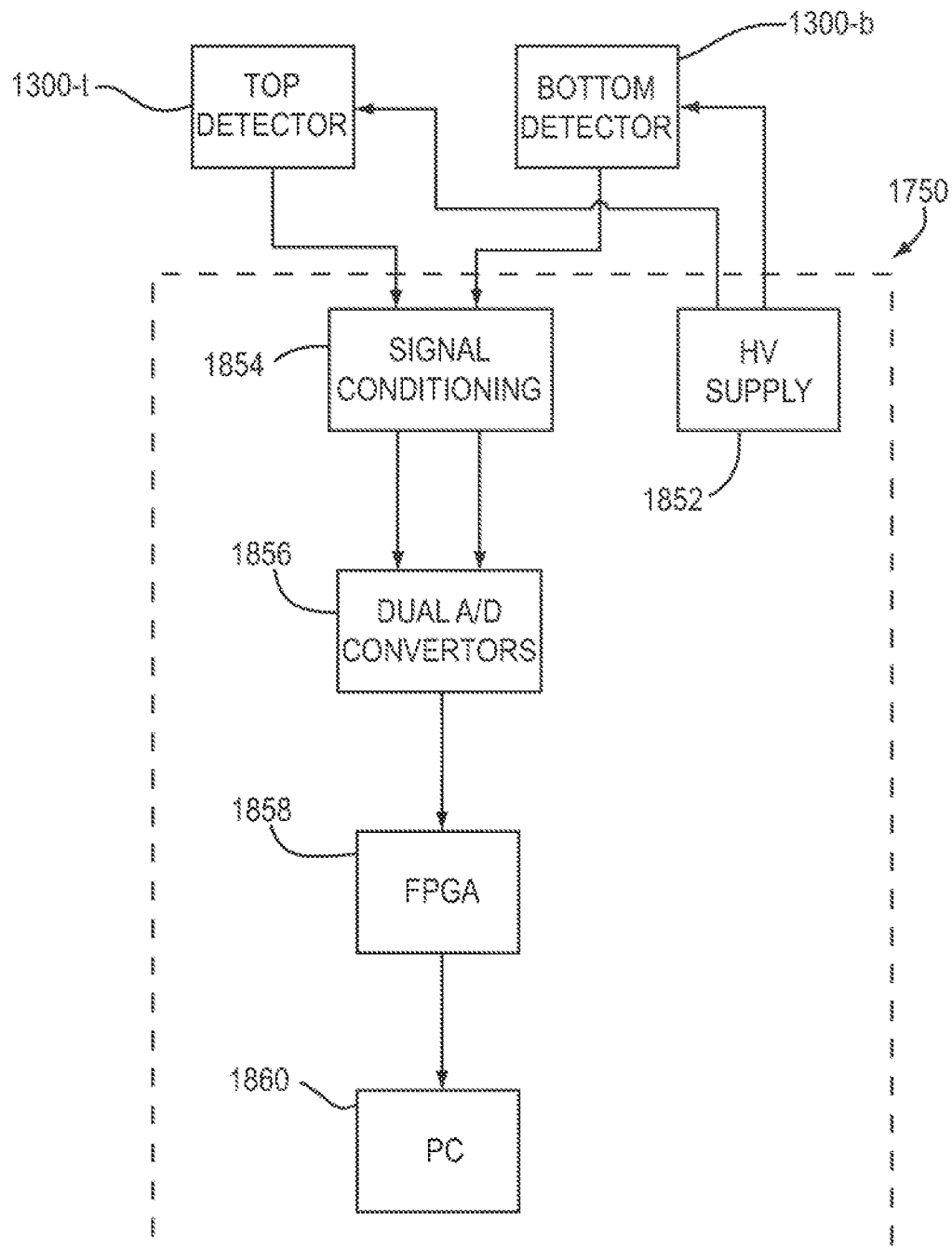

FIG. 18 is a block diagram describing the differential processing system 1750 coupled to the two detectors, 1300-

*t*, **1300-*b*. Processing system 1750 includes a high voltage supply 1852 to provide the bias voltage that operates each of the detectors 1300-*t*, 1300-*b*. Charge output from detectors 1300-*t*, 1300-*b* are separately input (optionally) to signal conditioning circuitry 1852 if noise filtering or DC offset correction, or other artifact removal is warranted. Alternatively, the signals from the detectors 1300-*t*, 1300-*b* may be directly input to a dual channel analog-to-digital converter (ADC) 1856 for processing in digital format by a customized chip, such as a flexible programmable gate array (FPGA) 1858. The function of the FPGA 1858 will be discussed further below. Output of the FPGA 1858 includes at least computed values for the activity sensed by each of the detectors 1300-*t*, 1300-*b* and the volume of radionuclide in liquid accumulated in the container 1715. The output of the FPGA 1858 may be communicated to a computing platform, such as a personal computer (PC) 1860, or other computing controller for purposes of controlling such processes as filling or emptying the container 1715** and identifying parameters associated with the pharmaceutical content for documentation (e.g., date, activity, volume content, labeling, etc.).

The processing system 1750 may be distributed across a network to facilitate, for example, efficient use of computing resources to serve a plurality of detectors 1300 and containers 1715. The division of the processing system 1750 across the network may be selected at any of several points. For example, one or more access nodes (not shown) and network links (not shown) may be placed between the dual channel analog-to-digital converter (ADC) 1856 and the FPGA 1858, in which case the FPGA 1858 and the computing platform PC 1860 may be remotely located across the network. Alternatively, the access nodes and network links may be located between the FPGA 1858 and the PC 1860. It should be understood that other network linking arrangements between the detectors 1300 and computing and control resources may be configured. The PC 1860 may also be a network configured computing resource, which may also be distributed across one or more networks. For example, the computing resource PC 1860 may include a server, memory, and other accessories, also located remotely from each other across the one or more networks to provide the operational control of the plurality of detectors 1300 coupled to respective containers 1715.

Figure 19:
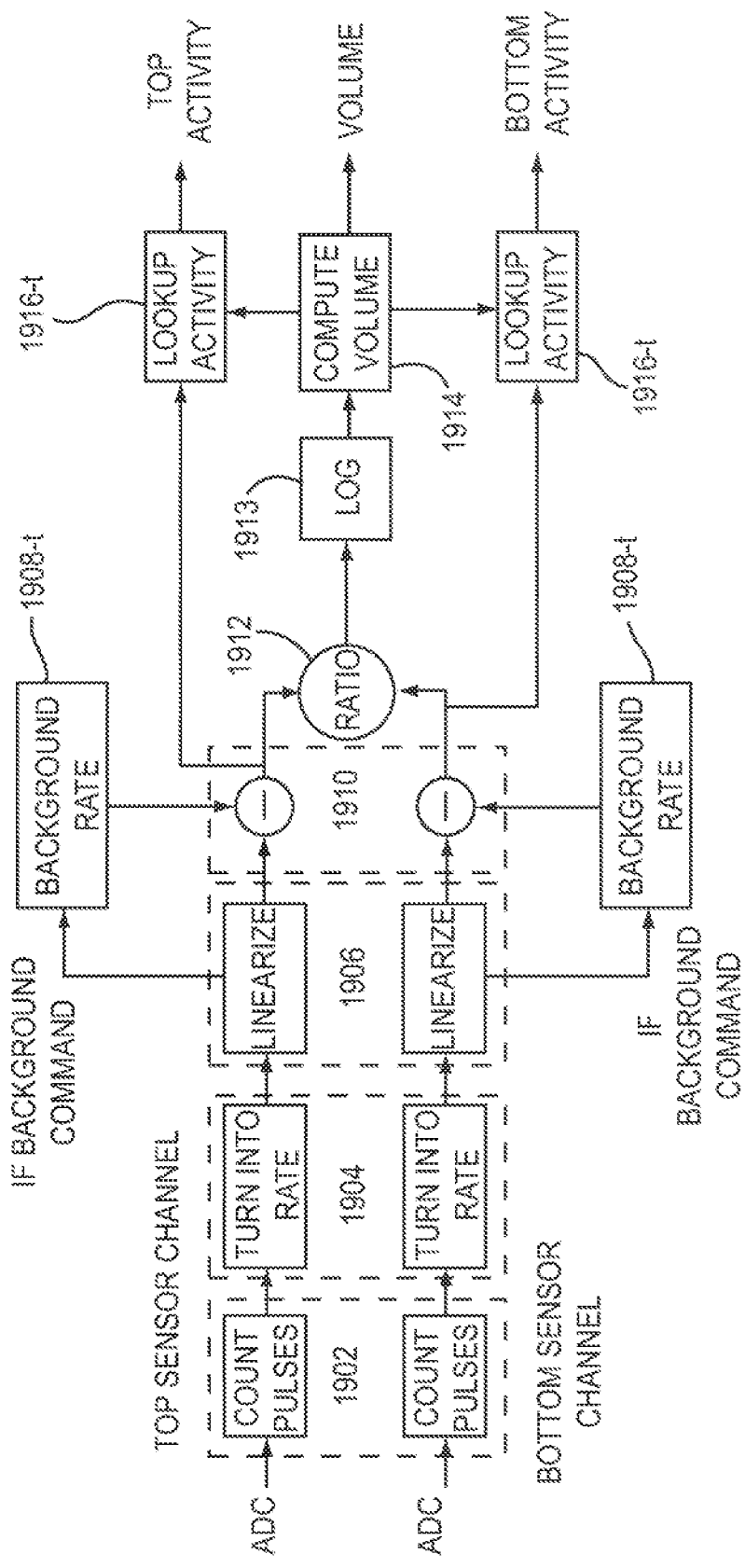

FIG. 19 is a flowchart 1900 describing the functions of components of the FPGA 1858. Digitized data from each channel (i.e., top and bottom) of the ADC 1856 is input to respective counters for pulse counting (process block 1902). In conjunction with a clocking signal from a timing source (not shown) the pulse counts per unit of time (e.g., seconds) are converted to respective count rates (process block 1904).

The count rates are then linearized (in process block 1906 for each respective detector **1300-*t*, 1300-*b***). The linearization process may include statistical or calibration-based correction, for example, when the count rate becomes so high that pulses may overlap, an effect referred to as "pile up."

The measured count rate, as counted by the detector and associated electronics, will become lower than the true count rate at high count rates. This is caused by effects in the bias circuitry, crystal, and the electronics. In the bias circuitry and crystal, a high photon flux can cause a shift in the spectral response (as a decreased photopeak to background ratio) which can cause undercounting. Also, the pulse width (governed by the crystal and preamplifier characteristics) along with the pulse counting electronics can have an impact on linearity. At high count rates, pulses can pile up and double or triple pulses may be combined and counted as one instead of two or three separate pulses respectively. This is exacerbated when the pulse width is increased or the counting electronics is too slow to count fast pulse rates (long retrigger times, etc.).

To linearize the count rate, a nonlinearity calibration is performed, along with implementing a look-up table or nonlinearity correction equation. To perform calibration, a high activity sample (e.g., having a maximum expected activity) is placed in front of each sensor and allowed to decay. Data is then collected over several half-lives until the count rate is low (i.e., in the linear range where no pulse pile up occurs). Curve fitting is then performed (e.g., polynomial, Lambert-W, etc.) to describe the relationship between true count rate and the measured count rate. Once established, the curve for each sensor (detector and electronics) can be used in a look-up table or equation-based correction to linearize measurements made.

Accordingly, a correction may be applied on a calibration basis to correct for an undercounting of pulses due to pulse overlap. If a background count has been detected (such as, for example, before the container is filled), a command may be issued for each detector rate to read the background rate (in process blocks **1908-*t*, 1908-*b*, whether from a look-up table, a previous reading from the detectors prior to filling the container, etc.). The background rates are subtracted (in process blocks 1910-*t* and 1910-*b***) from the respective linearized count rates.

The ratio of the resulting "adjusted" counting rates is computed (in process block 1912) and the logarithm of the ratio is computed (in process block 1913) which, as it happens is approximately linear in proportion to the fill level of the container 1715. In one embodiment, the log ratio measurement may be referred to a lookup table to compute the fill volume of the container (as in process block 1914). The fill volume depends on a known value of the shape, cross-section and height of the container 1715. The adjusted count rate for each detector is compared with the computed volume to determine the lookup activity (in process blocks **1916-*t* and 1916-*b*) for each respective detector 1300-*t*, 1300-*b*. The outputs to the PC 1860** include the top activity level, bottom activity level, and container volume.

Figure 20:
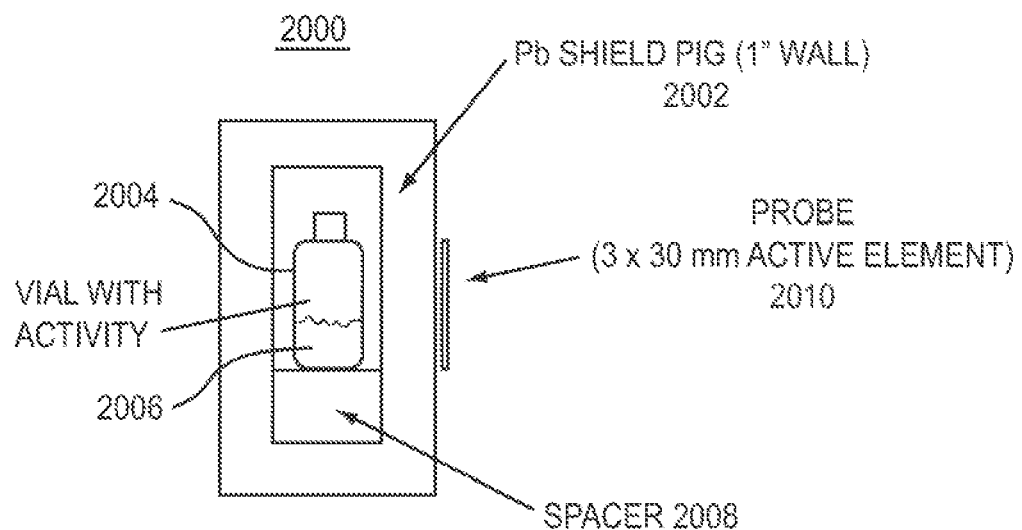

FIG. 20 illustrates another example sensor that may be used to measure activity. FIG. 20 illustrates a system 2000 having a cavity 2002 into which a vessel 2004 is received in order to measure the activity of material 2004 within the vessel. As with the other sensors, this sensor may be provided in connection with any of a splitter, a synthesis unit, a vial filler, a quality control component, and other components described herein. The cavity 2002 may be a lead shield, such as a pig having a 1" wall. A probe 2010 is placed adjacent the cavity 2002 and is configured to measure the activity of the material within the cavity. A spacer 2008 may be provided within the cavity in order to maintain the vessel 2004 at an appropriate height relative to probe 2010. Probe 2010 may comprise a CAT type sensor, as described above. Probe 2010 may comprise a diode detector, such as a pin diode detector placed at the side of vessel 2004.

FIGS. 21*a-c* illustrate a system 2100 for measuring both activity and volume of a sample 2106 within vessel 2104. The system includes a shield 2102 that surrounds a vessel 2104, similar to that illustrated in FIG. 20. In both FIG. 20 and FIG. 21, the vessel may be physically isolated from the shield. A sensor 2110 is provided adjacent to the shield, e.g., at a side of vessel 2104 in order to measure the activity of the material 2106 within the vessel 2104. The sensor may be similar to that described in connection with FIG. 20. Additionally, the system enables a volume measurement of material 2106 in a vessel 2104 via strain gauge 2112 or similar equipment. The shield comprises an opening into which the vessel is received. The vessel may comprise an easy extraction vial having a tapered portion 2107. The opening 2103 extends through the bottom of the shield 2102, as illustrated in FIG. 21b such that the vessel can extend through the bottom opening in order to contact strain gauge 2112. FIG. 21c illustrates a cross section of the system, illustrating the opening 2103 in shield 2102 that enables the vessel 2104 to contact a sensor 2114 comprised in strain gauge 2112. The vessel rests on the strain gauge sensor 2114. A processor 2116 may interpret the measured strain in order to interpret a weight of the vessel 2104. As the vessel fills, the strain will increase, and the strain gauge will determine the corresponding increase in volume of the material 2106 within the vessel 2104. This system 2100 enables the activity to be measured via sensor 2110 at the same time that the volume is measured via strain gauge 2112.

Another way in which volume may be measured is to provide a metering pump, such as a stepper motor controlled pump. This type of pump enables a known volume to be measured per predetermined number of pumps. Thus, based on the number of pumps applied, the corresponding volume may be determined.

Drying Process and Subsystem

Aspects of the present relation relate to methods and compositions for drying radioisotope solutions and for reducing synthesizing time of radioisotopes. The solution exiting the cyclotron may include a small fraction by volume of radioisotope (e.g., about 1% by volume) and a large fraction of O-18 enriched water (e.g., 99% by volume).

An aspect includes a method of drying a radioisotope solution having radioisotopes, the method including: 1) passing the radioisotope solution through a solid phase extraction column containing an anion exchange group, thereby trapping the radioisotopes in the column; and 2) passing an eluent through the column, thereby removing the radioisotopes from the column, wherein the eluent includes a cation trapping molecule and less than 5% water.

Another aspect includes an eluent composition for drying a radioisotope solution having radioisotopes, the composition including of a cation trapping molecule, a salt, less than 5% water, and the remainder solvent.

Additional steps for further increasing the water removal may include flushing the column with an organic solvent before passing the eluent through the column, and/or flushing the column with a high pressure inert dry gas after the organic solvent flush, but before passing the eluent through the column.

In one example implementation in accordance with aspects presented herein, the radioisotope is F-18, the extraction column is a quaternary methylammonium (QMA) column, the cation trapping molecule is 10-diaza-4,7,13,16, 21,24-hexaoxabicyclo[8.8.8]hexacosane (Kryptofix 222), the salt is potassium carbonate $K_2CO_3$, the solvent is acetonitrile, and the water content is less than 1%. The organic solvent in the additional step is acetonitrile and the dry gas in the additional step is nitrogen.

Alternative Deprotection Method and Subsystem

Aspects presented herein include methods and systems for deprotecting labeled compounds, such as halogenated radiopharmaceuticals. One aspect relates to such a method (and a corresponding system for carrying out this method) comprising the steps of: 1) labeling a protected precursor compound with a labeling agent to form a labeled protected compound; 2) contacting the labeled protected compound with a solid support; 3) removing the labeled protected compound from the solid support with a removing agent; and 4) deprotecting the labeled protected compound with a deprotecting agent to form a labeled deprotected compound (final labeled compound).

Another aspect relates to a method (and corresponding system to this method) comprising the steps of: 1) labeling a protected precursor compound with a labeling agent to form a labeled protected compound; 2) contacting the labeled protected compound with a medium containing two or more pieces of solid support; 3) deprotecting the labeled protected compound in the medium with a deprotecting agent to form a labeled deprotected compound; and 4) removing the labeled deprotected compound (final labeled compound) from the solid support with a removing agent.

Splitter

In one example implementation of a system in accordance with aspects presented herein, the splitter is the subsystem that accepts the radioactive output from the cyclotron, determines the fluid volume, total activity, and radioactive concentration of the fluid and then divides the fluid into smaller batches and sends these batches to individual synthesis cassettes. In one example implementation, the splitter has the following characteristics: accepts between 1.5 and 15 ml fluid from one or two cyclotrons; provides filtering for the fluid as it enters the splitter; determines the total activity level of the batch, for activity levels up to 30 Ci; determines the fluid volume of the batch; determines the radioactive concentration of the fluid in the batch; communicates this information to the Blackbird computer system; accepts requests from the control or other computer system for batch sizes and delivery sequence for batches to be delivered to individual synthesis units (the delivery sequence may include between 1 and 24 synthesis units); meters and delivers the batches to individual synthesis units in the sequence requested; and provides for periodic replacement of the fluid lines and the fluid storage vessel.

Additional features and operational procedures may also be included such as: any excess or left over radioactive material in the splitter vessel may be routed to the O-18 recovery tank; periodically, e.g., once per day, the splitter accumulator vessel may be rinsed with acetonitrile and then dried by flowing a dry inert gas through the vessel; periodically, e.g., once per month, the accumulator vessel and the line sets from the splitter to the synthesis cassettes may be replaced; and periodically, e.g., every two months, the line set between the cyclotron and the splitter may be replaced.

Figure 22:
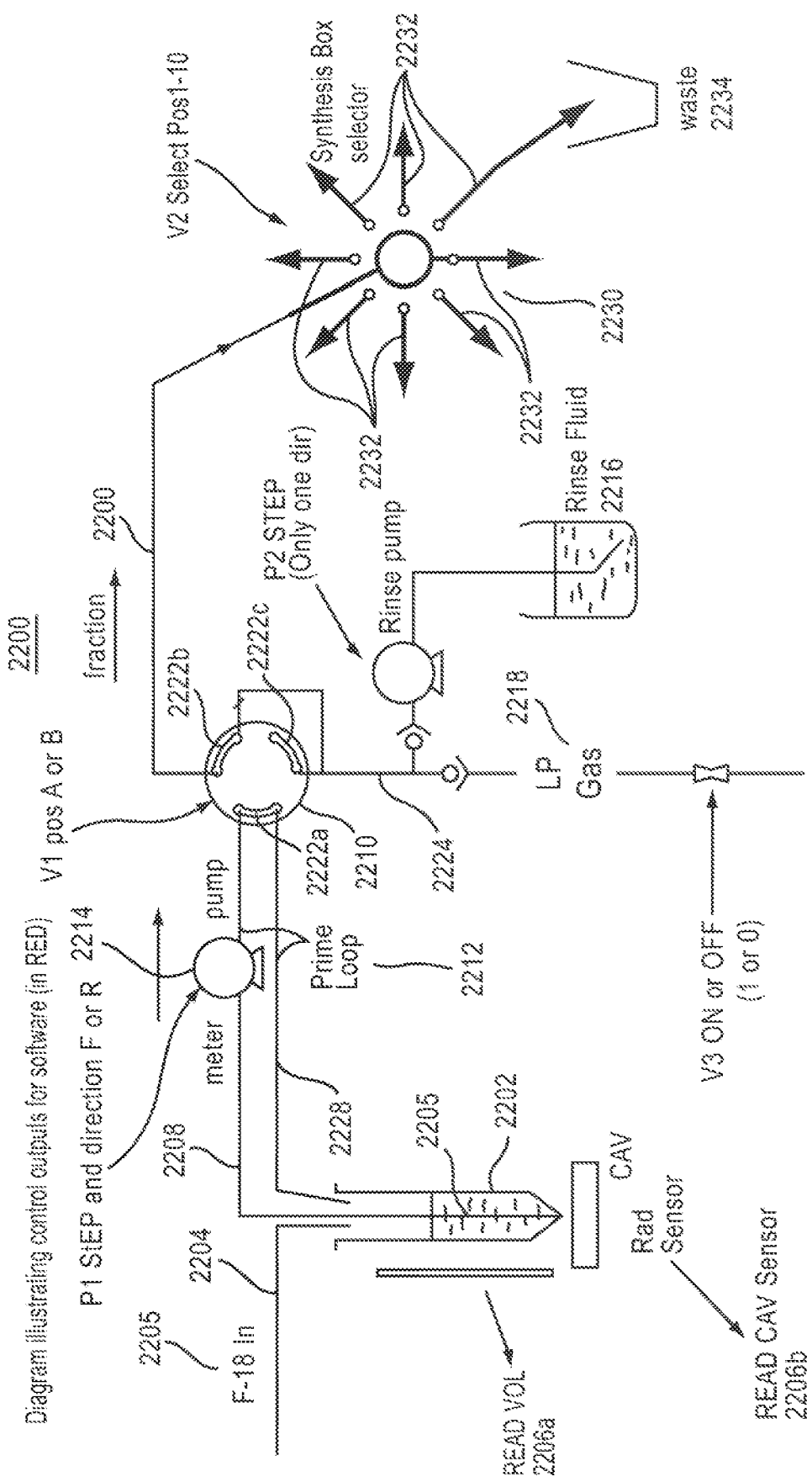

FIG. 22 illustrates an example diagram of a splitter 2200. Splitter 2200 comprises a vessel 2202 with a line 2204 that receives active product 2205 from a radionuclide generator such as a cyclotron (not shown). The splitter 2200 may comprise a sensor for measuring activity and/or volume of the active material 2205 received within vessel 2202, e.g., sensor 2206a, 2206b. Vessel 2202 also comprises a connection 2208 to a pump 2210 for pumping the active product to a synthesis unit (not shown. A prime loop 2212 may be provided that forms a loop between the vessel 2202 and the pump 2210. The prime loop 2212 enables the pump 2210 to be primed so that an accurate amount of active product 2205 can be distributed to the synthesis unit. A meter 2214 may be provided in the line connecting the vessel 2202 to the pump 2210 in order to verify the amount of active product 2205 being pumped. The meter may comprise a step motor controlled pump meter. A rinse fluid source 2216 and a gas source 2218 may also be connected to the pump 2210 via line 2224. Valves 2226a and 2226b may be provided between this line 2224 and the rinse fluid source 2216 and the gas source 2218.

The pump 2210 may comprise a two position pump. In a first position, as illustrated in FIG. 22, the pump connects the prime loop 2212 and connects the rinse fluid 2216 and gas source 2218 to a line 2220 between the pump 2210 and the synthesis unit. This connection occurs via connectors 2222a-c. In a second position, the pump connects a supply line 2208 from the vessel to the line 2220 between the pump and the synthesis unit and connects the rinse fluid source 2216 and the gas source 2218 to a secondary line 2228 of the prime loop that leads from the pump 2210 returning to the vessel 2202. A synthesis box selector 2230 is also illustrated because a plurality of modules and cassettes, each of which can be used separately in the production of a radiopharmaceutical product. Thus, the synthesis box selector 2230 is illustrated having a plurality of lines 2232 extending to each of the plurality of module and cassette combinations and to a waste compartment 2234.

The rinse fluid may be used to alternately rinse the secondary line 2228 of the prime loop 2212 and the line 2220 leading to the synthesis box selector 2230 in order to avoid contamination. As small amounts of active material 2205 may be supplied to the synthesis box selector 2230, and accuracy is very important, the gas source 2218 may be used to send a gas bubble that moves the amount of active product 2205 from the primed pump 2210 through the line 2220 to the synthesis box selector 2230.

Although the synthesis box selector 2230 is illustrated as the intended source, the splitter 2200 illustrated in FIG. 22 may be used to distribute material stored in the vessel to other locations in the lab other than synthesis units. As an example FIG. 22 illustrates that the material stored in the vessel 2202 may be provided to a waste compartment 2234.

Aspects of splitter implementation may also vary. In one example variation, the splitter subsystem may also provide a drying function, to remove water, including the O-18 water, from the fluid before it is metered to individual synthesis cassettes. The drying function is removed from the splitter subsystem in some variations, depending on considerations surrounding the need to provide different chemistries for different product types.

The splitter may contain and then distribute the full radioactive output of one or two cyclotron targets, up to a projected future activity level of 30 Ci, hence heavy shielding (more than 3 inches of lead) may be required for some implementations. In one example variation, the splitter is located at or very near the mini-cells. For example, the splitter subassembly may be located directly on top of a mini-cell. This approach provides several advantages, including the use of the mini-cell as the shielding for one side of the subsystem and the option to route the outlet lines from the splitter directly into one or more of the shielded mini-cells. The location on top of a mini-cell has advantages over mounting locations on the side or back of a mini-cell, but both top and side mounting versions may be used in some variations, such as where a lack of clearance space exists above the mini-cells. Side mounting may possibly involve floor supported side mounting, for example, since the splitter and its required radiation shielding typically are quite heavy.

One of the functions of the splitter subsystem may be to obtain the radioactivity level of the batch as received from the cyclotron and to determine the volume of the fluid. In one variation, the system may provide this information by placing radiation sensors in accordance with aspects presented hereinabove and below the receiver vessel. One example such sensor is a CAV sensor in accordance with aspects presented herein.

One example approach provides the splitting and metering functions via a positive displacement pump that is controlled to sequentially pump the requested volume for an individual batch through a selector valve to one of 12 lines, for example, per the system computer's requests. The pump option selection may be based, for example, on considerations of range of flow rates available and volumetric flow accuracy. After the pump pushes the desired fluid volume into the line, the fluid may be moved to the selected synthesis module by a bolus of inert gas injected behind the fluid, for example. The pump and selector valve may then be ready to deliver the requested volume of fluid to the next synthesis unit in the requested sequence.

An overview of an example splitter, e.g., 110 from FIG. 1, subsystem in accordance with aspects presented herein is shown in FIG. 23. In FIG. 23, because the splitter system 2300 may contain and distribute the radioactive output of one or more cyclotron targets, for example, up to a projected future activity level of 30 Ci, the system 2300 may be provided with a heavy shielding enclosure 2340, composed for example of three inches of lead. The shielding enclosure 2340 may include one or more access means 2344, such as a hinged door or panel, to provide easy and efficient access to the shielded components for removal, replacement, and/or maintenance. For example, the fluid vessel 2202, fluid delivery lines 2204, 2208, 2220, 2224, and 2228 160, fluid evacuation tubes may be replaced periodically, such as once per month.

FIG. 24 illustrates an exemplary splitter system 2410 that may incorporate a CAV sensor assembly 2430, a pump 2450, and a selector valve assembly 2460. The CAV sensor may include a fluid vessel 2410 positioned in a CAV enclosure 2420. The CAV sensor assembly 2430 is an apparatus for measuring various properties of a liquid radionuclide material.

The CAV sensor assembly 2430 may determine the volume, activity and activity concentration of the product received into the fluid vessel 2410. The information from the CAV sensor assembly 2430 may be automatically provided to a control system 150, or the information may be read from the CAV sensor assembly 2430 by a technician, for example, and manually input into the control system 150. The CAV sensor assembly 2430 may determine the activity concentration, activity, and/or volume components of the radioactive product delivered to the fluid vessel 2410. Once the desired parameters have been measured by the CAV sensor assembly 2430, the pump 2450 may be used to draw discrete volumes of the radioactive product from the fluid vessel 2410 to deliver a desired activity.

The CAV enclosure 2420 may be configured to ensure that the fluid vessel 2410 maintains a proper alignment with radiation sensors, which may be used to determine specific properties of a radioactive product delivered into the fluid vessel 2410, such as, for example, a fluid volume, total radioactive activity, and a radioactive concentration of the product.

The splitter system 2400 may receive the radioactive product directly from one or more generation sources, such as a cyclotron(s), for example. A fluid delivery tube may be configured to deliver the radioactive product from the generation source to the fluid vessel 2410. The fluid delivery tube may be configured to pass through a wall of the CAV enclosure.

In accordance with another aspect of the present invention, as shown more particularly in FIG. 24, an inlet/outlet cap 2470 may be provided to mount on the fluid vessel 2410. The inlet/outlet cap 2470 may be connected to the fluid delivery tube 2460 to permit delivery of the radioactive product into the fluid vessel 2410. Simultaneously, a separate fluid evacuation tube 2480 may be connected to the inlet/outlet cap 2470 to permit evacuation of the radioactive product from the fluid vessel 2410. The radioactive product may be pumped out of the fluid vessel 2410 via the fluid evacuation tube 2480 by the pump 2450.

As shown in FIGS. 25A and 25B, the pump 2450 may be a positive displacement pump controlled to pump a requested volume of the radiopharmaceutical product. The pump 2450 may have a body 2510 with an inlet port 2512 and an outlet port 2514 and operated, for example, by a solenoid 2520 connected to the body 2510. Lead wires 2524 may be configured for connecting the pump 2450 to a power source. The pump 2450 may be a self-priming micro-pump, for example, capable of dispensing discrete volumes of the radiopharmaceutical product, such as volumes between 10-60 μl. Check valves (not shown) may be situated at the inlet port 2512 and outlet port 2514 to control the direction of flow. In addition, a diaphragm (not shown) may be provided to isolate the operating mechanism from the flow path between the inlet port 2512 and the outlet port 2514.

As shown in FIG. 25B, the body 2510 may be provided with mounting holes 2530 for mounting the pump 2450 at a location most suitable for operation and/or maintenance. For example, as shown in FIGS. 22-27, the pump 2450 may be mounted to a pump bracket 2440 via the mounting holes 2530 to be situated in the vicinity of the rear of the enclosure 2420.

The pump 2450 may be controlled by a control system 2880 to sequentially pump a requested volume for each individual batch from the fluid vessel 2410, through the evacuation tube 2480, and to the selector valve assembly 2602 via a pump delivery tube 2760. The evacuation tube 2480 is connected to the inlet port 2512 of the pump 2450 and the pump delivery tube 2760 is connected to the outlet port 2514 of the pump 2450. In accordance with yet other aspects presented herein, a fluid flow meter (not shown) and/or filter assembly (not shown) may be provided between the CAV sensor assembly 2610 and the pump 2450 and/or between the pump 2450 and the selector valve assembly 2602.

Figure 27:
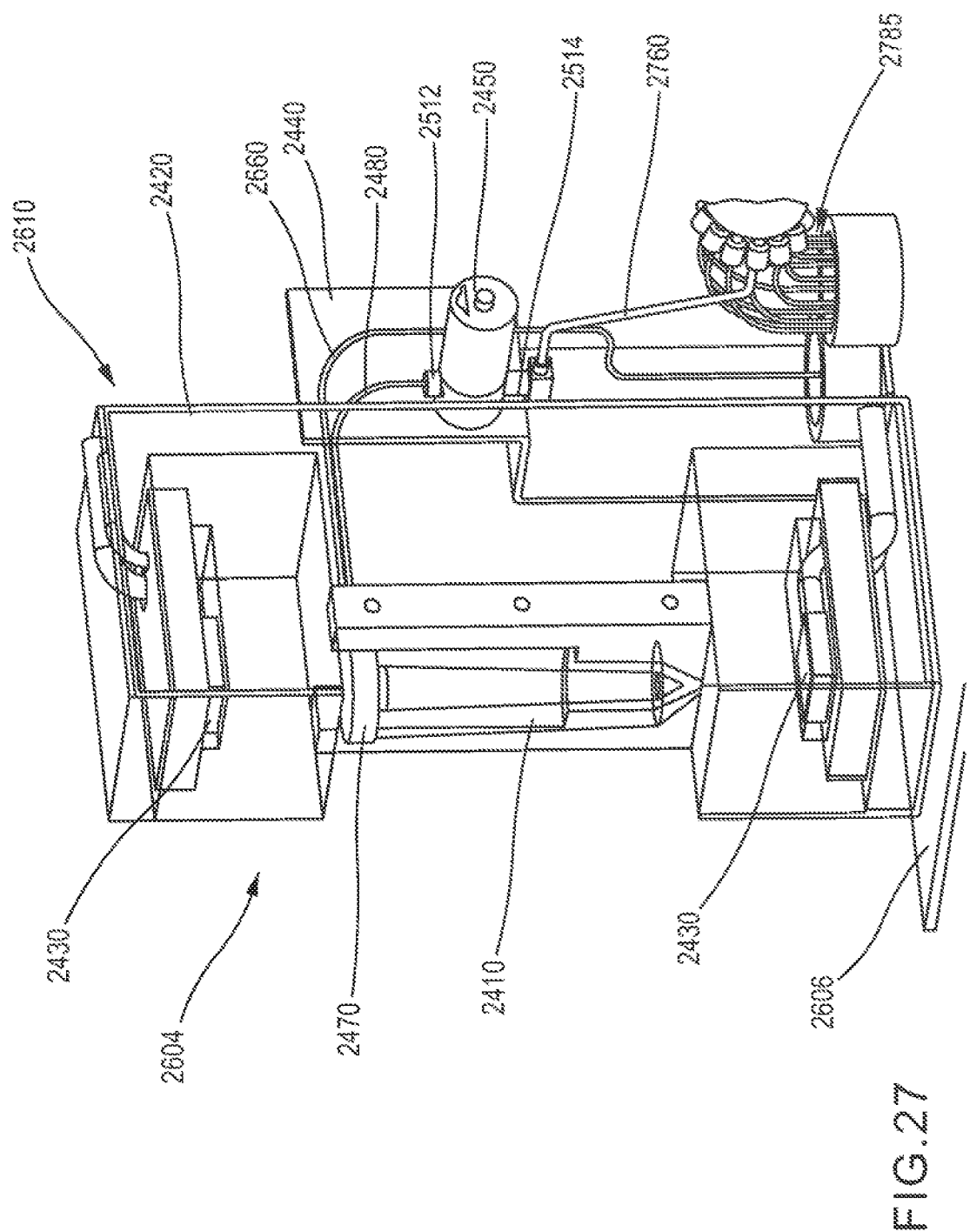

As shown in FIGS. 26 and 27, the selector valve assembly 2602 may include a selector valve 2620 actuated by an actuator 2490, which, for example, may be an electric or pneumatic actuator. The pump delivery tube 2760 provides fluid communication between the pump and an interior chamber of the selector valve 2620. The radioactive product is provided to the CAV sensor assembly 2610 via the fluid delivery tube 2660. The selector valve 2620 may be actuated to send a volume of the radioactive product from the fluid vessel 2410 to any one of as many as twelve lines for delivery to a synthesis unit (not shown).

The splitting and metering functions of the pump 2450 and selector valve assembly 2602 are controlled by the control system to sequentially pump the requested volume for an individual batch through the selector valve 2620 to one of the lines. After the pump 2450 pushes the desired fluid volume into the selected line, the fluid volume is moved to the selected synthesis module by a bolus of inert gas injected behind the fluid. The pump 2450 and selector valve 2620 are then ready to deliver the next requested volume of fluid to the next synthesis unit in the requested sequence.

In accordance with other aspects of the present invention, more than one selector valve assembly 2602 may be provided, if more than twelve lines 2785 are desired for selective delivery of product to additional synthesis units. For example, if the splitter system 2604 is configured with a second selector valve assembly 2602, a 2-way selector valve would be added and the control system configured to direct the pump 2450 output to the desired selector valve assembly 2602.

In accordance with yet other aspects of the present invention, as shown in FIGS. 22-27, the CAV sensor assembly 2610, pump 2450, and the selector valve assembly 2602 may be mounted to a mounting platform 2606. For example, the CAV sensor assembly 2610 may be mounted to the mounting platform 2606 via the CAV enclosure 2420, the pump 2450 via the pump bracket 2440, and the selector valve assembly 2602 via a selector valve bracket 2680.

For example, the pump may comprise a BIO-CHEM Micro-Pump 120 SP Series. The synthesis unit selector may comprise a VALCO A3CSD12MWE 12-Position Flowpath Selector, and the splitter may further comprise a pneumatic actuator such as a VICI A123 Air Actuator.

As shown in FIG. 3, the splitter system 310 may be incorporated into a system that includes a mini-cell assembly 300. Because of the weight of the shielding enclosure for the minicell, the splitter system may be provided directly on an upper surface of the mini-cell assembly 300. Because the mini-cell assembly 300 is also shielded, one side of the shielding enclosure for the splitter 310, such as the lower side, may be shielded via the shielding of the mini-cell assembly 300. In addition, the outlet lines of the splitter system may be routed directly into the shielded mini-cell assembly 300. If a lack of clearance above the mini-cell assembly necessitates a location of the splitter system to a side or rear of the mini-cell assembly, a floor support structure (not shown) may be required to support the heavy load of the splitter system 310 due to radiation shielding.

Figure 28:
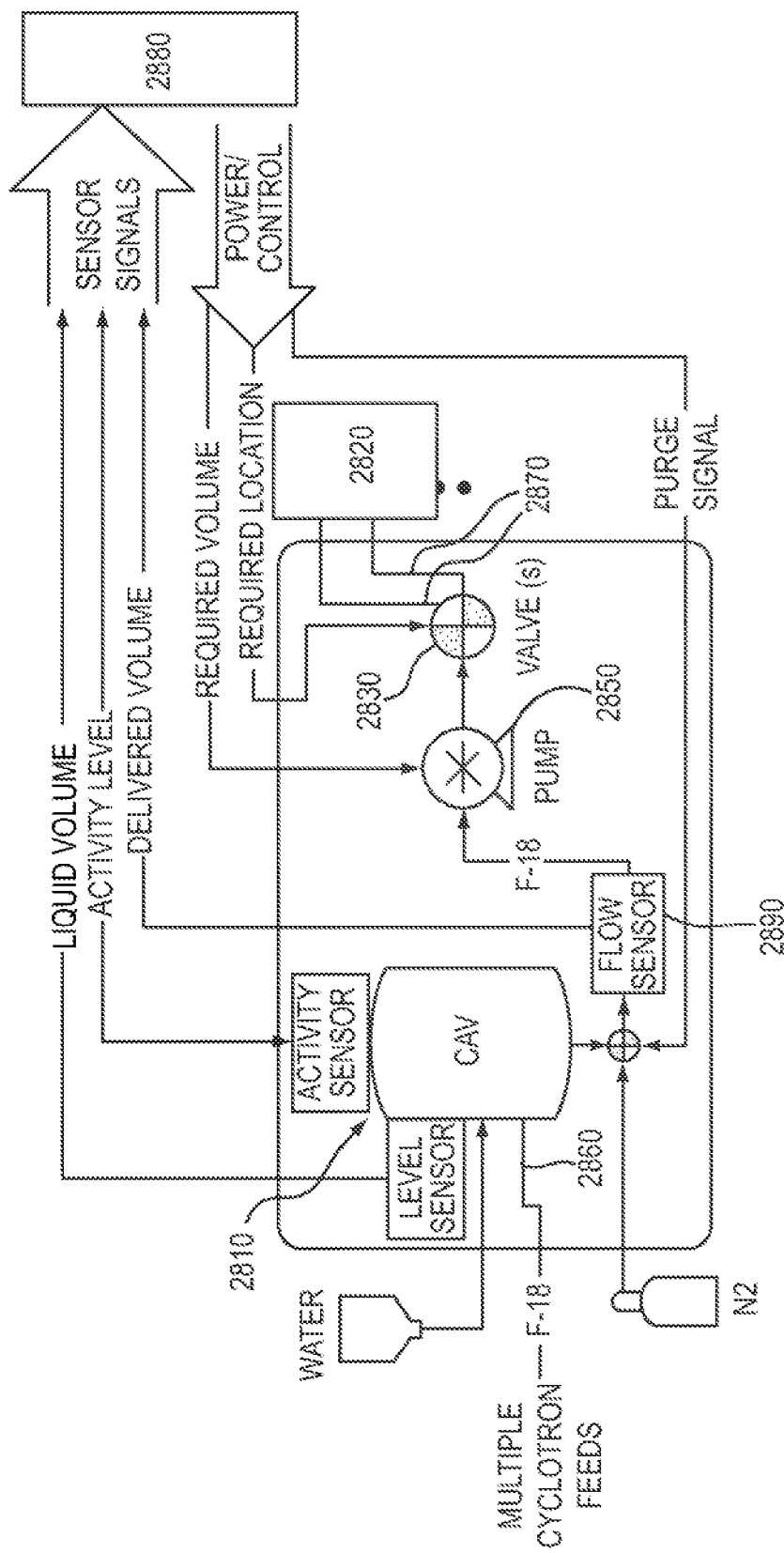

FIG. 28 is a functional flow diagram of the splitter system 110. Production of a radioisotope, such as fluorine-18, for use in the radiopharmaceutical occurs via the cyclotron (not shown), and the radioactive product is provided to the CAV sensor assembly 2810 via the fluid delivery tube 2860. The CAV sensor assembly 2810 determines certain product properties, such as the liquid volume and activity level of the delivered product and activity concentration, and provides the information to the control system 2880 so that the required volume required to achieve a desired activity for delivery to a specific location (e.g., a synthesis module) can be computed and drawn. Accordingly, the control system 2880, in response to inputs from a user, for example, subsequently calculates the required volume of the product to be delivered to a specific location, such as a specific synthesis unit in the mini-cell assembly 2820. The pump 2850 is controlled to pull the required volume for delivery to the required location via the selector valve assembly 2830. A flow sensor 2890 may be provided to record the volume delivered to the pump 2850. The control system 2880 provides a signal to the selector valve assembly 2830 to actuate the valve selector to open communication through one of the lines 2870 in accordance with the required location. A purge signal may be sent from the control system 2880 to provide a volume of purge gas, such as nitrogen, to clear the lines and force the radioactive product out of the line 2870 into the required location. The control system 2880 may then perform the above sequence until each of the required volumes is delivered to each of the required locations.

The subsystem illustrated in FIG. 23 may include one 12-way selector valve, for example. This arrangement is suitable, for example, for an installation with a dual minicell configuration (two mini-cells containing up to six synthesis modules each). For installations with four mini-cells, another 12-way selector valve may be installed, and a 2-way selector may be added to direct the pump output to the desired 12-way selector.

The splitter subsystem may optionally incorporate panels that may be removed to provide access to the fluid vessel and the fluid lines for periodic replacement. The fluid vessel may be positioned in a fixture that maintains proper alignment with the radiation sensors after vessel replacement, for example.

User Interface

Figure 29:
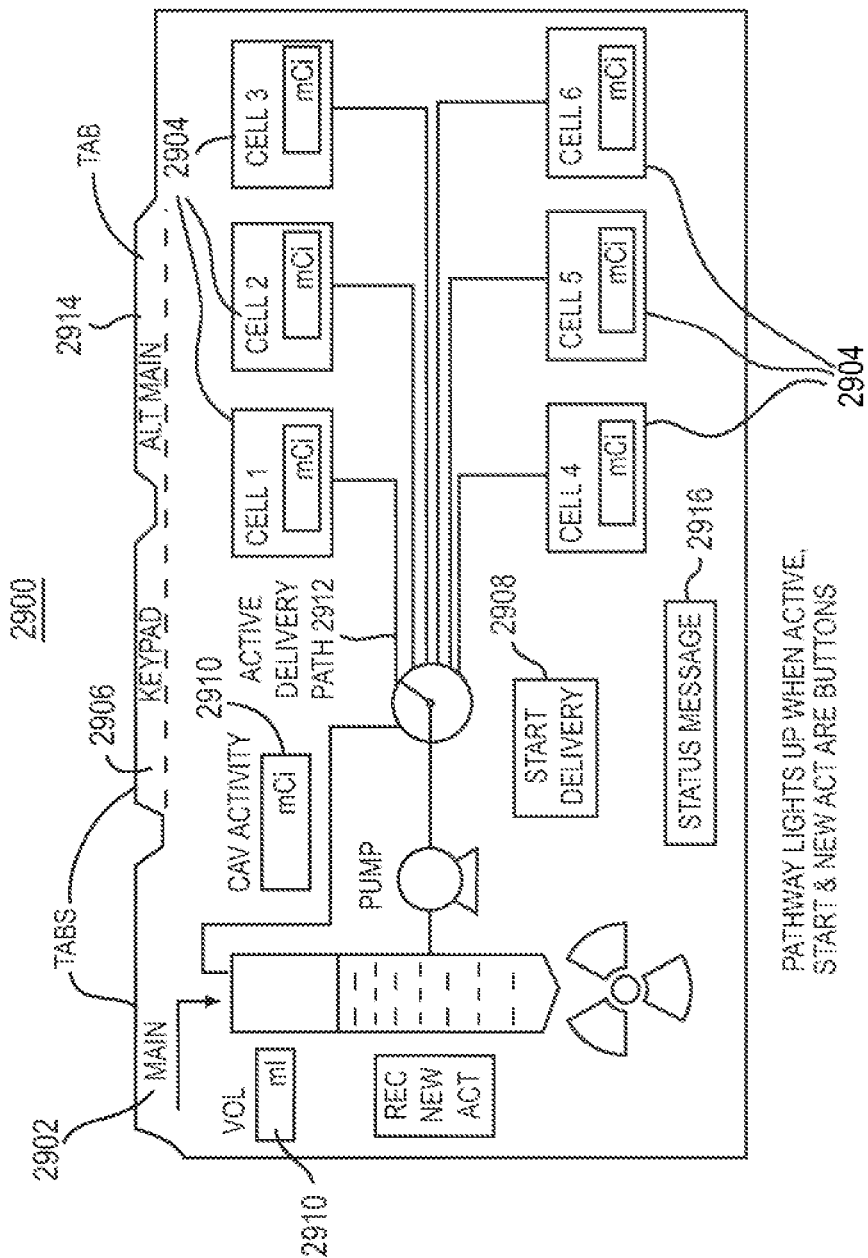
FIG. 29 illustrates an example user interface in accordance with aspects presented herein.

FIG. 29 illustrates an example user interface 2900 for entering instructions into the system. The user interface may be provided at the location of the splitter 110 and/or minicell 115. The user interface comprises a main tab 2902 that receives a selection of a cell 2904. Once a cell is selected, the tab switches to the keypad tab 2906 that provides a keypad for receiving a type and amount of radiopharmaceutical product to be produced. The screen then returns to the main tab 2902 and is able to receive the selection of an additional cell. Once the user has finished entering instructions, the user interface is configured to start production upon receiving a start delivery command 2908. The user interface may further comprise graphics 2910 that illustrate a volume and activity amount for the active product. The user interface may further illustrate a connection 2912 between the splitter and a selected cell in order to show a user the cells currently being used. For example, a pathway may light up when active. A third tab 2914 provides options for maintenance and rinsing features.

The user interface 2900 provides visualization of the process and will graphically depict the status of the system. The user interface provides a simple graphical interface for batch operation as well as have additional screens that depict a more in depth view of the process for diagnostics and troubleshooting. The status 2916 of devices, such as the positions of valves and actuators, may be color coded for easy recognition. Process variables and alarm status may be easily accessible and viewable by the operator.

Valveless Pressure Pumps

Aspects presented herein include valveless pressure pump features, such as for: 1) membrane pumping (also referred to herein as reverse side pumping); and 2) cascade pumping.

Membrane Pumping

In applications where a fluid must be transferred between a plurality of chambers, there are typically losses of fluid that tends to remain inside valve materials, in crevices, or other geometrical features of the valve materials. In addition, in order to perform fluid transfer, relatively complex equipments including pumps and valves that take up large spaces are generally needed. Accordingly, there is a need in the art to provide systems and methods that can ensure pumping operations taking place entirely within a disposable cassette so that, for example, durable components are not contaminated by, nor contaminate, the working fluid, and to ensure fluid transfer from one chamber to the next without fluid loss.

In light of the above described problems and unmet needs, systems and methods according to aspects of the present invention provide a container with one or more fluid passageways having highly isolated and pressure-resistant valves using an actuated membrane. According to various aspects, the container may be a substantially three-dimensional container having two elongated dimensions and a thin third dimension so as to have two main faces formed by the two elongated dimensions. According to an aspect, the fluid passageways may be located closer to one side of the container, and the pressure-resistant valves may be located on an opposite side of the container from the fluid passageways. The fluid passageways and valves may be interconnected with open holes, or scoops, located throughout the container.

Aspects presented herein include a compact modular cassette system and method for the synthesis of radiopharmaceutical products that includes a modular unit having reagent modules and a reaction cassette, the reaction cassette having an actuated flexible membrane placed over valve features formed by open holes or scoops on a side of the cassette and at desired locations of the cassette. The actuated membrane may be disposed on an opposite side of the cassette from the cassette side that is in contact with other modules and that contain one or more fluidic channels and passageways. When a portion of the membrane that is located over a scoop is actuated, the membrane portion may be either urged against the scoop, or pulled away from the scoop. When the membrane portion is urged against a scoop of the fluid passageways, for example, the membrane portion may seal tightly against the scoop of the passageway, thus blocking any ingress or egress of fluid. Alternatively, when the membrane portion is urged away from the scoop of the fluid passageway, then a suction or pumping action may take place. As a result, any fluid present in one or more passageways connected, and in proximity, to the pumping scoop may be urged inside the one or more passageways as a result of the pumping action created by the membrane portion on the pumping scoop.

Figure 30:
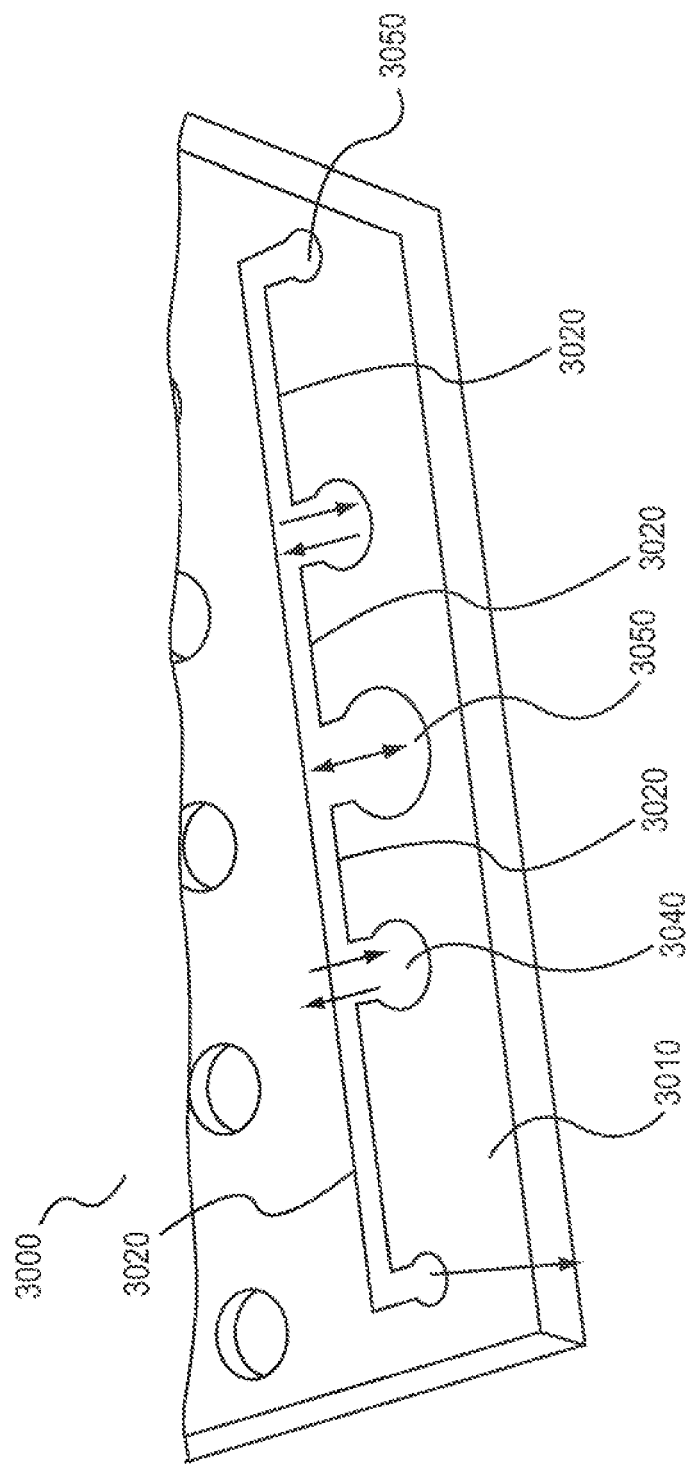
FIG. 30 contains a Photostat of example pump detail in accordance with aspects of the present invention.

Smaller open holes or scoops, to be used as valves, may be located on one or more sides of a central scoop along the path of a fluid passageway, the smaller scoops being usable as valving scoops. Accordingly, when a portion of the membrane alternatively seals against, or pulls away from, one or more of the valving scoops in conjunction with another membrane portion operating a pumping action, as discussed above on the larger pumping scoop, the direction of movement of the fluid inside the one or more passageways connected to the pumping scoop and to the one or more valving scoops may be controlled. Accordingly, fluid flow may be created, controlled and monitored using the flexible membrane being actuated over the pumping scoop and one or more valving scoops, to form a membrane pumping system. FIG. 30 contains a Photostat of an example pump detail in accordance with aspects presented herein, including "opposite side" geometry with arrows indicating flow direction. FIG. 30 is a schematic illustration of a membrane pumping system that may be used in a reaction module or cassette, according to various aspects of the current invention. In FIG. 30, the system 3000 includes a fluidic cassette 3010, which may be a reaction module, that includes a plurality of etched, molded, machined, or otherwise formed passageways 3020, formed inside the cassette 3010. The reaction cassette 3010 may be a substantially three-dimensional module with two opposite surfaces and a thin third dimension. The passageways 3020 may be formed within the module 3020 but may also open on a surface of the cassette 3010 at open holes 3030, and scoops 3040 and/or 3050, which may all have the same size, or may have different sizes. The arrows illustrated in FIG. 30 indicate the flow path of fluid inside the cassette 3010. It should be noted that the fluid passageways 3020 may be formed on only one side, or on both sides, of the cassette 3010. Although scoops 3030 may be formed on both sides of the cassette 3010, scoops 3040 and 3050 may only be open on a single side of the cassette 3010, e.g., the side that is opposite to the side where the fluid passageways 3020 are formed.

The passageways may be formed closer to one side of the cassette 3010 that may be a side opposite to a side where the scoops 3030, 3040 and 3050 are formed, and because of the location of the fluid passageways 3020, the flow path may primarily take place on the side of the cassette 3010 that is opposite to the side where the scoops 3030, 3040 and 3050 are located. The flow of fluid may be controlled via membrane pumping, as described in greater detail below, where the arrangement of a pumping scoop 3050 and one or more valving scoops 3040 on one or more sides of the pumping scoop 3050, each of the scoops being covered by a portion of the membrane, constitutes a membrane pump that is activated by applying a differential pressure on the portion of the membrane located over one or more of the scoops 3040 and 3050. For example, the portion of the membrane located over the larger pumping scoop 3050 can be urged against the scoop 3050 to seal the pumping scoop 3050 and then pulled back away from the scoop 3050, thus creating a pumping action. The one or more scoops 3040 may be used as valves to allow or deny fluid or gas from entering the fluid passageway and thus control the direction of the flow of fluid located in the cassette 3010. The one or more scoops 3040 may be connected to two fluid passageways that only communicate with each other via the scoop 3040 and that are also connected to the main fluid passageways 3020. Accordingly, when the portion of the membrane that is above a scoop 3040 is pressed against the two passageways, flow of fluid from one passageway to the other is interrupted. As a result, the scoop 3040 may be used as a valve, as discussed in more detail below.

A plurality of such pumping arrangements can be formed on the surface of the cassette 3010, indicating the existence of a plurality of membrane pumps on one or more surfaces of the cassette 3010 that control the flow of fluid in the fluid passageways 3020. Accordingly, when the fluid passageways 3020 connect several modular cassettes, fluid transfer can be performed between the plurality of modular cassettes, where fluid is transferred from the fluid communication channels of one cassette onto fluid communication channels of another channel. It should be noted that although FIG. 30 illustrates a structure with three scoops, one central scoop 3050 that functions as a pump and two scoops 3040 that function as valves, a higher number of scoops may be configured, with various combinations of scoops functioning as pumps and scoops functioning as valves.

Figure 31:
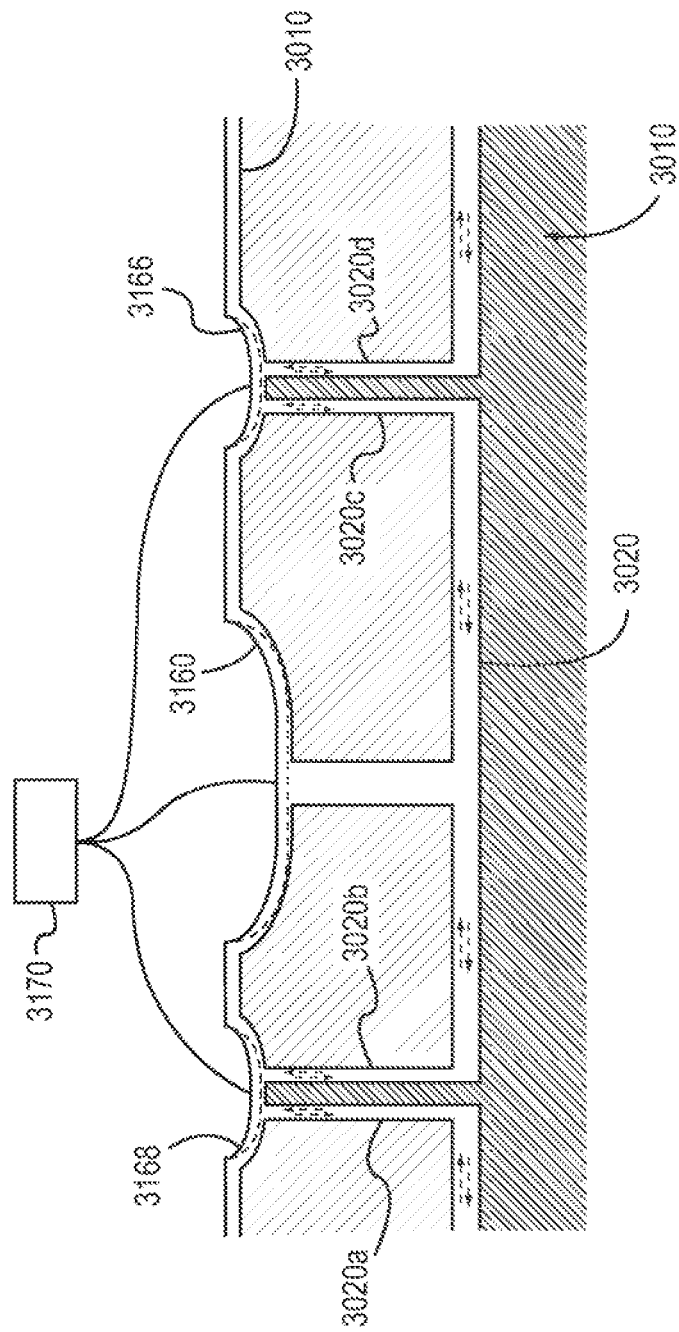
FIGS. 31 and 32 illustrate an example membrane pump in accordance with aspects presented herein.

FIG. 31 is a schematic illustration of a plurality of scoop profiles and an actuatable flexible membrane. In FIG. 31, a membrane portion 3160 covers a portion of the surface of the cassette 3010 where the pumping scoop 3050 is located, and other membrane portions 3166 and 3168 cover other portions of the surface of the cassette 3010 where the valving scoops 3040 are located. The membrane portions 3160, 3166 and 3168 may be controlled by an actuator 3170, which may urge one or more of the membrane portions 3160, 3166 and 3168 independently of each other to seal tightly against the scoops 3040 and/or 3050, or may urge one or more of the membrane portions 3160, 3166 and 3168 independently to pull away from the scoops 3040 and/or 3050 in order to transfer the fluid through the passageways 3020.

In operation, when fluid is present in the passageways 3020, the fluid may be urged in any direction by actuating various portions of the membrane 3160 located at various locations of the surface of the cassette 3010. For example, when the membrane portion 3160 is urged against the pumping scoop 3050 of the fluid passageways 3020, the membrane portion 3160 may seal tightly against the pumping scoop 3050, and another membrane portion 3166 and/or 3168 that is located over one or more of the valving scoops 3040 may or may not be urged against either valving scoop 3040. In FIG. 31, the pumping scoop 13050 covered by a membrane portion 3160 may function as a pump, while the scoops 3040 covered by membrane portions 3166 and 3168 may function as valves.

Valving scoops 3040 may be connected to two fluid passageways 120*a* and 3020*b*, or 3020*c* and 3020*d*, as illustrated in FIG. 31. When a valving scoop 3040 is covered with the membrane portion 3168, the fluid passageways 3020*a* and 3020*b* are formed in the body of the cassette 3010, but only communicate with each other via the scoop 3040. In other words, fluid can only move from passageway 3020*a* to passageway 3020*b*, or vice-versa, via the scoop 3040. The passageways 3020*a* and 3020*b* are also connected to the main fluid passageways 3020 in order to allow fluid to move from the main passageway 3020 into the scoops 3040 and/or 3050 and back to the passageway 3020. Accordingly, when the portion of the membrane that is above a scoop 3040 is pressed tightly against the two passageways 3020*a*/3020*b* or 3020*c*/13020*d*, as illustrated by the dotted line representing the location of the membrane portion 3168 and 3166 pressed immediately over the opening of the passageways 3020*a* and 3020*b*, or over passageways 3020*c* and 3020*d*, flow of fluid from one passageway 3020*a* to the other passageway 3020*b* is interrupted because the fluid can no longer travel from one passageway to the other. As a result, the scoop 3040 may operate as a valve.

Either one of the valving scoops 3040 may be either closed or open. The movement of fluid inside the passageways 3020 may be controlled via the combination of the pumping action of the membrane portion 3060 on the pumping scoop 3050 and the valving action of the valving scoops 3040. The pumping and valving actions created by the membrane portions 3160, 3166 and 3168, create, control, and monitor fluid flow inside the cassette 3010.

Figure 32:
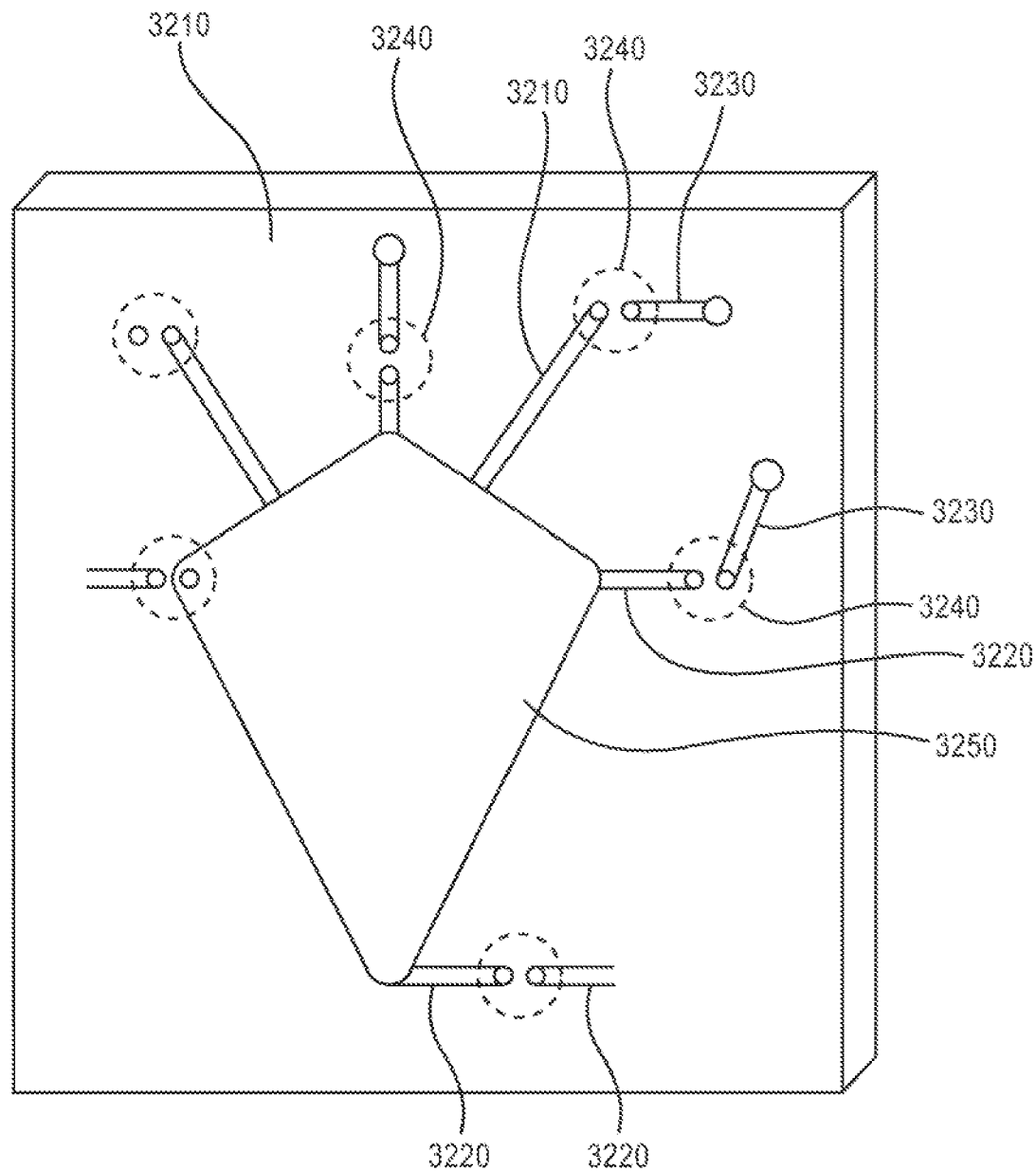

FIG. 32 is a schematic illustration of a reaction cassette that may be used with such a membrane pumping system. In FIG. 32, the reaction cassette 3210 includes a fluid chamber 3250 and fluid communication channels 3220 formed inside the cassette 3210 to transfer fluid in and out of the fluid chamber 3250 during a reaction process. The fluid communication channels 3220 may also be connected to other fluid communication channels 3230 that may be part of another fluid containing chamber within the cassette 3210, or to outside fluid communication channels. The fluid channels 3220 and 3230 may be connected to each other in order to ensure fluid transfer via one or more membrane valves 3240 that are similar to the valving scoops and membrane portion arrangements discussed above. The membrane valve 3240 may include a flexible membrane (not shown) disposed over a scoop (not shown) formed on the surface of the cassette 3210, and may allow, or deny, passage of fluid from a fluid communication channel 3220 to another fluid communication channel 3230 according to the valving mechanism discussed above with respect to FIG. 31.

According to various aspects, the above system and operation, such as the operation of the flexible membrane actuator, can be controlled and operated via hardware and software, as discussed in greater detail below.

Cascade Pumping

According to various aspects presented herein, one or more chambers may be supplied with pneumatic transfer lines or channels connecting the chambers to one another, and allowing the selective flow of pressurized gas and/or the application of a vacuum to the chambers. The channels may connect, for example, a lowest point in a first chamber to a high point in a second chamber in order to ensure that the totality of the fluid present in the first chamber is transferred to the second chamber (e.g., by gravitation). According to various aspects, in order to ensure complete transfer of fluid from a first chamber to a second chamber, a vacuum may be applied to the second chamber, which is the chamber to which the fluid is to be transferred, through, for example, a line communicating the second chamber with a vacuum source, and a flow of pressurized gas may be applied to the first chamber, which is the chamber in which the fluid is located prior to transfer, through, for example, a line communicating the first chamber with a source of pressurized gas. The application of the vacuum to the second chamber and the flow of pressurized gas to the first chamber may be performed contemporaneously. Accordingly, the combined action of the pressurized gas pushing the fluid out of the first chamber, and the vacuum pulling the fluid towards the second chamber, may ensure a more complete and rapid transfer of the fluid from the first chamber to the second chamber.

Figure 33:
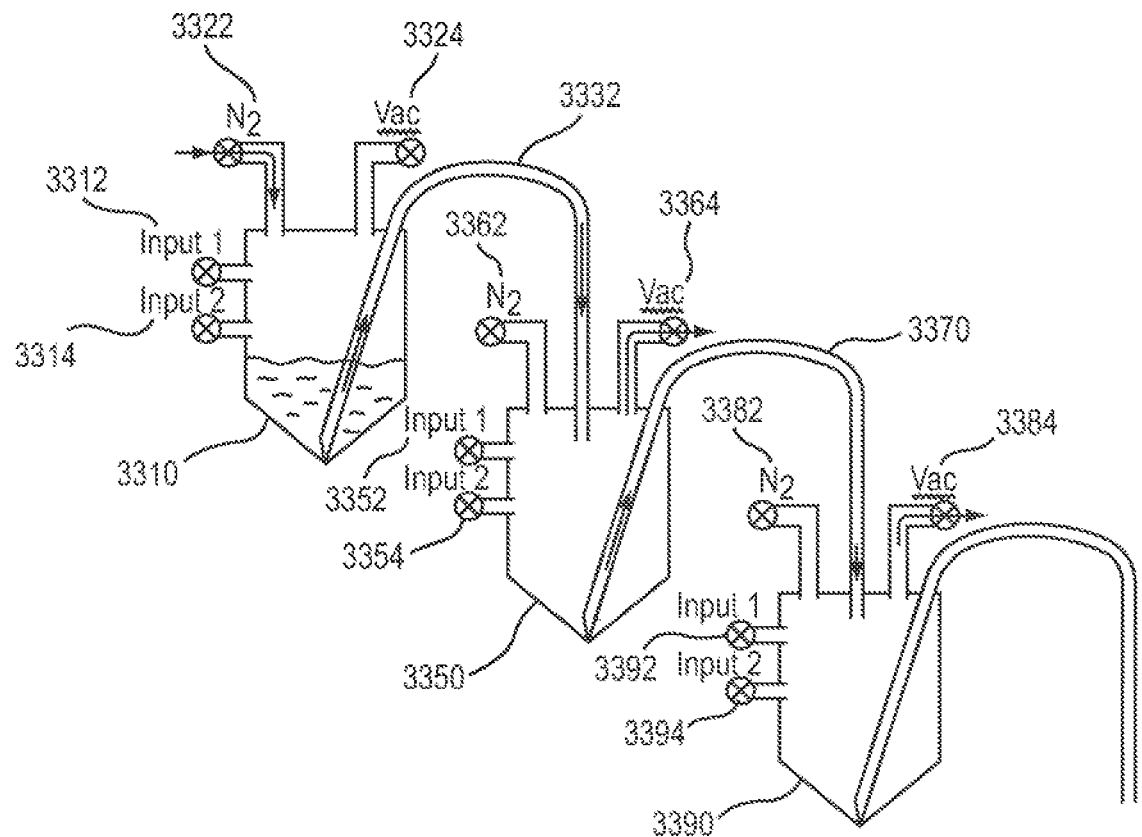
FIG. 33 illustrates an example cascade pump in accordance with aspects presented herein.

FIG. 33 is a schematic illustration of a plurality of mixing chambers 3310, 350 and 190, disposed according to various aspects of the current invention. In FIG. 33, the cavity in each chamber may be large enough to allow a two-phase mixture of liquid and vapor, and to establish a fluid level with the vapor located above the fluid. According to various aspects, each chamber may have one or more entry and exit passages. For example, the chamber 3310 may have input lines 3312 and 3314 to allow for the input of fluids, reagents and other like ingredients, where the chamber 3310 may be a reaction chamber in which various ingredients, solid, liquid, or gaseous, may be input via the input lines 3312 and 3314 and mixed or reacted together. According to various aspects, the line 3322 may be used to provide the chamber 3310 with a pressurized gas such as, for example, $N_2$ by opening a valve at the line 3322. It should be noted that the pressurized gas that flows in the chamber 3310 via the line 3322 may be any combination of gas or gases other than $N_2$, such one or more inert gas, but can also be a gas such as oxygen or air as long as the gas that does not interact with the fluid composition or ingredients present in the chamber 3310 to create an unwanted chemical reaction. It should be noted that a gas referred to as "inert" in this disclosure is inert with respect to the fluid, ingredients or reagents present in the chamber 3310, even if the gas is not inert with respect to other compositions or other compounds.

An exemplary purpose of the pressurized gas provided via the line 3322 to the chamber 3310 is to apply a downward pressure to the fluid present in the chamber 3310 and urge the fluid out of the chamber 3310 to, for example, chamber 3350, via the transfer line 3330. According to various aspects, the chambers 3310, 3350 and 3390 may be configured so as to have an amount of space, or distance, between the vacuum lines 3324, 3364 and 3384 and the free surface of the fluid in order to prevent splashing or splattering from causing fluid to be ingested by the vacuum lines and thus to be lost from the process. For example, vacuum lines may be connected to the chambers from the top of each chamber so that the fluid and the gases in the chamber have enough space to interact without being ingested by the vacuum created in a vacuum line. According to various aspects, baffles may be used to prevent the fluid from being ingested in a vacuum line. The additional amount of space above the free surface of the fluid may also be useful when sparging the fluid to remove any gases dissolved in the fluid.

According to various aspects of the current invention, the end of the transfer line 3330 that is placed inside the chamber 3310 and which may be cut on a bias to have an opening that is non-perpendicular to the axis of the line 3330, may be located at a lowest point of the chamber 3310 in order to ensure that all of the fluid initially located in the chamber 3310 can be transferred to the chamber 3350. As a result, the shape of the chamber 3310 may include a lowest point and may have a conical or triangular shape, the point of the triangle or cone being the bottom of the chamber 3310. It should be noted that although FIG. 33 illustrates transfer lines 3330 and 3370 that are located inside the chambers 3310 and 3350, according to various aspects of the current invention, the transfer lines may also be located outside of the chambers so as to drain the contents of the chambers from an outside location, as long as the end of the transfer line is at the lowest point of the chambers. For example, a transfer line may be configured so as to come out of a chamber, either in a vertical direction along the center axis of the chamber, or from the side of the chamber. In either configuration, the end of a transfer line may be located at the lowest point of the chamber from which fluid is being transferred. According to various aspects, the other end of the transfer line 3330 may be located at a high point of the chamber 3350, which is a point above the fluid level of the chamber 3350.

In order to transfer all of the fluid present in the first chamber 3310 to the second chamber 3350, the line 3322 may be opened to allow a pressurized inert gas to flow into the chamber 3310 and to create a pressure urging the fluid downward in the chamber 3310 and ultimately out of the chamber 3310 via the transfer line 3330. In addition, the gas line 3362 in the second chamber 3350 may be closed, and the vacuum line 3364 in the chamber 3350 may be opened by opening a vacuum valve located at the line 3364. As a result, a vacuum is created in the chamber 3350, and because the only other open opening in the chamber 3350 is the transfer line 3330 that is connected to the fluid in the chamber 3310, a suction action of the fluid present in the first chamber 3310 is created through the transfer line 3330. Accordingly, the combined action of the pushing action of the pressurized gas flowing in the chamber 3310 via the line 3322 and of the suction action of the vacuum created in the transfer line 3330 and provided via the chamber 3350 results in the entirety of the fluid present in the chamber 3310 to be transferred rapidly to the chamber 3350. Accidental subsequent fluid transfer to chamber 3390 from chamber 3350 may also be prevented by maintaining a positive pressure inside the chamber 3390 and the transfer line 3370 by, for example, flowing gas via the gas line 3382 into the chamber 3390 and possibly in the transfer line 3370. As a result of the existence of the positive pressure in chamber 3390, no fluid that has been transferred from chamber 3310 to chamber 3350 can accidentally be further transferred to chamber 3390.

It should be noted that during the transfer process, the pressurized gas line 3362 of the chamber 3350 may remain closed, and no pressurized gas is provided to the chamber 3350. However, a pressurized gas may be provided to the chamber 3350 via the gas line 3362 before any fluid transfer from the chamber 3310 to the chamber 3350 in order to keep the fluid in the chamber 3310 and avoid accidental transfer of fluid via the line 130 before such time when fluid transfer is desired. Accordingly, the pressurized gas is flowed inside chamber 3350 via the gas line 3362 while the vacuum line 3364 is closed. Because the only other opening in the chamber 3350 is the transfer line 3330, the pressurized gas flows through the transfer line 3330 into the fluid present in the chamber 3310. As a result, gas sparging or bubbling of the fluid may occur at the end of the transfer line 3330 located at the bottom of the chamber 3310, which may prevent any amount of fluid from accidentally being transferred from the chamber 3310 to the chamber 3350. Accordingly, accidental fluid transfer may be avoided, and no fluid is transferred before fluid transfer from chamber 3310 to chamber 3350 is desired.

The chamber 3350 may also have one or more input lines such as input lines 3352 and 3354, through which additional reagents, or ingredients, may be provided, for example during a second stage of a manufacturing or reaction process, after or before the fluid has been transferred from chamber 3310 into chamber 3350. Accordingly, mixing of various additional ingredients with the fluid transferred from the chamber 3310 to the chamber 3350 may take place inside the chamber 3350. A subsequent transfer of the fluid now present in chamber 3350 to chamber 3390 can be accomplished in a similar process to the process described above with respect to the transfer of fluid between chambers 3310 and 3350. To transfer the fluid from chamber 3350 to chamber 3390, gas line 3362 is opened to allow flow of a pressurized inert gas into chamber 3350 while vacuum line 3384 of the chamber 3390 is opened to create a suction action. As a result, the fluid present in chamber 3350 is entirely transferred to the chamber 3390 via transfer line 3370. In chamber 3390, additional ingredients or reactants may be added to the fluid via input lines 3392 and 3394.

Accordingly, an additional mixture or reaction of various fluids and chemicals may be performed in the successive chambers 3310, 3350 and 3390 during separate successive stages of an overall chemical process, and various effluents or fluids may be transferred to one or more of the chambers by manipulating the vacuum lines and pressure lines of the various chambers as discussed above, and without having to use wet valves or pumps in the transfer lines. For example, chemical synthesis may be performed in the various chambers 3310, 3350 and 3390 illustrated in FIG. 33. It should be noted that although only three chambers are illustrated in FIG. 33, there may be as many chambers as needed to effectuate any required number of reaction steps. It should also be noted that although the three chambers 3310, 3350 and 3390 are illustrated as being disposed in a generally vertical direction, the chambers may be located on the same plane, or have one or more chambers be located higher or lower than the other chambers. Also, with respect to the valves used to open and close the various gas, vacuum and input lines, many types of valves may be used such as, for example, ball valves, butterfly valves, globe valves, gate valves, diaphragm valves, check valves, and the like.

Modular Synthesis Subsystem/Backplane

In one example implementation of a system in accordance with aspects presented herein, a modular synthesis subsystem/backplane, examples of which are also interchangeably referred to herein as Multi-Synth Units, which may include for example hardware contained in a mini-cell. One variation of the Multi-Synth incorporates up to six synthesis modules in one mini-cell. Since the synthesis modules, the HPLC modules, and the cassette/reagent pack hardware are further described elsewhere herein, the Multi-Synth discussion in this section focuses on the remaining hardware, such as the module supporting structures, the backplane hardware, and provisions for installing the hardware and making electrical and plumbing connections.

To provide maximum flexibility in some variations, the Multi-Synth unit may accommodate six modules simultaneously. For a given processing run, these six modules could be all the same type, such as FDG synthesis modules, or they could be a mixture of several types of synthesis modules, such as FDG and Example F-18 Product 1A modules, and one or two HPLC modules.

Figure 34:
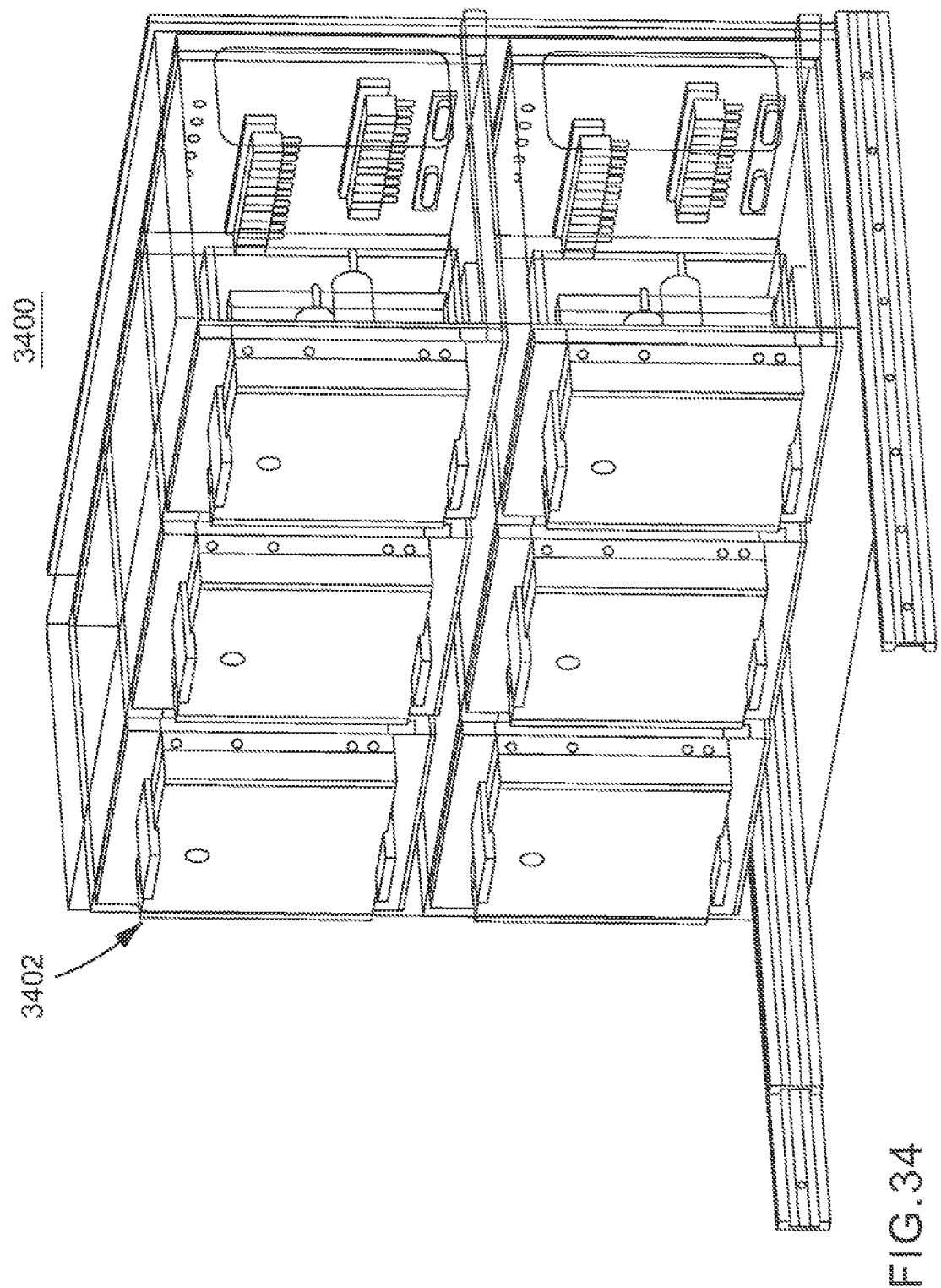
FIGS. 34-36 illustrate views of one example Multi-Synth devices, in accordance with aspects of the present invention.
Figure 35:
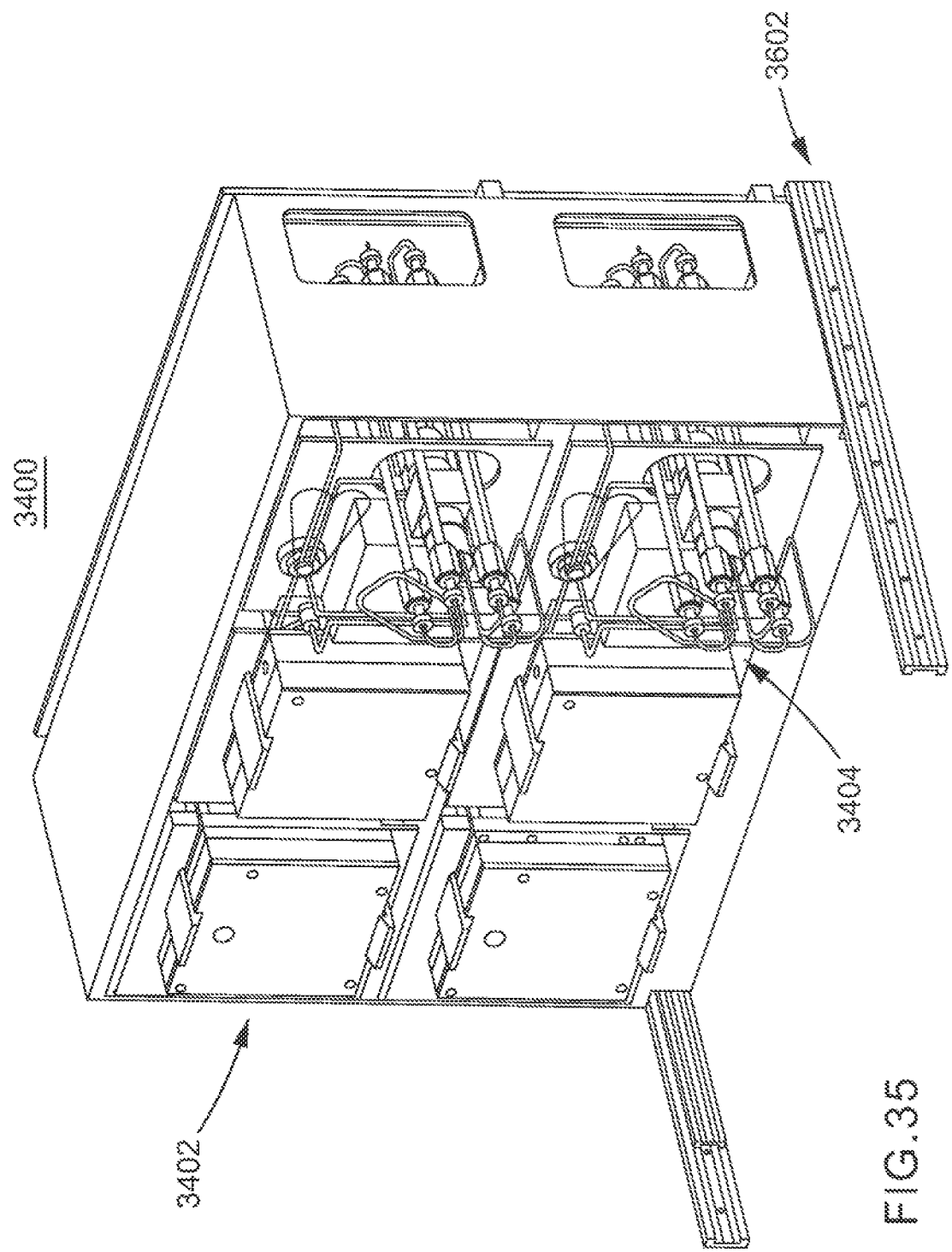
Figure 36:
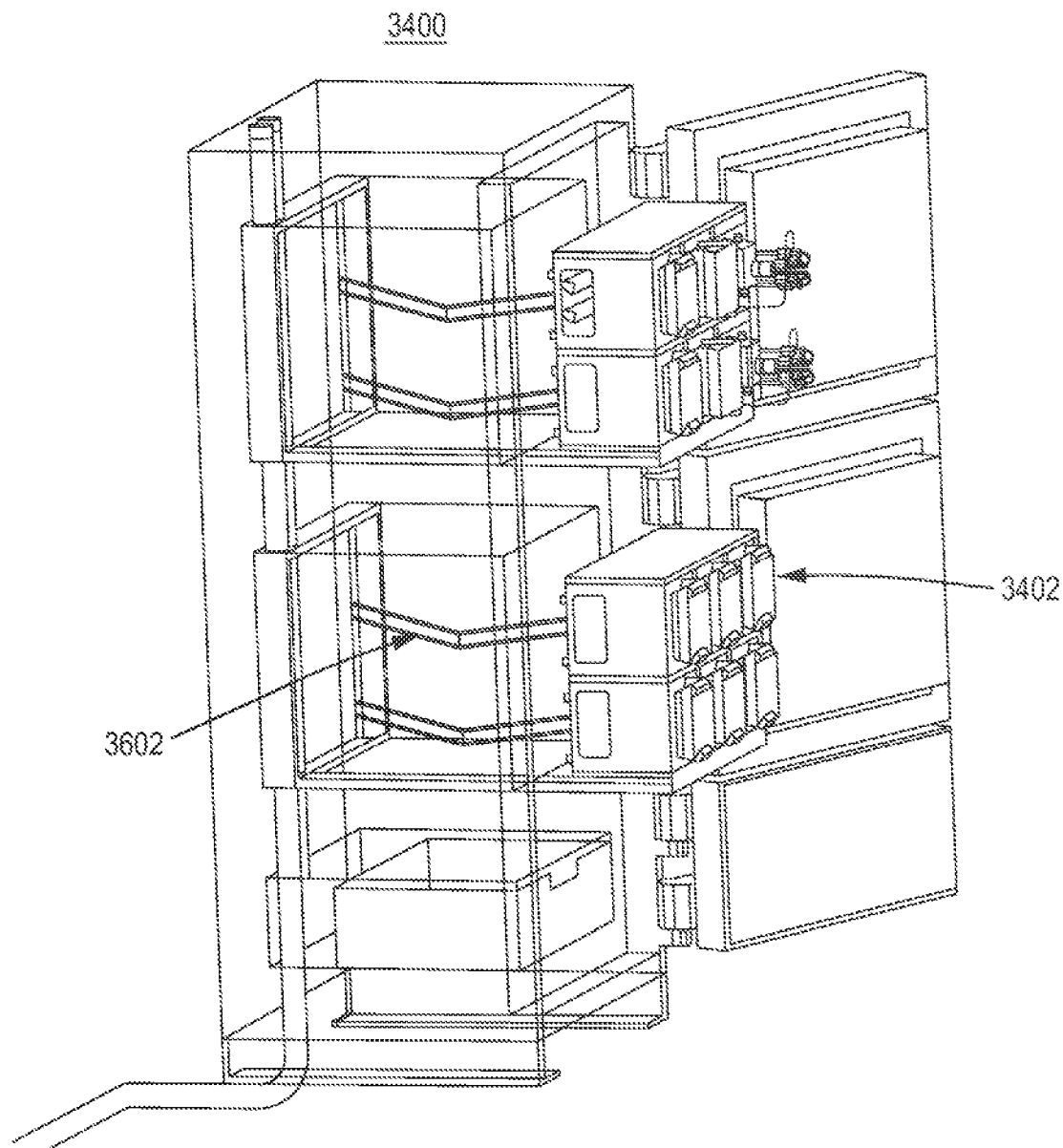

FIGS. 34-36 illustrate views of one example Multi-Synth design approach in accordance with aspects presented herein. In this approach the six modules 3402 are arranged in a 3 module 3402 wide by 2 module 3402 high configuration. This configuration provides best utilization of the example minimum interior mini-cell 3400 dimensions indicated. In this configuration, either or both of the two modules on the right side of the Multi-Synth may be configured as HPLC modules 3404, for example.

In this example, a framework supports the six modules, and this framework is attached to rack slides 3602 that permit the entire framework to be pulled forward from the mini-cell to provide access to the modules and the backplane (see FIG. 36). The rack slides will need to be firmly attached to the mini-cell to prevent tipping as the Multi-Synth framework is pulled forward. An initial estimate of the weight of the complete Multi-Synth unit for this example, with six modules installed, is in the range of 200 to 300 lbs. Most of this weight is in the modules themselves. Safeties, such as mechanical stops to prevent overextension and positive retainers to keep the rack slides securely in place, may be provided.

In one example implementation, the modules are installed in the framework by sliding them in from the front on low friction ways. A retaining pin or similar device may be used to provide positive retention once installed in the framework. Since ease and speed of removing and installing modules may be useful, most or all of the connections between the module and the backplane may be made automatically or easily as the module is pushed to the back of the framework, without the need for manual and/or other complex connection of individual fluid, gas, or electrical connections.

Additional details of such a modular cassette synthesis unit design approach are provided in U.S. Provisional Application No. 61/508,373, titled "MODULAR CASSETTE SYNTHESIS UNIT," the entire contents of which are hereby incorporated by reference herein.

Cassette and Reagent Pack

The overall cassette and reagent pack example outlined in this section provide disposable components for synthesis systems that have advantages over the components currently used in synthesis systems of the related art. Features of the overall cassette and reagent pack may include: small and compact hardware that is compatible with the Multi-Synth approach that incorporates six synthesis modules in one mini-cell; small cassette elements that process batches with activity levels up to 30 Ci but with smaller fluid volumes than currently used in the MX system; a cassette design that reduces processing time and provides consistently high yields; a cassette/reagent pack that is simple to install and does not require manual connections; and a cassette/reagent pack design approach that is configurable such that more than one radiopharmaceutical product can be processed per cassette mold design.

In one example system in accordance with aspects presented herein, the cassette is the component in which the synthesis is performed. The cassette performs the functions that are primarily performed by the disposable elements used in certain related art MX synthesis units. In the initial design approach, the cassette may contain several synthesis elements, including: 1) QMA cartridge; 2) a reaction vessel; 3) heating provisions for the reaction vessel; 4) chambers for mixing, neutralizing, and final product collection; and 5) one or more solid phase exchange cartridges. In addition, the cassette may incorporate numerous passages, connections, two-way membrane valves, and membrane pumps, for example.

The cassette may be held in contact with the module and have pneumatic, fluid, and electrical connections contained within or attached thereto. The side of the cassette opposite the module may be held in contact with a reagent pack, for example. The reagent pack, in one variation, has approximately the same footprint as the cassette, and may be clamped in contact with the cassette by mechanical clamping or other suitable coupling features. The reagent pack may contain the fluids and powders that are unique to the production of a specific radiopharmaceutical formulation. The reagent pack may either be a single component, or it may have one or more small insert sections, as needed, based on the storage requirements of the reagents. The reagent pack may be stored refrigerated, and an insert section could be stored separately if other requirements, such as freezing, are needed, for example.

Figure 37:
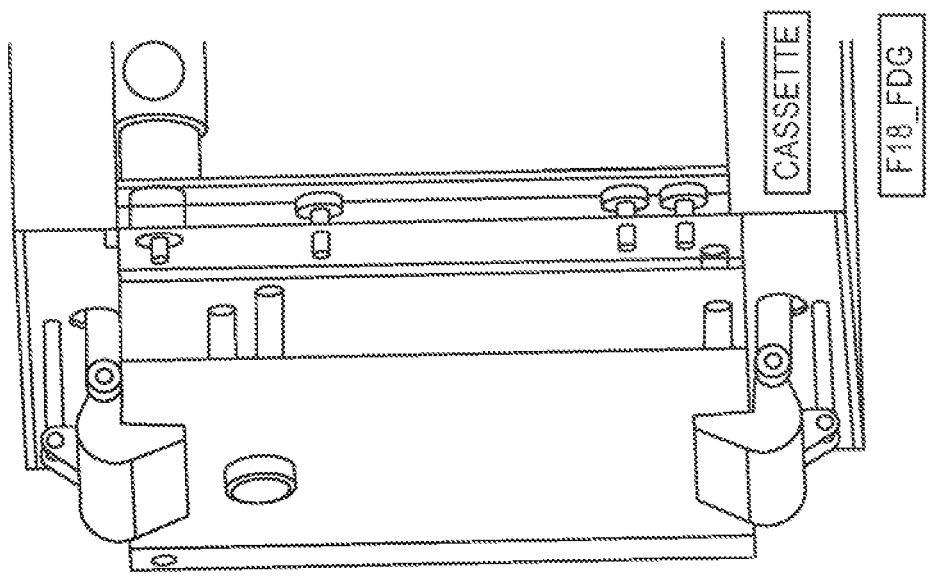
FIG. 37 shows a view of an example of a synthesis cassette and reagent pack installed on an example module, in accordance with aspects of the present invention.
Figure 38:
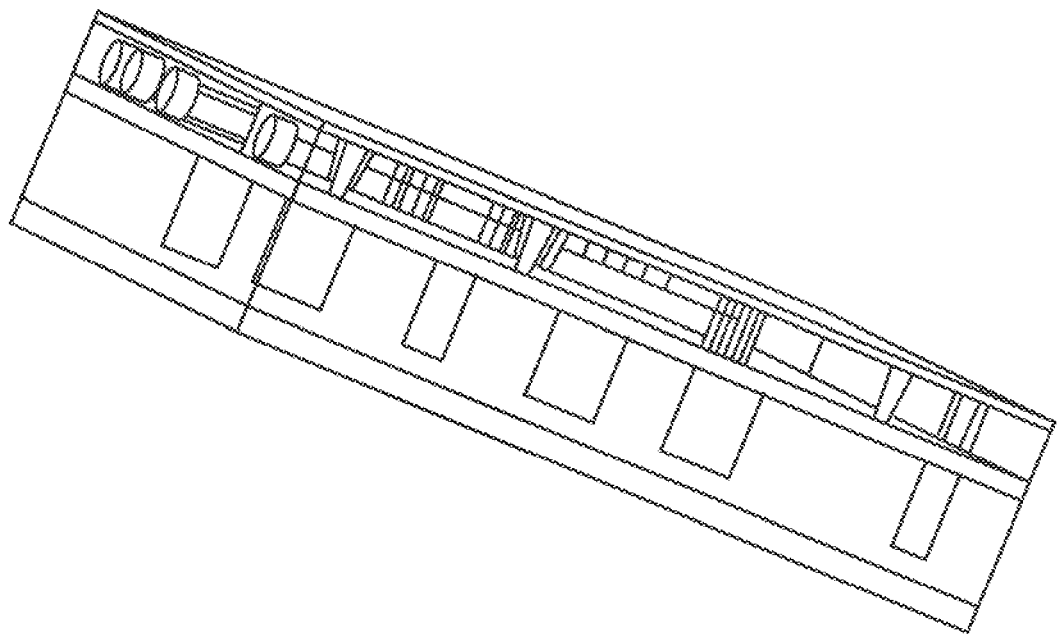
FIG. 38 shows an example of a synthesis cassette, in accordance to aspects of the present invention.

FIGS. 37 and 38 show views of an example variation of an FDG cassette and reagent pack installed on an example module, in accordance with aspects presented herein.

Further to as described in the Multi-Synth section hereof, in one variation, six modules are incorporated in a three wide by two high configuration in one Multi-Synth unit. FIGS. 34-36 show example views of one such arrangement configured with six synthesis modules. Each of these modules can support a synthesis cassette/reagent pack disposable subsystem. Based on space constraints in the mini-cells in this example, the modules each have approximately an 8" by 8" cross section, and an overall depth of about 10".

Since there may be more than one cassette configuration needed to accommodate the range of radiopharmaceutical products, more than one module configuration may be used. For example, one module configuration may be used for FDG and similar products that do not require HPLC access and another variation may be used for Example F-18 Product 1A and similar products that require an HPLC step. Module design approach for FDG and similar cassettes may also include consideration to the needs of the module that would support other products. To provide maximum flexibility, the Multi-Synth unit may accommodate six modules contemporaneously. For a given processing run, these six modules may all be the same type, such as FDG synthesis modules, or they may include a mixture of several types of synthesis modules, such as FDG and Example F-18 Product 1A modules, and one or two HPLC modules.

Synthesis modules in accordance with aspects presented herein may include features to: locate and support the cassette/reagent pack; provide connections between the cassette and the rest of the system for fluids and gases such as water, inert gas and vacuum lines, as well as disposable connections for the input line from the splitter, the output product line, and the waste line; provide one or more fluid pumps, and a multiple number of pneumatic valves and actuation lines; provide sensor and electrical connections for heaters, temperature sensors, pressure sensors, etc.; provide location and support for multiple radiation sensors; engage the reagent pack to the cassette and the cassette to the module when commanded, and to hold the cassette and reagent pack firmly to each other and to the module until synthesis is completed; eject the cassette/reagent pack from the module upon command; and do all of the above with minimum input required from the operator and so as to reduce and/or minimize user errors.

Figure 39:
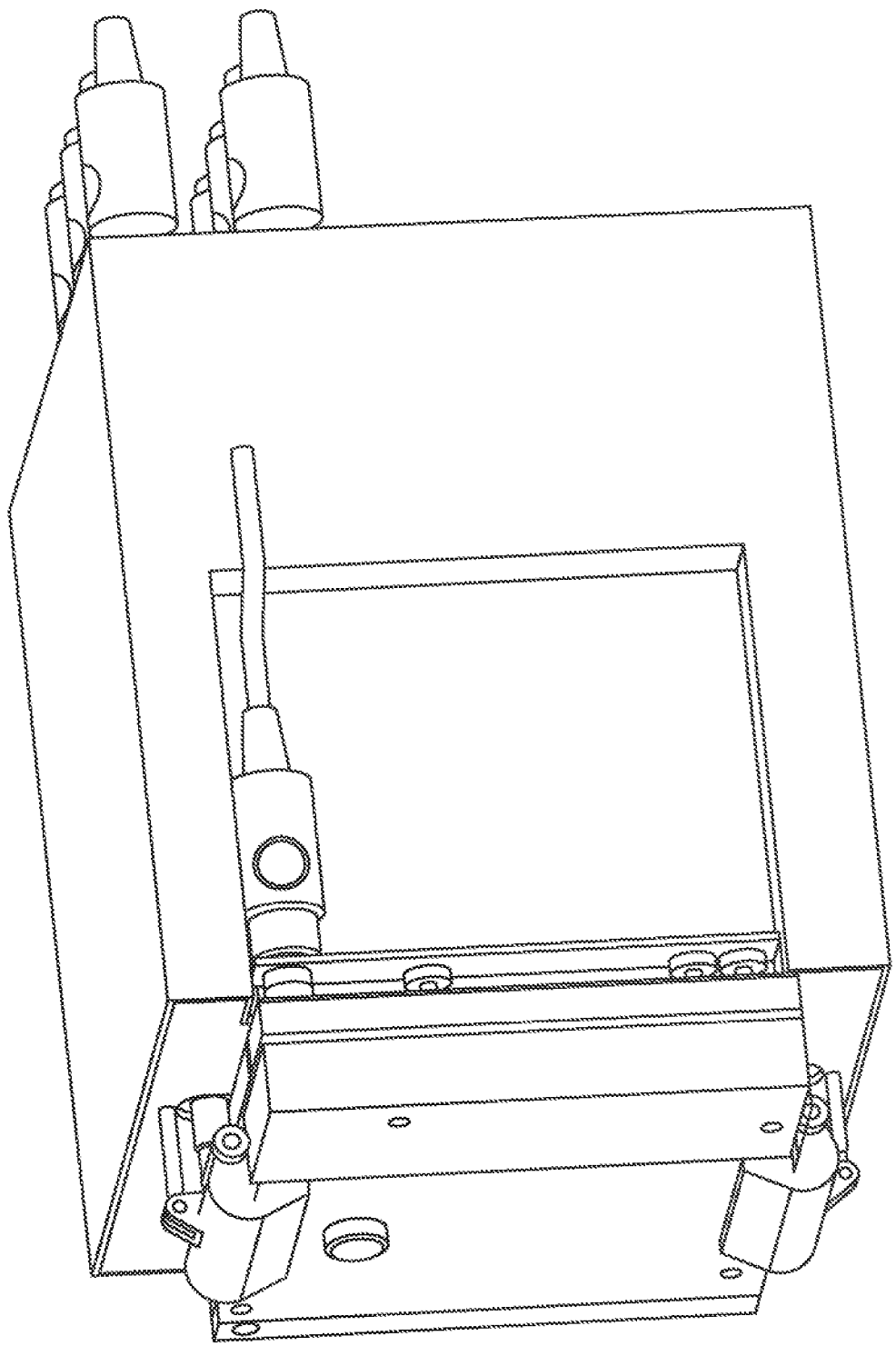
FIGS. 39, 40A, and 40B present an overview of one example synthesis module design approach, in accordance with aspects of the present invention.
Figure 40A:
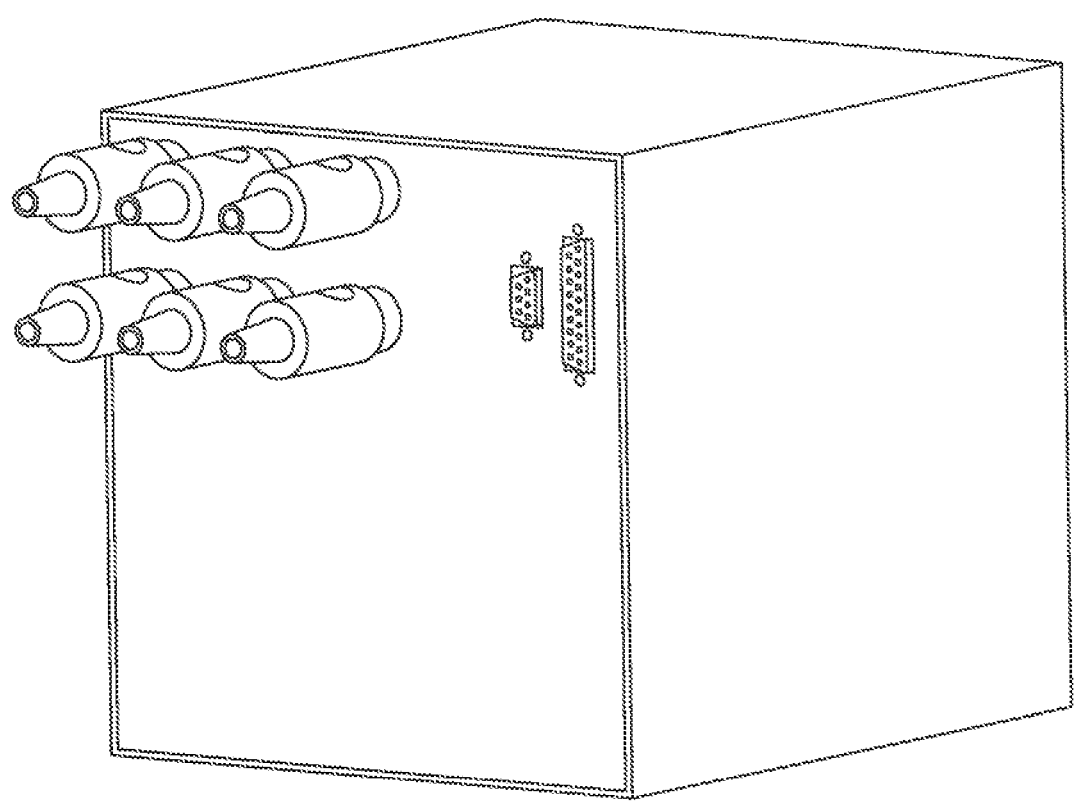
Figure 40B:
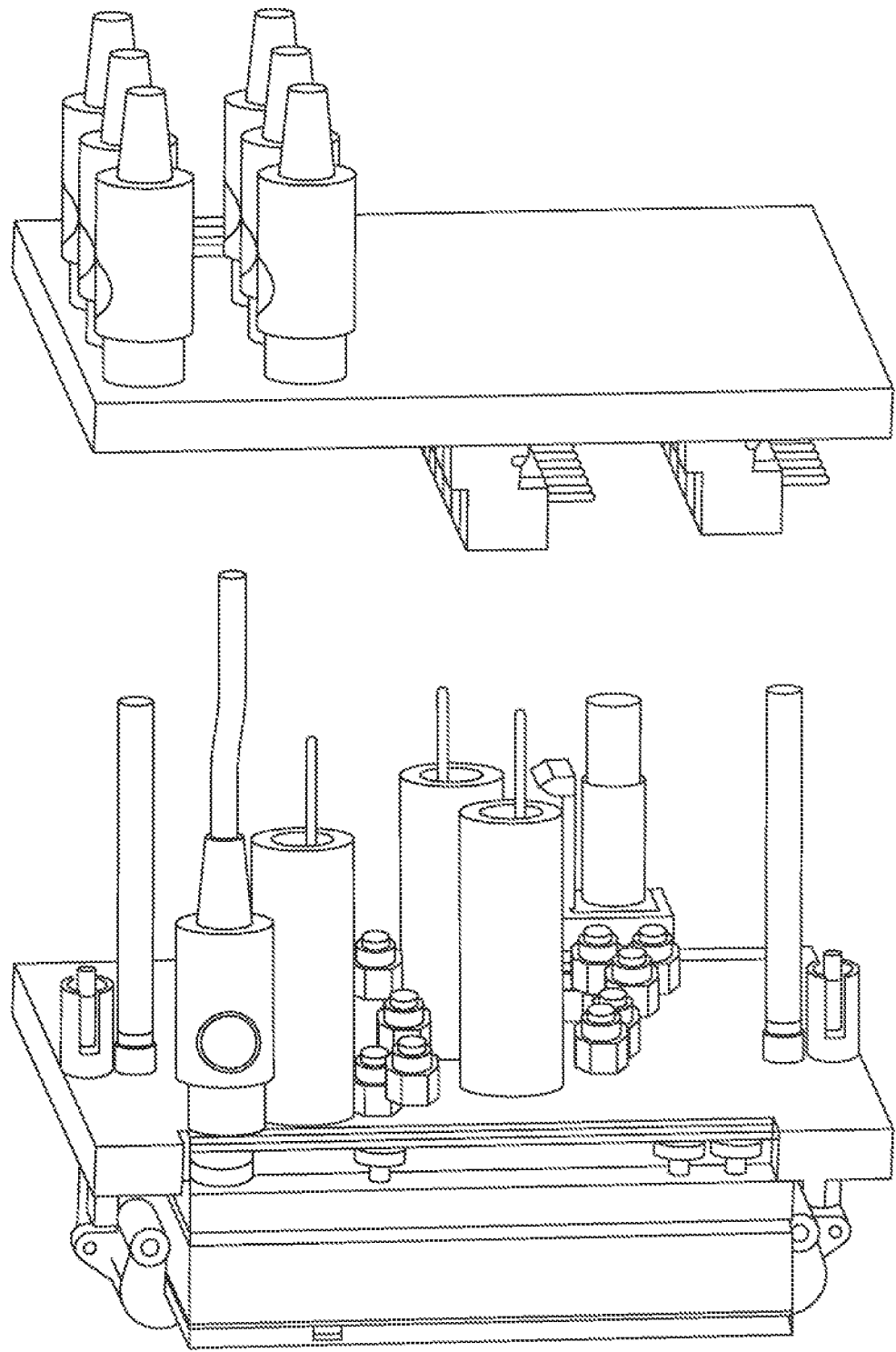

FIGS. 39-40 present an overview of one example synthesis module design approach, in accordance with aspects presented herein.

In one example variation, reliable connections between the cassette and the module and between the module and the Multi-Synth unit that require little or no input from the operator are provided. The connections between the cassette and the module in this variation may be made automatically for each cassette processed. The connections between the module and the Multi-Synth may be made automatically, for example, any time a module is installed. In addition, the fluid lines that supply the cassette with fluid from the splitter, transfer the final product from the cassette to the hot cell, and connect the cassette to the waste vessel may all be made accessible for frequent replacement. Based on these features, because of the limited space available with six modules in one mini-cell, as well as to limit the need to pull the entire Multi-Synth unit forward in the mini-cell to reach connections on the back side of the module, the following features may be included. The cassette to module connections may be implemented via a feature or features to automatically pull the cassette firmly against the module front plate just prior to initiation of synthesis; connections may be provided that are made automatically as the cassette is pulled against the module. Module to Multi-Synth connections may be achieved by implementing features that automatically make the fluid, gas, and electrical connections as the module is manually moved into position in the Multi-Synth. Additionally, connections of the replaceable line sets may be made by pulling a module partially forward in the Multi-Synth to provide access to the connectors.

The module design approach may incorporate a front mounting plate that interfaces with the cassette. This plate may incorporate multiple fittings (e.g., 4 for the FDG compatible module) to connect to tubing from pneumatic valves. Pneumatic passages from the mounting plate to the cassette may be sealed, such as by gasket material. The front mounting plate may also incorporate custom luer fittings, for example, for connection of fluid lines to the cassette. These fittings may use self-aligning, spring loaded components in the module, for example, in order to accommodate alignment of multiple fittings and to provide a uniform and controlled press fit for each fitting to prevent leaks. In order to avoid fluid lines that transfer radioactive fluids to and from the cassette being routed through the module, four of these luer fittings may be located on a separate side section of the module front plate assembly. This side section may extend beyond the side wall of the module and permit connections of the disposable fluid lines to the back side of this section, where they are assessable and do not pass through the module itself.

The module to Multi-Synth backplane connections may include fluid connections, inert gas connections, vacuum connections, electrical power connections, sensor connections, and computer and controller interface connections, for example. To avoid having to pull the entire Multi-Synth unit forward in the mini-cell to gain access to the connections at the back of the module, in some variation, connections may be made simply by sliding a module into the Multi-Synth unit. These connections may be robust, leak proof, and self aligning. In order to achieve adequate alignment for the couplings and connectors, some variations may include tapered guide pins that provide alignment as the module approaches the connectors. A locking pin or similar device may be engaged to hold the module in place once the connections are made, to, among other things, prevent unintentional disengagement of the connectors.

For FDG and similar products, for example, the module may contain one positive displacement pump. This pump may be used to provide metered volumes of water to the cassette. Since this pump is only used to provide cassette flushing after the synthesis is complete, flow rates and accuracy requirements may not mandate the use of a precision pump. The determination of activity levels in the incoming fluid from the cyclotron and splitter may be based on radiation sensing in the splitter unit. The determination of final product activity levels may be made in the hot cell. The use of radiation sensors in the synthesis units may primarily be for diagnostic purposes. In one example approach, for use, for example, with the synthesis of FDG and similar products, three radiation sensors may be provided. These sensors may be located in the module and positioned to provide diagnostic level data at three locations in the cassette: 1) within the QMA cartridge; 2) in the reaction vessel; and 3) within the first tC-18 or similar cartridge. These radiation sensors may be similar in design to the sensors used in the splitter, but may incorporate less tungsten shielding and a different geometry, for example, due to the space constraints in the module and cassette and the less demanding accuracy and range requirements in this application.

The modules may include features to enable pulling of the cassette and reagent pack together, and to hold them tightly against the module front plate in order to implement the fittings and sealing functions during the synthesis process. In one variation, one or more mechanical actuators are provided to pull the disposable reagent pack tightly against the module and hold them during synthesis. In the example configuration shown in FIGS. 39-40, two pneumatic actuators provide the motion and clamping force. When the actuators are fully extended, the linkage device opens the clamping devices to permit the operator to place the cassette and reagent packs on the module guide pins. Just prior to synthesis, the pneumatic cylinders may be commanded to pull the disposables into operating position. As the cylinders move the clamping devices inward within the housing, as shown in FIGS. 39-40, the biased (e.g., spring loaded) linkage may close the clamps over the disposables, and in the fully inward position, the spring system may control and limit the clamping pressure. After completion of the synthesis process, and upon command from control system, the pneumatic actuators may extend and eject the disposable reagent pack. Depending on the control system inputs, the actuators may move far enough to force the disposable reagent pack off the module guide pins, so that it is able to be dropped into a chute or slot, for example, or the extension may be limited so that the connectors and seals are disengaged, but the disposable reagent pack remains on the guide pins for later removal.

Synthesis Cassette

Aspects may include a chamber provided in a fluid handling cassette, arranged to allow the controlled movement of fluid through the remote action of pneumatic valves. The chamber may be a reaction vessel that having a substantially three-dimensional configuration, with an elongated shape and a relatively thin third dimension. For example, the reaction vessel may be flat, kite-shaped and oriented vertically, which allows liquid and vapor to separate and create a liquid level inside the vessel. Also, the thin third dimension of the vessel may be thin enough to force the liquid to spread over a predominantly flat wall through which heat or cold may be transmitted. The sides of the vessel may be tapered near the bottom in order to enhance the mixing effect of gas entering from the bottom port, and the sides may be tapered to provide a full evacuation of the liquid through the bottom port when the reaction process is complete.

In some variations, the synthesis process is performed in a small device that conducts the processing with smaller quantities of fluids. Since the maximum activity level goals are significantly higher than currently processed in related art MX units, this approach means that the activity concentrations may be much higher. For example, if the batch size is 30 Ci and the typical fluid volumes used are 25 percent of current volumes, the activity concentration may be about 8 to 16 times higher than encountered in 5 to 10 Ci batches for units of the related art. In some variations, sufficient additional room is provided in the cassette so that the volumes for individual process steps can be increased or decreased based on the needs of hardware or other constraints.

In addition to selecting cavity and fluid volumes, other variable features for the synthesis cassette may include fluidics, heating and cooling, reaction vessel configuration, sensor access, connections and sealing, and materials selection.

One example approach for electrical connections to the cassette is to use biased (e.g., spring-loaded) or other suitably engageable contacts, such as pogo pins or battery springs, to make connections when the cassette is clamped against the module. Where possible, the need for electrical components in the disposable cassette is avoided. An embedded temperature sensor in the cassette, near the reaction vessel, may be needed for some implementations to control heating processes, for example. Elsewhere in the cassette, activity may be monitored using non-contacting radiation sensors located in the module and aimed at SPE columns, where the reagents involved in the synthesis process may stand the greatest risk of being lost, for example.

Figure 41:
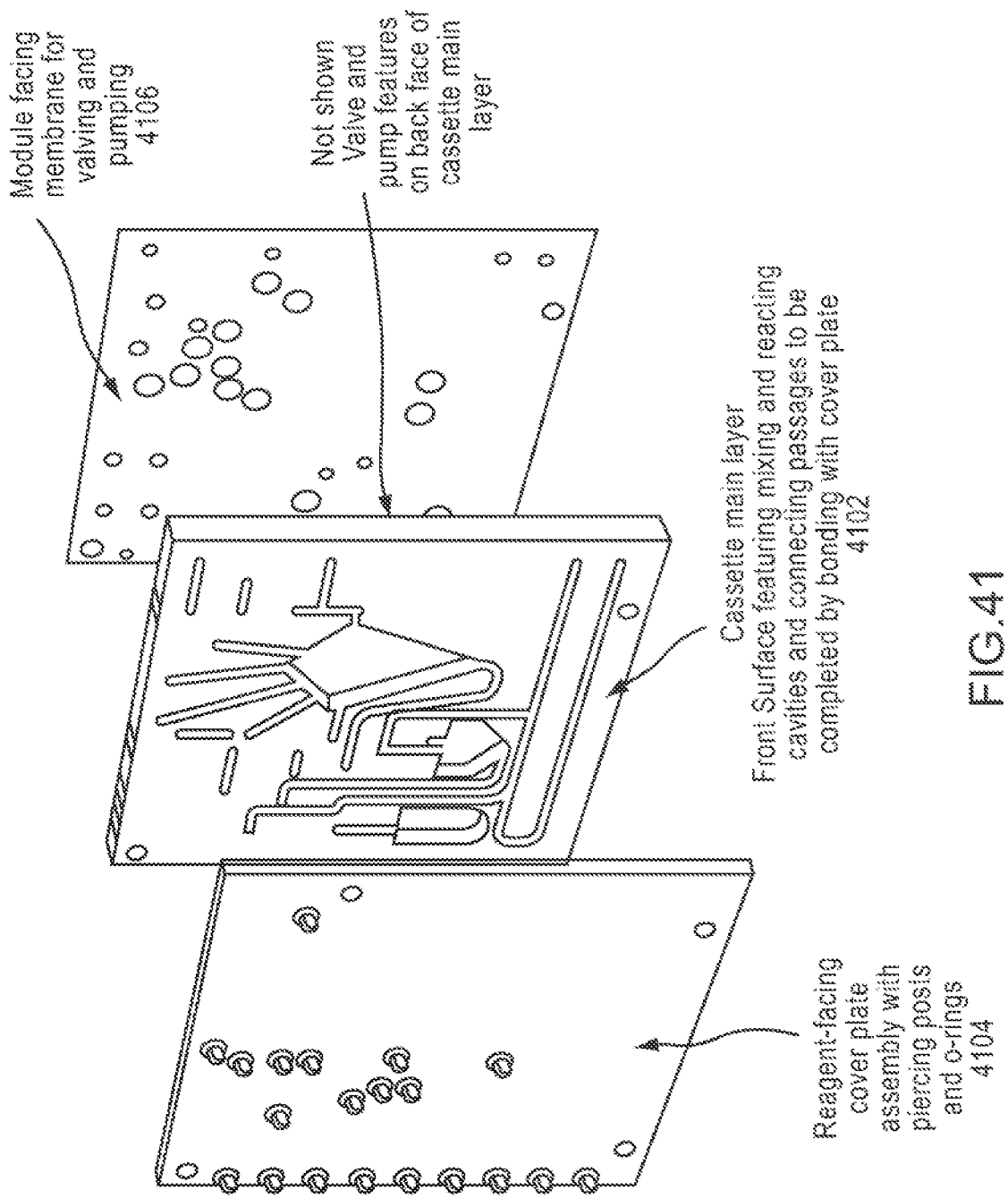
FIG. 41 shows an exploded view of various portions of an example synthesis cassette, in accordance with aspects of the present invention.

FIG. 41 shows an exploded view of various portions of an example synthesis cassette, in accordance with aspects presented herein. FIG. 41 illustrates a cassette main layer 4102, a cover-plate layer 4104, and a membrane layer 4106.

Certain features of the cassette for some implementations may vary from those depicted in FIG. 41. One such feature that may vary is the cassette main layer 4102, which may be formed from two different materials, such as a highly thermally conductive material around portions of the reaction vessel cavity, and a low thermal conductivity material elsewhere. Another varying example may be the cover plate 4104 assembly with piercing posts, which may integrate the piercing posts as features of an injection molded part containing locally raised contact surfaces for the reagent pack assembly and that may allow large clamping forces to be transmitted, while limiting the compression of the o-ring seals around each piercing feature.

Reagent Pack

In accordance with aspects presented herein, the reagent pack is or comprises the disposable component that contains the processing fluids and powders that are needed to synthesis a specific radiopharmaceutical product. Since each radiopharmaceutical product requires a unique combination of reagents, both by type and by volume, each product requires a unique reagent pack. These reagent packs may need to be stored under conditions appropriate for the reagents, and then assembled with the synthesis cassettes at the time the mini-cell is loaded for the next processing runs. Reagent packs may have unique mechanical features to prevent improper orientation on the cassette and to make sure that the cassette and reagent pack are compatible.

In some variations of the reagent pack, several of the more commonly used fluids, such as acetonitrile, ethanol, and water are supplied from bulk supply lines through the module. This approach reduces the size and complexity of the reagent pack. In other variations, the reagent pack stores all of the fluids and powders that are to be used in the cassette, except the final flushing water, such as may be used after the product has been sent to the hot cell.

For many radiopharmaceutical products, one or more of the reagents may need to be stored in powdered form and then mixed just prior to introduction into the cassette. The cassette and/or the module may need to provide pumping and valving provisions to accommodate this mixing process. For some products, one or more of the reagents may need to be stored under conditions that are not appropriate for the remainder of the reagent pack, such as at temperatures below freezing. For these products, the reagent pack may need to accommodate one or more small reagent capsules, for example, which are inserted into the reagent pack just prior to installation in the mini-cell.

Figure 42:
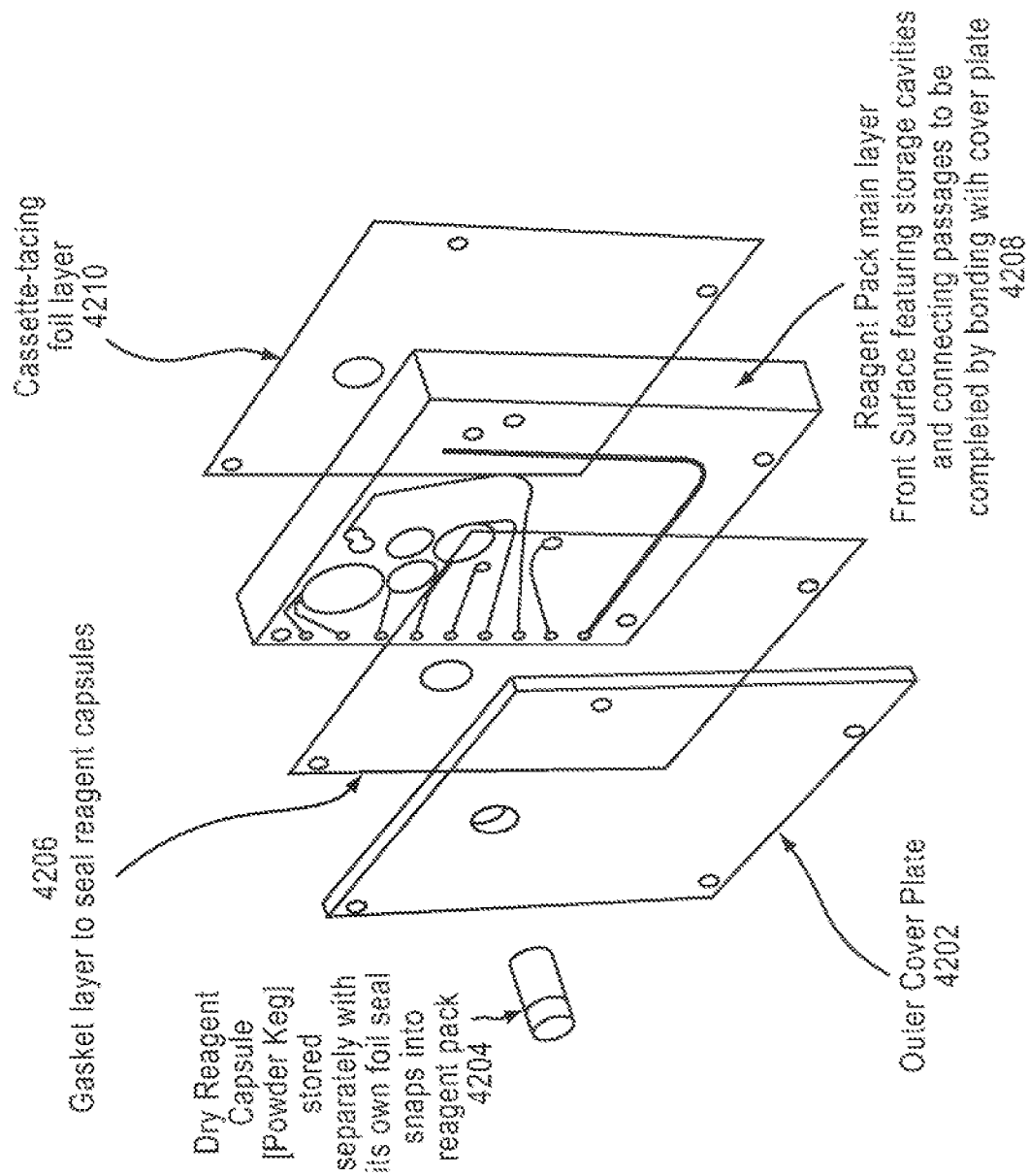
FIGS. 42 and 43 illustrate exploded views of various features of an example reagent pack, in accordance with aspects of the present invention.
Figure 43:
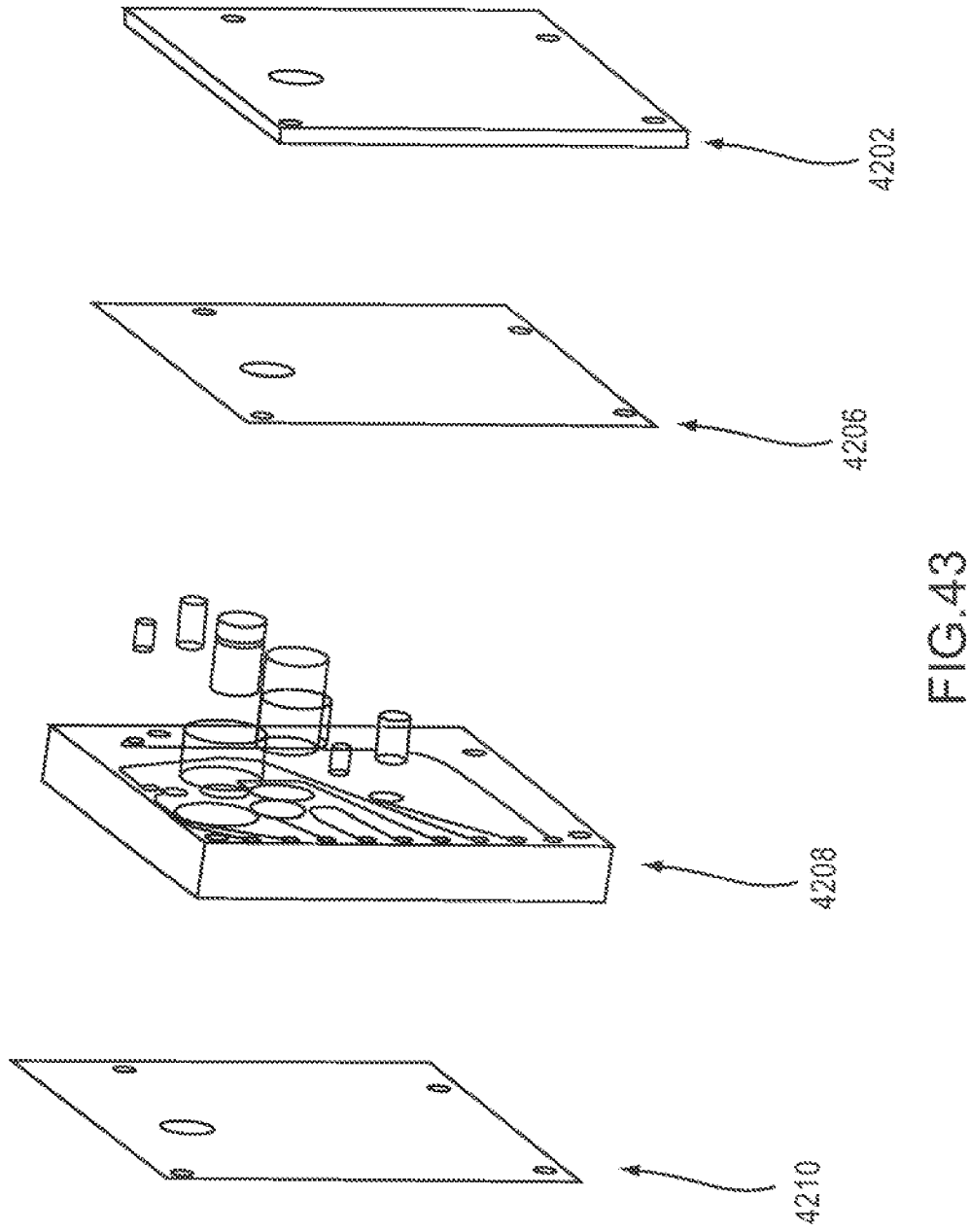

FIGS. 42 and 43 illustrate exploded views of various features of an example reagent pack, in accordance with aspects presented herein. FIG. 42 illustrates an outer cover plate 4202, a gasket layer 4206, a reagent pack main layer, and a cassette facing foil layer, each having an opening configured to receive a reagent container 4204. FIG. 43 illustrates an additional view of these layers.

In some variations, the reagents may be stored in individual cavities in the Reagent Pack main layer. The cavities in these variations are completed by the permanent assembly of an outer cover plate to the main layer. Each reagent cavity may have two exits on the cassette-facing side, a fluid exit and a vent. After the cavities are filled with reagent, both exits are sealed by a foil layer. When the reagent pack is assembled by the user onto the module and in front of the cassette, standoffs prevent the foil from being immediately pierced by the cassette assembly. When the system is ready to begin synthesis, for example, the standoffs may be removed, or overcome, by the clamping mechanism. The clamping force thereby causes the cassette assembly to pierce the foil of the reagent pack assembly, merging the fluidic circuits of the two disposable parts with the durable fluidics of the module. In one example implementation, one or more O-rings or other sealing mechanisms are incorporated around each piercing feature to seal the merged fluidic system against external leakage.

Materials may be selected to allow extended storage of reagent pack assemblies before use. Particularly difficult solvents may require additional protective layers in the form of inserts, or coatings, for example. Different materials may also be selected for the main layer of the reagent pack, according to the process for which the pack is intended.

Examples of volumes and types of fluids and powders that may be stored in reagent packs, in accordance with aspects presented herein, are included in the tables of FIGS. 9 and 11.

Figure 44:
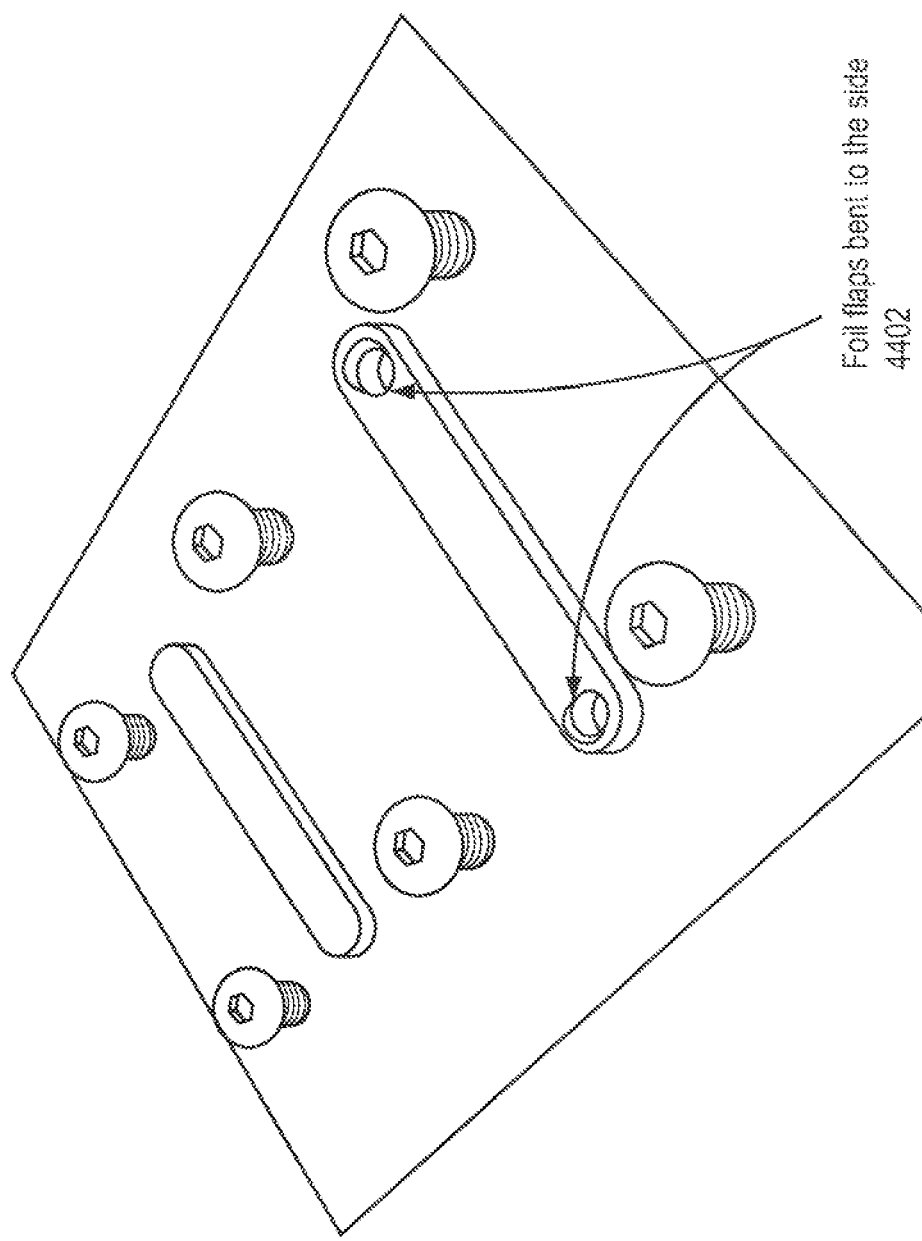
FIG. 44 shows an example of bent foil flaps produced using angled piercing posts, in accordance with aspects of the present invention.

As shown, for example, in FIG. 41, the orientation angled piercing posts may be important in some implementations to control, for example, where the flap of foil ends up (see, e.g., Photostat in FIG. 44 of example bent foil flaps 4402 produced using angled piercing posts, in accordance with aspects presented herein). In some directions, the flap of foil could partially obstruct the flow of reagent if a proper angle is not produced. For example, folding the flap directly away from the flow direction may create a region of trapped fluid.

The size and shape of the piercing post for use in foil pierced mixing of components requires a good match of foil thickness and reagent cavity opening clearance. The O-rings may be sealed acceptably, for example, but the design must also limit their compression by including other contacting features between the reagent pack and the piercing plate. Shorter posts may be used so long as they retain enough engagement to fold the foil flap out of the way.

By re-routing a solvent back into the reagent pack, a powdered reagent may be mixed by the flow of solvent through the cavity storing the dry powder. The dry cavity may be designed to store the powder near where the solvent enters, and include a serpentine path before leaving the reagent pack to ensure complete mixing.

HPLC Cassette

In one example implementation of a system in accordance with aspects presented herein, several radiopharmaceutical formulations that are of interest, such as Example F-18 Product 1A, may require synthesis steps that include processing in an HPLC unit for purification. The size and complexity of the components used in commercial HPLC units make it impractical to incorporate the HPLC functionality in the synthesis cassettes and modules. In some variations, therefore HPLC functionality is incorporated in separate modules dedicated to that purpose, e.g., the HPLC units 3404 illustrated in FIG. 35. Since the system may be intended to incorporate up to six modules in a mini-cell, for example, one or more of the six synthesis modules may be replaced by HPLC modules when formulations such as Example F-18 Product 1A are to be processed. In this configuration, an HPLC module may be installed next to an Example F-18 Product 1A synthesis module with appropriate fluid connections between the modules. Even with this module approach, size constraints may require that some of the HPLC components be located outside the mini-cells.

Components in example HPLC units may include an injection loop 4502, to gather and then inject the sample into the HPLC flow path; an HPLC column 4504 that contains the appropriate packing material for the application; a high pressure pump 4506 to deliver a mobile phase (solvent) and the sample through the tightly packed column; a source 4508 for the appropriate mobile phase solvent; one or more detectors 4510, to determine when the selected fluid constituent is exiting the column; a selector valve 4512 to route the fluid exiting the column either to waste or back to the synthesis cassette; and control components and sensor instrumentation.

Implementations of the system may provide a platform to synthesize a variety of radiopharmaceutical formulations requiring HPLC processing. Several approaches to reduce the component and/or module swapping may be used to accommodate a variety of formulations, including the following: revising or adapting the radiopharmaceutical formulations to use a smaller number of different column packing materials and solvents; this approach may reduce the number of HPLC options to perhaps two or three, but may require changes in the formulation recipes, which could in turn lead to licensing and/or FDA approval complications; varying HPLC modules for each formulation, and ensuring that these modules relatively easy to swap out; different solvent sources may also be needed; varying the HPLC module to make it relatively easy to swap out of the column, so that the appropriate column is in place for the next formulation that is scheduled; different solvent supplies may also have to be available for this approach; and using an HPLC module that incorporates a column selector device and provides multiple columns to choose from without need for hardware swapping; this approach may also require a pumping system that can select from multiple solvent sources without component swapping.

Figure 46:
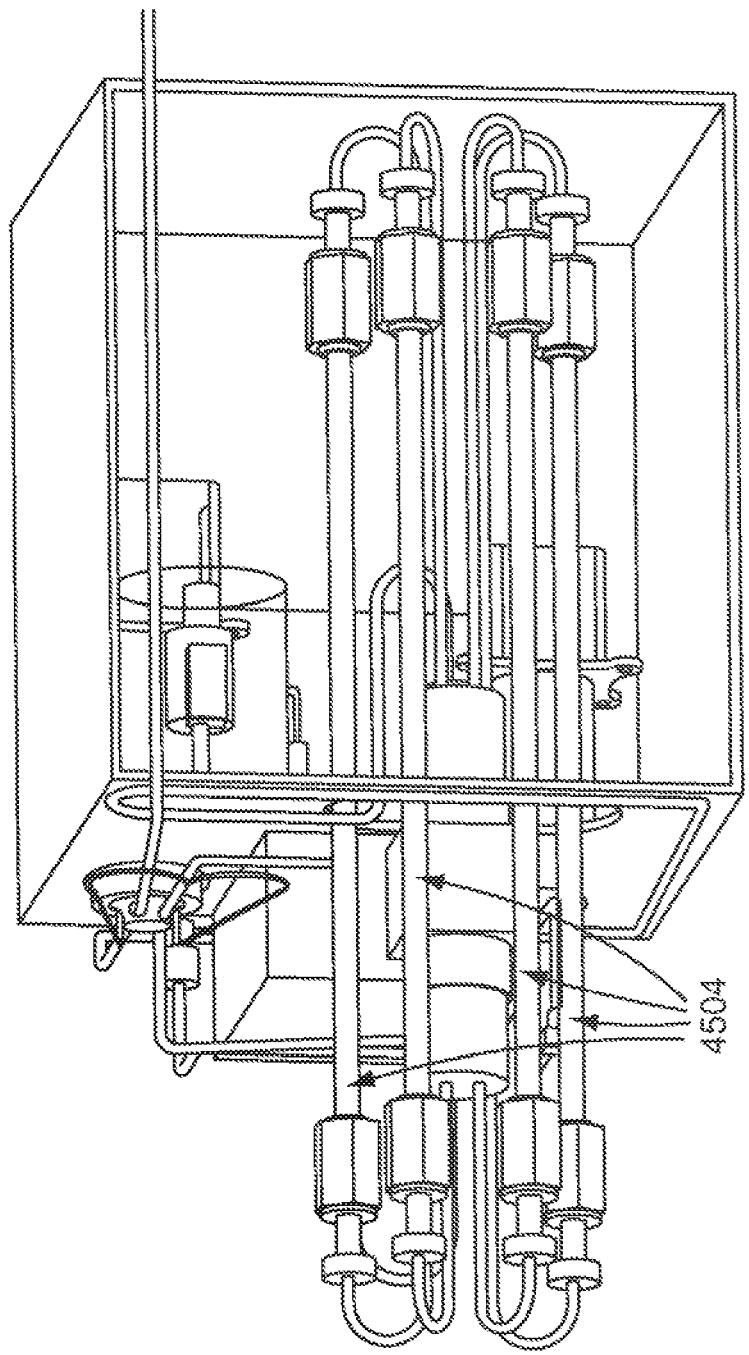
FIGS. 46 and 47 present an overview of one example design approach to the HPLC/Low Pressure chromatography/Flash chromatography as well as types of Sep-Pak purification module in accordance with aspects of the present invention.

In multiple column selector variations, the HPLC module may incorporate a four-way selector valve and four HPLC columns, for example. FIG. 46 illustrates an HPLC module having four HPLC columns 4504. Each of these columns may contain a different packing material if desired, or several columns may contain the same type of material, with one being used as a backup for the other. The injection loop may be placed in the circuit ahead of the four-way selector. Since different formulations may require different solvents, a mobile phase pump that is able to select among four different solvent sources may be used. This pump may also have provisions to flush line sets in between applications.

Figure 45:
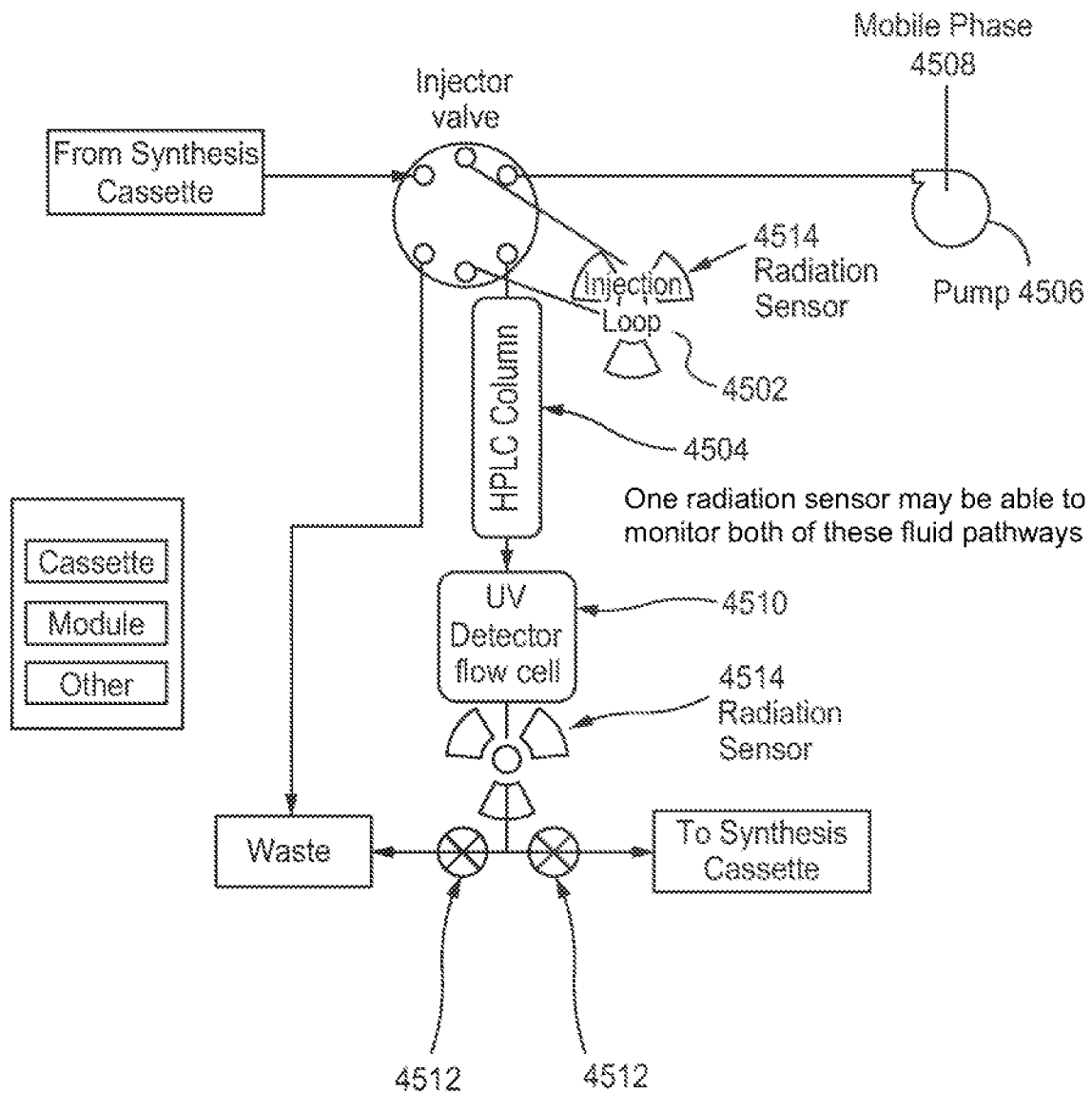
FIG. 45 shows a schematic of an example HPLC system module in accordance with aspects of the present invention.

A schematic of an example HPLC system in accordance with aspects presented herein is shown in FIG. 45. The HPLC module shown in FIG. 45 includes two detectors, a radiation sensor 4514 and an ultraviolet (UV) sensor 4510. The outlet fluid from the columns passes by the UV sensor and then the radiation sensor. The UV sensor alerts the system that the constituents of interest are exiting the column, and the radiation sensor determines when the selected radioactive material is exiting the column. This data may used to direct the selector valve, in order to send the desired material to the return line to the synthesis cassette, for example, rather than the waste line.

Due to space constraints and the radiation activity levels inside the mini-cell for some variations, as many of the HPLC components as practical may be located externally to the mini-cell. Such external components may include, for example, the solvent pump and solvent supply systems, the sensor electronics, and the control system for the selector valves.

The connections to the synthesis cassettes may be made by connectors at the side of the module nearest the synthesis modules. As the synthesis cassette is pulled into contact with the synthesis module, for example, the cassette may then also make connections to the HPLC module.

The columns shown in the example implementation shown in FIG. 45 are full-size 250 mm long columns as may be used, for example, in Example F-18 Product 1A processing. It may be possible to reduce the length and/or diameter of the columns for some formulations, based on reduced fluid volumes that are expected to be used in some variations of synthesis processes in accordance with aspects presented herein. Shorter or smaller diameter columns may be used with the same selector valve by making minor connection line changes, for example.

Figure 47:
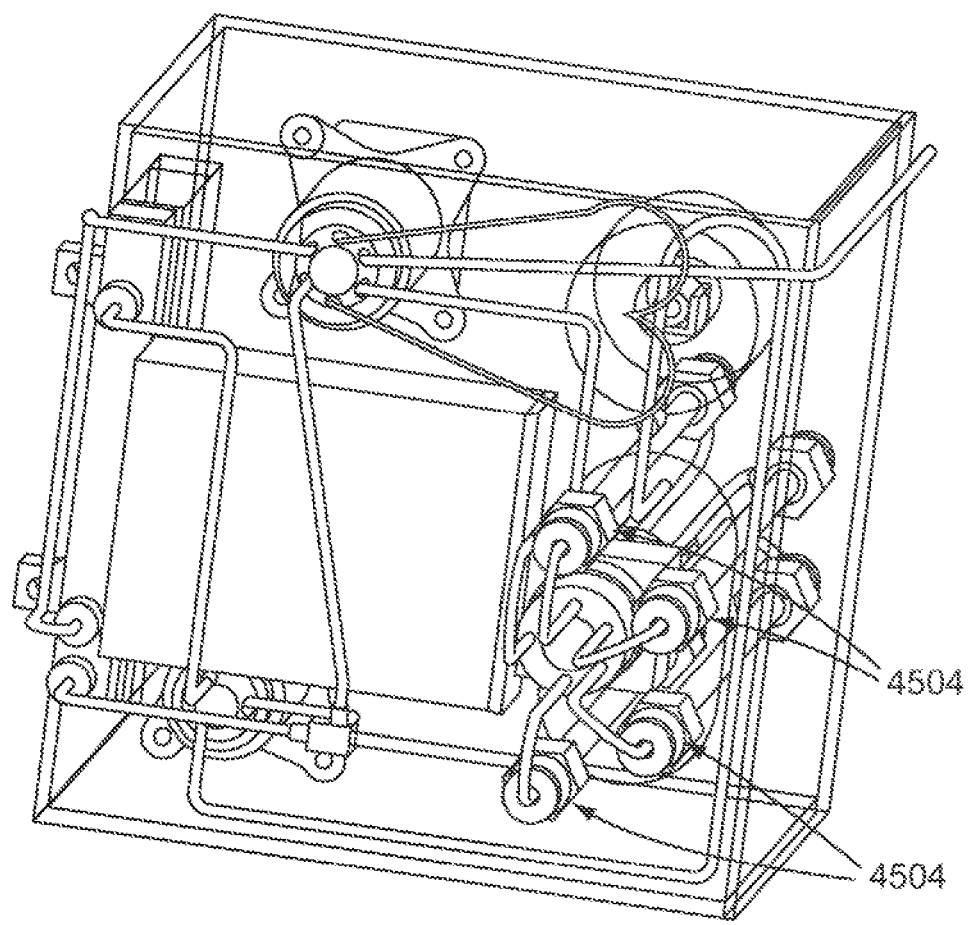

An overview of one example design approach to the HPLC module in accordance with aspects presented herein as outlined above is illustrated in FIGS. 46 and 47. Example commercial components that may be used for certain features include: a Solvent Pump, such as a Dionex Quaternary Analytical Pump (LPG 3400SD); a four-way Column Selector, such as a VICI Cheminert HPLC Column Selector unit (C5-2004EMHD); and an injection Valve and Loop, such as a RHEODYNE, RV700-114, 2-POS, 6-PORT Motorized valve.

Additional details of such an HPLC may be found in Provisional Application No. 61/508,349, titled "System for Radiopharmaceutical Preparation Involving Solid and Liquid Phase Interactions," filed on Jul. 15, 2011, the entire contents of which are hereby incorporated by reference herein.

Disposable Columns

Various components of the HPLC module may be replaced periodically, or be changed when used for synthesizing different radiopharmaceutical compounds. Typically, a component of the system may be replaced while the system is not operating to prepare a radiopharmaceutical. For example, after a column 3404 is used in multiple runs of the HPLC module to purify radiopharmaceutical products, it may deteriorate or not function effectively to separate the desired radiopharmaceutical material. Failure of a column is usually detected, for example, by a large pressure increase in the pump at a set mobile phase flow rate or a longer process time for separating the desired radiopharmaceutical material than is typically required. Such a failure may occur after about 10 to 100 runs of the HPLC module with that column.

In accordance with aspects presented herein, the deteriorated column may be replaced with a different column. In addition, a column having a specific stationary phase may be required to produce a particular radiopharmaceutical compound. Thus, according to aspects presented herein, a column in an HPLC module having one stationary phase may be removed from the HPLC module and replaced with another column that has a different stationary phase, for example. To simplify the removal of a column from the HPLC module, at least one edge of the container that houses the HPLC module's components may be removed and columns may be positioned at an edge of the HPLC module.

Automated Quality Control (QC) Platform/Lab Information management (LIM)

In accordance with aspects presented herein, an automated QC system and apparatus may be used, for example, for radio-synthesized tracers, covering a plurality of tests, which assess, for example, particle and color content (clarity), filter membrane integrity, pH value, residual solvent volume, Kryptofix concentration, bacterial endotoxins concentration, radionuclidic identify, radionuclidic purity, radiochemical identity, radiochemical purity, and sterility test.

The automated QC system and apparatus may advantageously record documentation and archive the materials used in the QC process and report various testing results in compliance with the current Good Manufacturing Practice (cGMP) regulations, as well as title 21 CFR Part 11 of the Code of Federal Regulations regarding the Food and Drug Administration (FDA) guidelines on electronic records and electronic signatures in the United States. Aspects also enable self-calibration of all of the tests with reporting capabilities in real time. In one aspect, simplified and fully automated QC operation is enabled by facilitating each of the above tests in an efficient manner (e.g., in less than 30 minutes). The test results may be quantitative, and multiple tests may be advantageously performed in parallel. As a result, the test results may be more reliable, and the whole process may be more economical and efficient, as time and labor for the QC are significantly reduced.

Additional details regarding the Quality Control aspects may be found in U.S. Provisional Application No. 61/508,353 titled "Method and System for Automated Quality Control Platform," filed on Jul. 15, 2011, the entire contents of which are hereby incorporate by reference herein.

Sterile Vial Fill Subsystem and Methods

To create an aseptic environment for the production of pharmaceuticals, a special clean air "canopy" or laminar flow hood, for example, is often used, wherein high-efficiency particulate air (HEPA) filters are provided in conjunction with a closed containment structure, within which the pharmaceuticals can be prepared. The interior environment of the containment structure is closely monitored, for example, by a particle counter, to determine the airborne particulate density of possible contaminates. However, when preparation of the pharmaceutical includes a radioactive material, the aseptic environment described above must also be shielded. It is very difficult to combine a shielded enclosure with a filtered environment without compromising the ability to produce a radiopharmaceutical compound efficiently.

Furthermore, present procedures for dispensing radiopharmaceuticals into final product vials for delivery to one or more patients often involves accessing and extracting the radionuclide product for an individual procedure from a bulk product vial. The bulk product vial, which is contained in a shielded enclosure to minimize exposure of the technician to radiation, is typically accessed by one or more technicians using a syringe to puncture a resealable membrane of the bulk product vial in order to extract a quantity of the radioactive component, introducing a chance that contaminants can be introduced into the bulk product vial.

To decrease the chance of contamination by multiple punctures of a syringe, it has been proposed to use an automated syringe that automatically draws material from the bulk product vial into each of the individual vials. However, even if a syringe pump, for example, reduces the chance of contamination by reducing the number of times the bulk product vial membrane is punctured, each plunge of the syringe after the initial plunge risks contamination through airborne particles, for example, being drawn in through the back of the syringe. Additionally, syringes can limit the size of a dose being dispensed.

Accordingly, there is a need for improved vial filling systems that may promote a more efficient setup and procedure for dispensing radiopharmaceuticals in a safe and effective manner that guarantees the integrity of the radiopharmaceutical every time.

In accordance with aspects presented herein, an example sterile vial fill subsystem is a closed path system that incorporates features and methods to provide for aseptically dispensing finished radiopharmaceuticals into receiving vessels, such as a Quality Control vial, a sterility vial, and/or final product vials. The system is designed with disposable components that provide users safe and efficient mechanisms for aseptic assembly of the system, as well as removal and disposal of those components that are exposed to radioactivity during use of the system. Moreover, by automating the dispensing process in a closed system, the chance of contamination associated with current systems and methods, including, for example, automated syringes, may be substantially reduced or eliminated altogether.

The closed path vial system may include a bulk product vial for receiving a bulk quantity of a radiopharmaceutical product, a peristaltic pump operated by a stepper motor for precise control and delivery of the product from the bulk product vial to the receiving vessels, a dispensing manifold assembly to which may be coupled multiple receiving vessels for receiving the product, as determined by an automated control system, an optional quality check station, and an optional waste collection system. Furthermore, a CAV Sensor may be incorporated into the system for receiving the radiopharmaceutical product directly from a synthesizing unit and measuring critical product properties prior to dispensing the product via the automated sterile vial fill subsystem.

Figure 48:
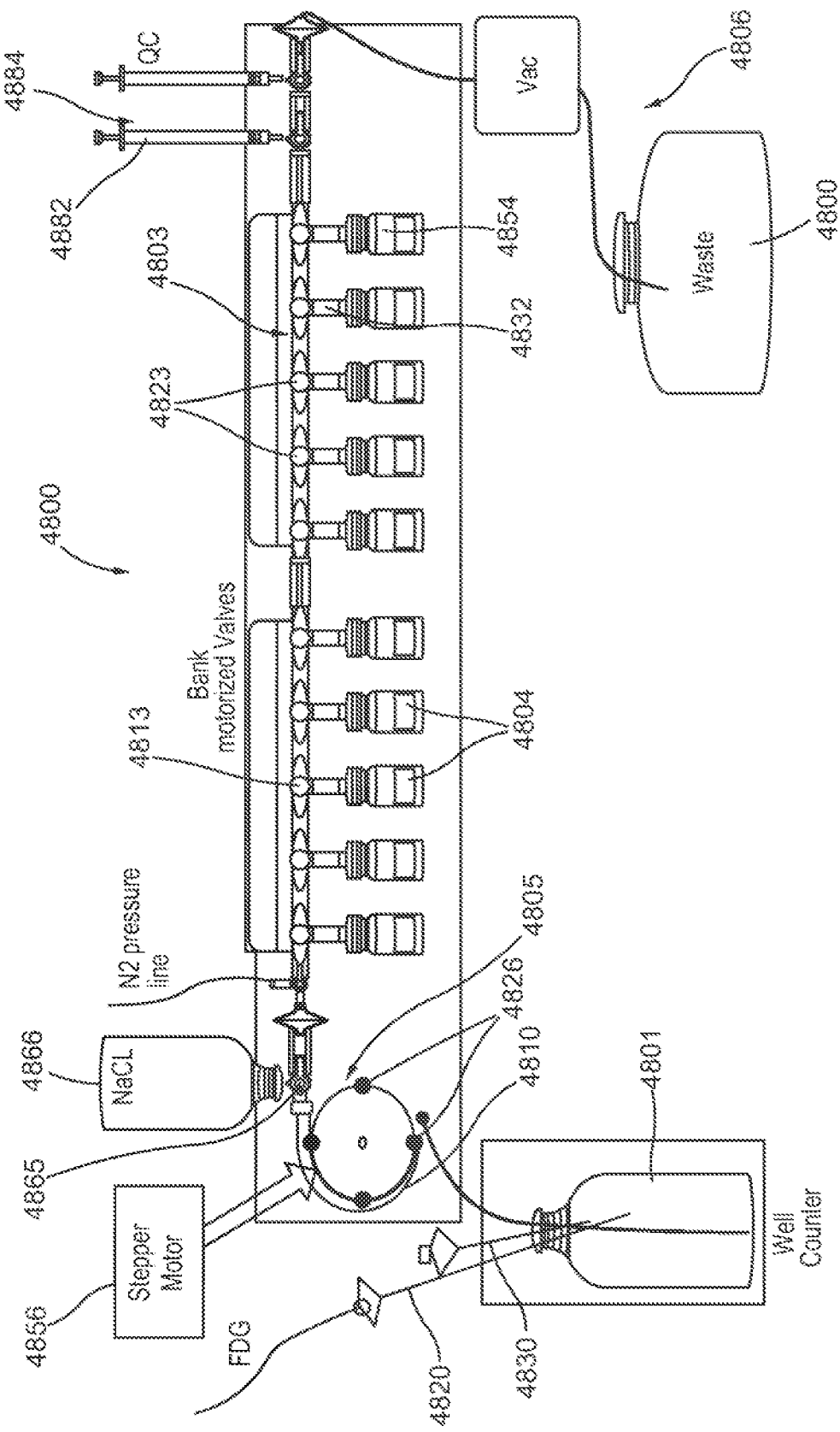
FIGS. 48, 49, and 50 show aspects an examples of vial fillers, in accordance with aspects presented herein.

As shown in FIG. 48, an exemplary closed path vial fill system 4800 may include a bulk product vial 4801, a peristaltic pump 4805, a dispensing manifold assembly 4803 to which may be coupled at least one final product vial 4804, a sterility vial 4805, an optional quality check station 4884, and an optional waste collection system 4806. A control system may be integrated into the system 4800 to provide automatic and/or manual control over various aspects of the radiopharmaceutical dispensing process. Although described herein as having one pump 4805 or one bulk product vial 4801, for example, the system may encompass multiple pumps feeding multiple fluid pathways for dispensing multiple different products without cross contamination. The potential exposure of technicians may be further reduced, as the necessity to enter the shielded environment in order to change out disposable components of the system 4800 between batches (radiation safety hazard) may be further reduced.

As shown in FIG. 48, the peristaltic pump 4805 may be a simple mechanical pump comprising a replaceable tube element and rollers 4826, for example. The rollers 4826 are conventionally provided at intervals along a radial track and rotate about a central axis to exert localized pressure on the tube element 4810, which in turn pushes a fluid through the tube element 4810 and creates a negative pressure at an inlet of the tube element 4810 for drawing additional fluid into the tube element 4810. Control of the fluid flow may be by way of a standard motor (not shown) coupled to the peristaltic pump 4805. However, as shown in FIG. 48, by attaching a stepper motor 4856, for example, to the peristaltic pump 4805, aspects of the present invention permit a much more refined degree of control over the fluid flow parameters through the tube element 4810. For example, by calibrating the rotation of the pump 4805 in accordance with the rotation of the stepper motor 4856, as determined by a number of pulses applied by the stepper motor 4856 over a given period of time, a control algorithm may be determined to accurately predict and control the amount of fluid being pushed through the tube element 4810 as a function of the number of pulses of the stepper motor 4856.

In accordance with another aspect of the invention, the control system may be used to store calibration data for each position of a final product vial 4804 along the dispensing manifold assembly 4803, permitting very precise control of the fluid flow parameters into each final product vial 4804 without the need for individual flow meters for each final product vial 4804. Although referred to herein as a final product vial 4804, the final product vial 4804 may be any suitable vessel for receiving a quantity of the radiopharmaceutical product, including a sterility vial, final product vial, or a quality control syringe, for example.

According to another aspect of the present invention, the stepper motor 4856 may be used to operate the peristaltic pump 4805 in reverse. As such, the closed path vial fill system 4800 may be used to draw a diluting solution, such as a sterile saline solution, from a dilution container 4866, for diluting the bulk radionuclide product in the bulk product vial 4801. The dilution container 4866 may be a flexible, sterile bag comprised of a resilient PVC material, for example. As shown in FIG. 48, the dilution container 4866 may be integrated into the system 4800, preferably between the peristaltic pump 4805 and the dispensing manifold assembly 4803, by way of a valve 4865. The valve 4865 may be a three-port solenoid valve, a diverter valve, or a stopcock valve, for example, and provides closed fluid communication between the peristaltic pump 4805 and the dispensing manifold assembly 4803 when selectively actuated to a first position, and closed fluid communication between the dilution container 4866 and the peristaltic pump 4805 when selectively actuated to a second position.

Figure 49:
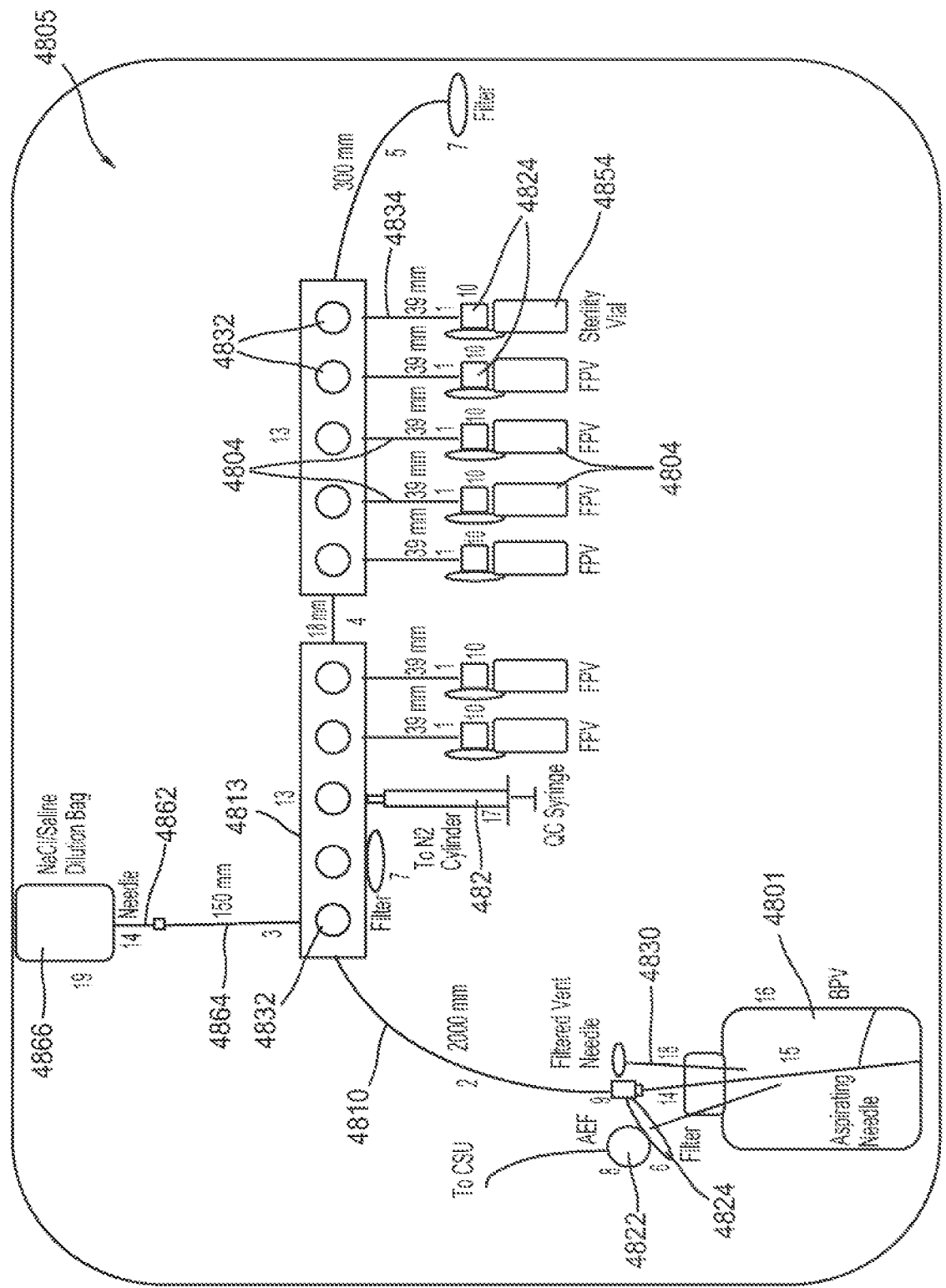

As shown in FIG. 49, a sterile kit 4805 may be provided for each new compounding run of a radiopharmaceutical that includes one or more of the bulk product vial 4801, the dilution container 4866, pre-filled with the dilution solution, the filter 4870, the manifold tubes 4813 and valves 4823, and the final product vials 4804, including the vented fill caps 4824. The kit 500 may come with certain or all of the components preassembled to allow for efficient set up of the system 4800.

The kit 4805 may be aseptically assembled inside a laminar flow hood inside a clean room prior to packaging for delivery and use. The kit components may be sterilized through a gamma radiation sterilization technique, or where the final product vials 4804 may be susceptible to damage from the gamma radiation, for example, steam sterilization techniques may be used. Accordingly, the kit components may arrive sterilized with some of the components already connected. The dilution container 4866, sterility vial 4854, final product vials 4854, and vented fill caps 4824 for each sterility vial 4854 and final product vial 4804 may require cleaning. Although the inside and/or contents of each of the components may be sterile, the outside surfaces and, in particular, the septa, or resealable membranes of the vials, may be sterilized with alcohol wipes prior to use in the kit. For example, the vented fill cap 4824 packages may be opened in the laminar flow hood, however, the packages should be soaked in hydrogen peroxide or alcohol prior to placement in the laminar flow hood. The vented fill caps 4824 in the packages are sterile and therefore do not require additional sterilization upon being released from the packages when in the laminar flow hood.

As shown in FIG. 49, once sterilized in the hood, the dilution container 4866 and vials 4804/4854 may be connected to the other sterile kit components. The dilution container 4866 may be connected by inserting a needle 4862 through the dilution container's septum. A dilution tube 4864 may be connected to a distal end of the needle 4862 and connected to the manifold tube 4813 through a valve. According to another aspect of the invention, the dilution tube 4864 may be configured to connect directly to one of the dispensing ports 4832, as shown with regard to the first port in FIG. 49. Vented fill caps 4824 may be mounted to the dispensing ports 4832 directly, or by way of the connector tubes 4834, for example, according to the number of final product vials 4804 desired and/or to accommodate the sterility vial 4854. The final product vials 4804 and the sterility vial 4854 may then be connected to the corresponding vial caps 4824, as appropriate. In this manner, it may be preferable to connect the sterility vial 4854 to the dispensing port 4832 sequentially farthest from the pump 4805 as compared to the final product vials 4804. In addition, if a mixture of vial sizes is being used in the system 4800, larger final product vials 4804 may be arranged to connect to dispensing ports 4832 along with the smaller final product vials 4804 in any desired sequence with respect to the pump 4805.

Figure 50:
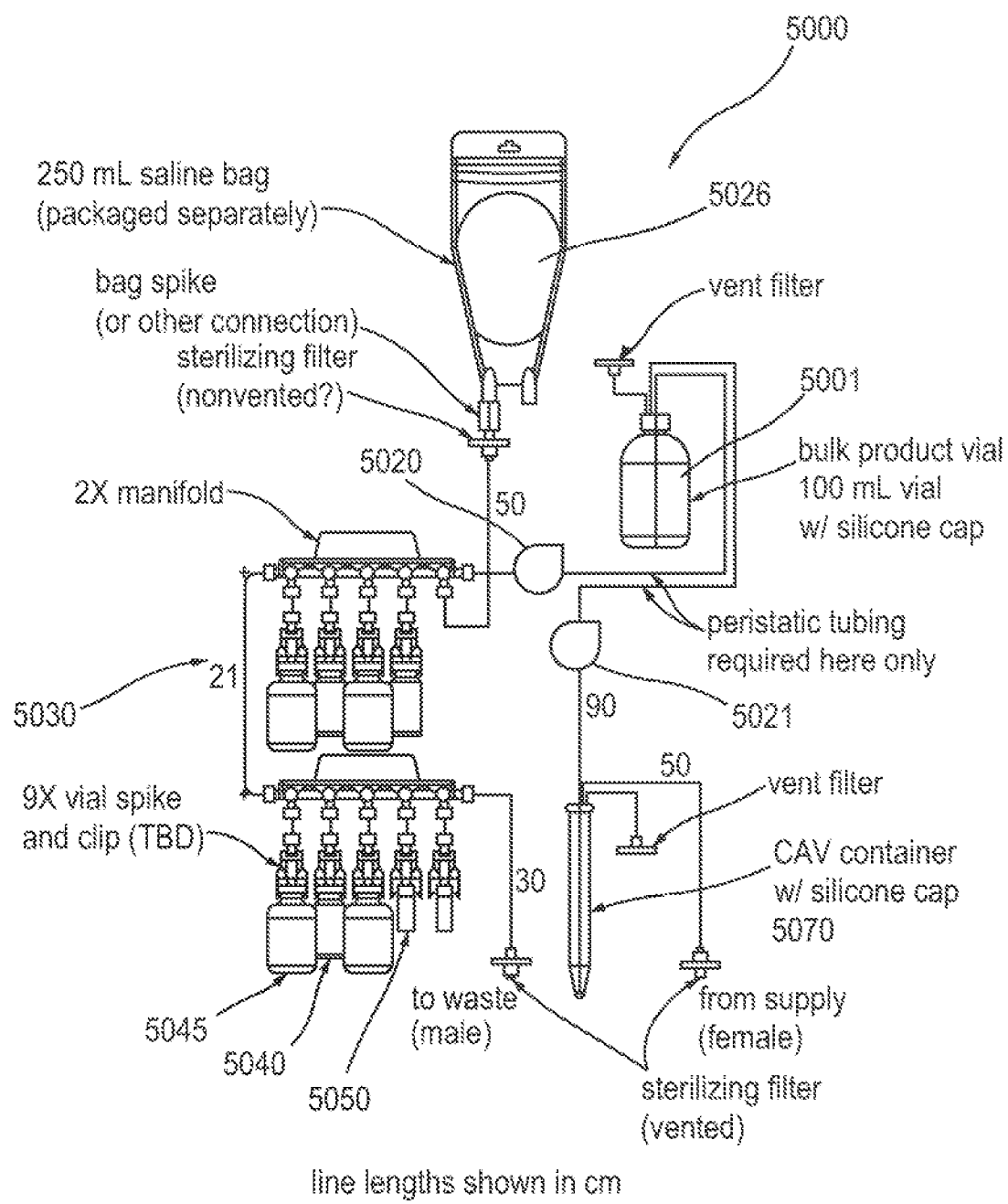

FIG. 50 is a schematic to further illustrate a closed vial fill system 5000 incorporating a CAV sensor 5070. The radiopharmaceutical product 5001 may be delivered from the synthesizing unit directly to the CAV container. The CAV sensor 5070 records the concentration, activity, and/or volume components of the radiopharmaceutical product 5001. Once the desired parameters have been measured by the CAV sensor 5070, the peristaltic pump 5021 may be used to draw the entire volume of the radiopharmaceutical product 5001 from the CAV container 5070 for deposit into the bulk product vial 5001. As described above in detail, the peristaltic pump 5020 may then be used to draw a dilution solution from the dilution container 5026 to dilute the radiopharmaceutical product 5001 to desired levels of concentration and activity in accordance with the measurements recorded by the CAV sensor 5070. The diluted product may then be used to fill the final product vials 5040, 5045, the sterility vial 5050, and/or the quality check syringes, for example, as pre-programmed in the control system.

Additional details of the vial filler may be found in U.S. Provisional Application No. 61/508,409 entitled "Closed Vial Fill System for Aseptic Dispensing," filed on Jul. 15, 2011, U.S. application Ser. No. 13/339,226, titled "Closed Vial Fill System for Aseptic Dispensing," filed on Dec. 28, 2011, and PCT Application No. PCT/US2011/067650, titled "Closed Vial Fill System for Aseptic Dispensing," filed on Dec. 28, 2011, the entire contents of each of which are hereby incorporated by reference herein.

Safety Features

Safety features may comprise any of automated Interlocks and Emergency Shutdown, operator alarms, fail safe operation, user privileges, and set point limits.

Automated interlocks may be used to initiate and perform automatic emergency shutdowns when safe operating parameters are exceeded. They may be also used to prevent processes or equipment from being started out of sequence with respect to other equipment in a manner that would present a safety hazard or to prevent designated processes or equipment from being started if other equipment, critical to the safety of the process, is nonfunctional.

Operator alarm conditions may comprise events or parameters that are predetermined to require operator attention or response. Examples of alarm conditions are a process variable being out of the desired or safe operating range, equipment such as a pump or other device failing to run when commanded, or an alarm signal from an outside source, such as a facility fire alarm or an alarm signal from an independent controller. Alarms must be date and time stamped and logged. Alarm logs are a trouble shooting and diagnostic tool that record the sequence of alarm events and can be used to help determine the root cause(s) of the alarm condition. Alarms may be categorized for severity and presented to the operator in a different manner according to the severity of the condition.

Fail Safe Operation of process control equipment may comprise self diagnostics and the ability of the control system to respond to faults by going into predefined fault states is an important safety feature.

User privilege levels are used to restrict access to process control operations to approved users, which helps to insure that only qualified and authorized users have access to functions that can compromise the safety of the system. User privilege levels are typically set by the system administrator and controlled through a user log-on function. For example, user levels such as Guest, Operator, Supervisor, and Administrator may be used with increasing levels of access for each level.

Set point limits may be used to limit the allowable range of set points that may be entered by an operator to values that will not compromise the safe operation of the system.

The control system architecture should also have the flexibility to accommodate any expected performance requirements. A general consideration for any process control system is that the system provides robust, reliable, and predictable operation. Industry standards for similar applications and the choice between using commercial off-the-shelf (COTS) hardware or custom hardware are considered. The physical size, location, electromagnetic compatibility, radiation shielding, and other special requirements must be compatible with the restraints of the process and installation. The system architecture should have the ability to accommodate the development process by providing control and support for development and testing of subsystems up to full system prototypes as well as the final production system.

The control system must have the ability for high speed timing and control in the order of several milliseconds. Critical communication paths must be deterministic and repeatable to provide real-time control for time-critical I/O and messaging data. This may be provided in part by the systems described herein and the system illustrated in FIGS. 50 and 51.

Data acquisition and logging, data export capability, and graphical trending of both historical and real-time data may be provided. Secure data logging may be required for regulatory purposes, therefore methods of data acquisition and storage must be compliant with pharmaceutical manufacturing requirements.

Control Software and Subsystem(s)

Aspects are directed to systems, methods, and devices for providing software and hardware controls for overall and various sub-portion operation that include suitable radiation and other damage and contamination resistant features, and that allow for optional remote data collection, communication, and/or control for producing radiopharmaceuticals. Aspects of the process for producing pharmaceuticals include: 1) generating radionuclides for use in production of radiopharmaceuticals, such as via use of a cyclotron; 2) synthesizing the radionuclides generated and removing any unwanted products included with the generated radionuclides (e.g., drying and/or deprotecting the generated radionuclides); 3) measuring the quantity and activity level of the synthesized radionuclides; 4) distributively delivering the radionuclides in appropriate quantities to a plurality of modular cassette synthesis units in a modular cassette subsystem for contemporaneous/parallel production of radiopharmaceutical output and that allow reuse and/or quick, safe, and disposable replacement of portions of the subsystem; 5) delivering appropriate quantities of non-radionuclide components to the plurality of modular cassette synthesis units as part of the contemporaneous/parallel production of radiopharmaceutical output; 6) upon production of the radiopharmaceutical output from the plurality of modular cassette synthesis units, measuring the quantity and activity level of each stream of radiopharmaceutical output; 7) purifying the radiopharmaceutical output; 8) distributively dispensing individual doses in one or more sterile vials; 9) optionally automatically producing labeling and dose related information for use with the doses; and 10) performing automated quality control on one or more extracted samples from the produced radiopharmaceutical output.

Individual systems typically used during production of radiopharmaceuticals operate on various independent software systems without interacting with other software systems involved in the production of radiopharmaceuticals. Thus, there is a need in the art for methods and systems for coordinating the production of radiopharmaceuticals to ensure that a radiopharmaceutical is produced efficiently and delivered to a patient before the radiopharmaceutical decays. Moreover, there is a need in the art for automating the production process of radiopharmaceuticals in order to reduce the time required for production, the amount of training required for operators of the production system, the amount of operator error and/or the number of failed batches during the production process, in addition to producing a high-quality product and performing efficient quality control contemporaneously with or subsequently to the production of radiopharmaceuticals.

Figure 51:
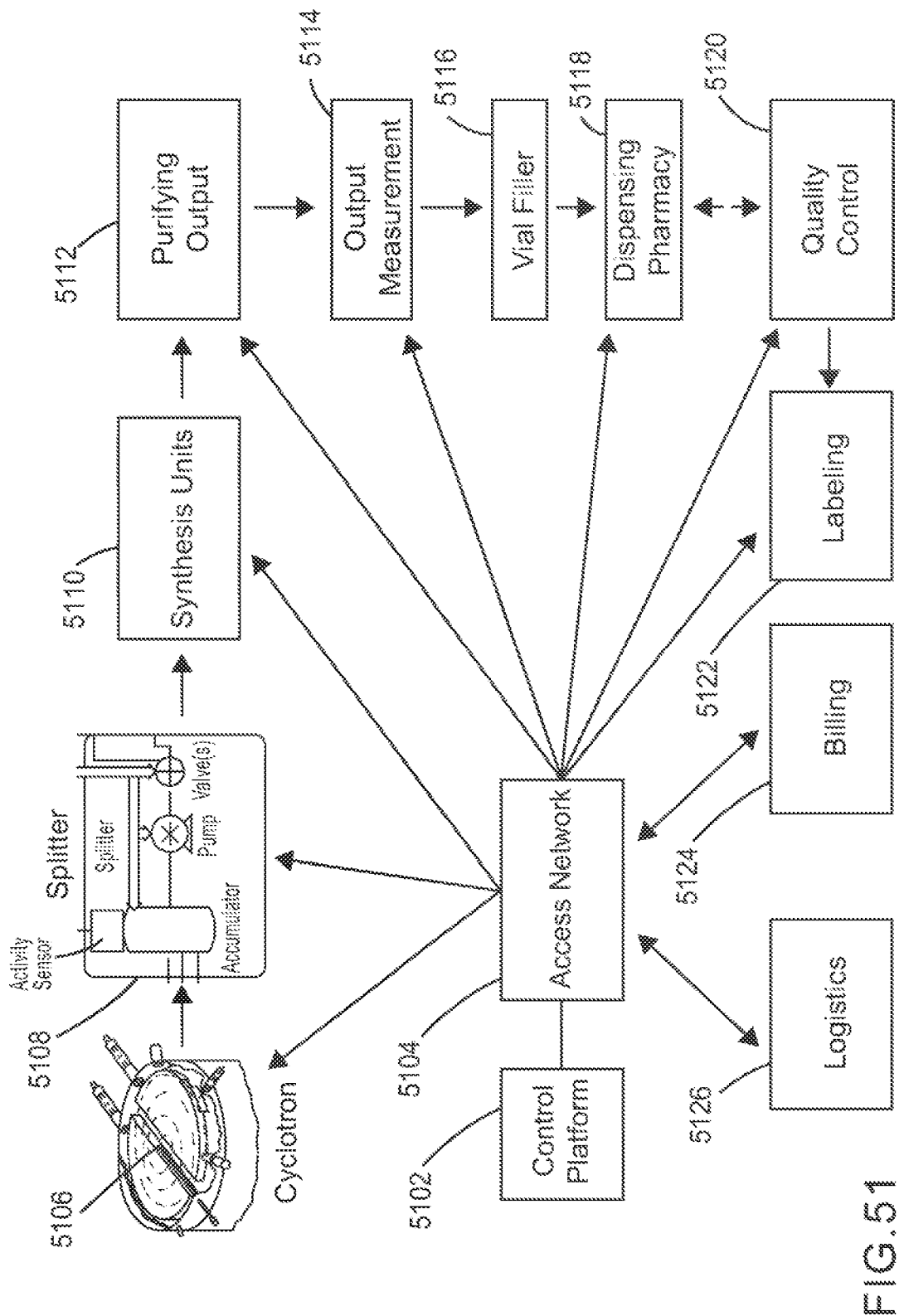
FIG. 51 presents a representative diagram of various portions of an example system in accordance with aspects presented herein.

FIG. 51 illustrates a system similar to FIG. 1. Cooperation between system components in FIG. 51 allows increased production by providing increased efficiency of feed and accuracy of both characteristics and volume of radionuclide raw material input to the production process. It should be appreciated that any of the systems 5106-5126, may comprise wired, wireless, and/or fiber optically communicating devices and/or other computing devices. Wireless devices, for example, may include any suitable mobile, portable computing or communications device, such as a cellular device, that may connect to an access network 5104. For example, wireless devices may include a cellular telephone, a navigation system, a global positioning system (GPS), a computing device, a camera, a personal digital assistant (PDA), or other handheld device having wireless connection capability, among other devices. It should also be appreciated that control platform 5102 may comprise a server and/or computing devices that may include, for example, any suitable mobile or fixed computing device connected to a network.

Control platform 5102 may use the input received from one or more systems, such as cyclotron system 5106, splitter system 5108, synthesis units system 5110, purifying output system 5112, output measurement system 5114, vial filler system 5116, pharmacy dispensing and distribution system 5118, quality control system 5120, labeling system 5122, billing system 5124, and/or logistic system 5126 to create an environment for controlling and/or managing the production and distribution of radiopharmaceuticals.

In an aspect, control platform 5102 may be used to communicate between the one or more systems 5106-5126. For example, control platform 5102 may notify the various systems 5106-5126 when a particular system should be used in the process of manufacturing and/or delivering radiopharmaceuticals. Thus, control platform 5102 may be used to coordinate the sequence and timing of production of radiopharmaceuticals. For example, control platform 5102 may receive input from cyclotron system 5106 indicating that the cyclotron system 5106 is finished producing radioactive output, such as, but not limited to, Fluorine 18, C11, NH3. The received input from cyclotron system 5106 may include, but is not limited to, the following information relating to the production of the radioactive output: an amount of output produced; a start time for the production; an end time for the production; a total production time (e.g., a total amount of time cyclotron system 5106 spent producing the output); an order receipt time; and/or a location of the cyclotron system 5106 (e.g., the location of the lab where the cyclotron system 5106 is housed), among other information relating to the production of radioactive output.

Control platform 5102 may process the received information from cyclotron system 106 and notify splitter system 5108 that the radionuclide, e.g., F-18 is ready to be delivered into the splitter. In addition, control platform 5102 may be used to distribute the radioactive output produced by cyclotron system 5106 to splitter system 5108 for use in the next step of processing the radiopharmaceuticals. It should be appreciated that similar information, as discussed above, may be received from the one or more systems 5106-5126. It should be appreciated that control platform 5102 may be involved in each stage of the production and/or distribution process of radiopharmaceuticals, and may be used to coordinate the sequence of production of the radiopharmaceuticals. Control platform 5102 may be able to track the progress of the radiopharmaceutical product, as the product moves through the various systems 5106-5126 and use the information received from the one or more systems 5106-5126 to notify the various systems 106-126 when a particular system should be used. By communication with the various systems 5106-5126, control platform 5102 may increase the efficiency of production of radiopharmaceuticals. Control platform 5102 may also be used to communicate with a remote monitoring station which may be able to further support production of radiopharmaceuticals (e.g., mission control) and/or maintenance of the production system.

In an aspect, control platform 5102 may be used to increase the number of simultaneous product synthesis being performed by synthesis unit 5110 in multiple modules of a multisynthesis unit based upon, for example, need, volume and/or activity. For example, control platform 5102 may direct synthesis unit 5110 to perform parallel synthesis of one or more different radiopharmaceuticals simultaneously. Control platform 5102 may be used for example, to direct the amount of radioactive output, such as F-18, C11 or NH3 produced by cyclotron 5106 and distribute via the splitter 5108 the radioactive output based upon the amount of activity needed to produce the one or more products. For example, control platform 5102 may direct the correct amount of F-18, C11 or NH3 from splitter 5108 to one or more synthesis units 5110 to perform the requested synthesis.

It should be appreciated that a number of syntheses may be capable of occurring at the same time and being controlled by control platform 5102. In an aspect, up to 12 syntheses may be performed by synthesis unit 5110 in 2 multisynthesis units. In another aspect, control platform 5102 may control more than one synthesis unit 5110, with each synthesis unit 5110 running parallel synthesis to produce one or more different radiopharmaceuticals.

In an aspect, control platform 5102 may interface with vial filler 5116 to ensure that the produced radiopharmaceuticals are filled in the correct quantities amongst several bulk product vials to be distributed to pharmacies. For example, control platform 5102 may ensure that a correct quantity of a radiopharmaceutical is distributed to the correct pharmacy at the correct time.

In addition, control platform 5102 may monitor and/or control the quantity of bulk product to pharmacies by receiving and/or providing information to vial filler 5116. In an aspect, control platform 5102 may communicate with the pharmacy 5118 and monitor the individual patient dose drawn at the pharmacy. For example, the shielding of the device delivering the radiopharmaceutical to the patient may have a sensor embedded in the housing that may provide patient dosage information to the pharmacy dispensing distribution system 5118. Patient dosage information may include, but is not limited to, the amount of radiopharmaceutical being injected into the patient, the remaining radiopharmaceutical in the housing after providing the dosage to the patient, and the weight of the housing after providing the dosage to the patient, among other patient dosage information. Control system 5102 may receive the patient dosage information provided by pharmacy dispensing distribution system 5118 and compare the received patient dosage information with the amount of radiopharmaceutical originally delivered to the patient and determine the amount of radiopharmaceutical remaining in the housing after providing the patient dosage. Control system 5102 may use the patient dosage information to determine whether a proper amount of radiopharmaceutical was delivered to the patient.

In addition, control platform 5102 may use the input received from the one or more systems 5106-5126 to track radiopharmaceuticals from the production stage to the patient dosage. In an aspect, a batch record number may be linked to the one or more radiopharmaceuticals produced via system 5100 and stored in a data store on control platform 5102. For example, the batch record number may be linked to and/or associated with a specific dose for a particular patient from a batch of radiopharmaceutical produced. Thus, control platform 5102 may be able to use the batch record number associated with the specific dose provided to the patient to trace the radiopharmaceutical to the original source of the radiopharmaceutical, e.g., the materials used for production and/or the location where the radiopharmaceutical was produced. In an aspect, the batch record number may be included on a hardware device delivering the radiopharmaceutical to the patient. For example, the batch record number may be a chip, such as radio-frequency identification (RFID) chip, embedded on the hardware device. In addition, the batch record number may be printed on the shield of the device delivering the radiopharmaceutical to the patient.

In one variation, the input received from the one or more systems 5106-5126 during the production and/or delivery of radiopharmaceuticals may be used by control platform 5102 to trace the location and/or source of the materials used during production of radiopharmaceuticals. For example, if a patient receives a radiopharmaceutical and experiences an adverse reaction to it, the control platform 5102 may be used to aid a pharmacy in determining whether an error occurred during the production of the radiopharmaceutical. Control platform 5102 may receive input regarding the particular radiopharmaceutical supplied to the patient, e.g., a batch record number of the radiopharmaceutical, and may use the input received from the one or more systems 5106-5126 during the production of the radiopharmaceutical to determine, for example, production factors relating to the radiopharmaceutical supplied to the patient. Production factors may include, but are not limited to, a location where the particular radiopharmaceutical was produced, materials used during the production process, a time when the radiopharmaceutical was produced, and/or an amount of time the radiopharmaceutical spent in transit, among other production factors. It should be appreciated that the control platform 5102 may generate the production factors in real-time or near real-time, and therefore, provide the received information for the particular radiopharmaceutical to the pharmacy, and thus, to the provider quickly to aid in determining the cause of a patient's adverse reaction to the particular radiopharmaceutical.

Control platform 5102 may further use the input received from one or more systems 5106-5102 for performing quality control measures during the production of radiopharmaceuticals. Quality control measures may include, but are not limited to, checking and/or testing the status of each of the systems 5106-5126, checking the environment surrounding systems 5106-5126, testing outputs produced by each of the systems 5106-5126, and/or performing testing on samples of the radiopharmaceuticals produced by system 5100, among other quality control measures. In an aspect, a regulatory agency, such as the Food and Drug Administration (FDA) regulates the production of radiopharmaceuticals and requires a quality threshold be met during the production. Quality control system 5120 may be used, for example, to generate one or more quality reports relating to the quality of the radiopharmaceuticals produced by system 5100. Quality reports may include, but are not limited to: analytical tests performed on the product; total yield of the products; failure reports for the product; failure reports for the one or more systems used to manufacture the product; and/or operator error reports, among other quality reports. Quality control system 5120 may interface with each individual system when performing the quality control measures.

In an aspect, control platform 5102 may generate alerts indicating a failure in the process and/or a delay in the process. For example, alerts may be generated when one or more of the systems 5106-5126 malfunctions and/or stop working. Alerts may be used by control platform 5102 to stop the manufacturing process and/or redirect the workflow of the manufacturing process. For example, if the control platform receives an alert that a cyclotron in a lab is malfunctioning, the control platform may direct new radiopharmaceuticals orders to cyclotrons in other labs until the control platform receives an update clearing the alert. By having the capability to redirect the workflow upon receiving alerts indicating a problem during production, the control platform may be able to maximize the use of available resources and maintain production of the radiopharmaceuticals within a required time frame. Thus, the control platform may be able to get the radiopharmaceutical to the patients within a timely manner and maximize the effectiveness of the radiopharmaceutical received by the patients.

In another example, alerts may be generated if an environment surrounding the one or more systems 5106-5126 becomes unstable. For example, the environment surrounding the one or more systems 5106-5126 may be required to remain within a temperature range to ensure the safety of the equipment and/or the individuals involved in the production process. If control platform 5102 detects that the temperature of the environment exceeds the desired temperature range, control platform 5102 may generate an alert indicating the temperature of the environment exceeded the temperature range and stop the production process and/or alter the temperature controls in the environment. In addition, control platform may be able to redirect the workflow of the production, as discussed above upon receiving the alert.

In one aspect, control platform 5102 may receive input from logistics system 5126 to ensure that the production and distribution of radiopharmaceutical may be ordered, manufactured, and distributed to a patient within a required time period (e.g., 24 hours). Logistics system 5126 may store information relating to the production capabilities factors of one or more production sites (e.g., a lab where the radiopharmaceuticals are produced). Production capabilities factors may include, but are not limited to, the amount of available materials at the production site, the workloads of the system components at the production sites, and/or available system components at the production sites, among other production capabilities factors.

Control platform 5102 may manage the workload of the systems 5106-5126 by adding and/or removing processes from the one or more systems 5106-5126 based upon, for example, available resources at a particular production facility and/or pharmacy. In an aspect, control platform 5102 may receive a request for a quantity of a particular radiopharmaceutical, and may place an order with an available cyclotron 5106 and location which has the proper materials to produce the requested radiopharmaceutical. In addition, control platform 5102 may distribute workloads for the one or more systems 5106-5126 and/or redistribute the workloads to maximize, for example, the available materials at the one or more systems 5106-5126. For example, if splitter 5108 has enough materials for the received request, control platform 5102 may redirect which synthesis unit 5110 the materials are directed to from splitter 5108 based upon the received request. In addition, if another production site has more available resources, the control platform 5102 may move the production of the requested radiopharmaceutical to the other production site with more available resources.

Figure 52:
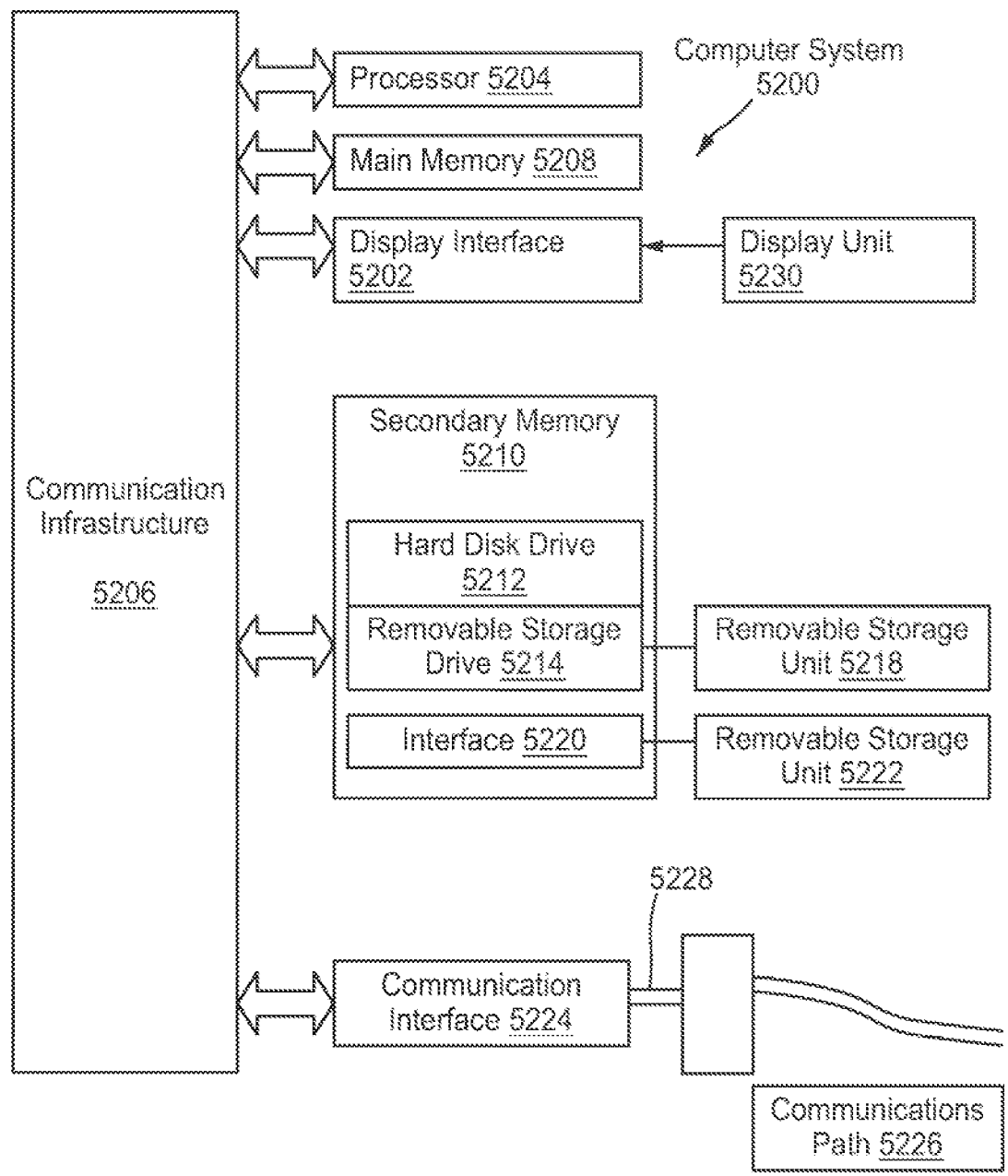
FIGS. 52 and 53 show a representative diagram of an example computer system for use in accordance with aspects of the present invention.

Aspects presented herein may be implemented using hardware, software, or a combination thereof and may be implemented in one or more computer systems or other processing systems. In an aspect, features are directed toward one or more computer systems capable of carrying out the functionality described herein. An example of such a computer system 5200 is shown in FIG. 52.

Computer system 5200 includes one or more processors, such as processor 5204. The processor 5204 is coupled to a communication infrastructure 5206 (e.g., a communications bus, cross-over bar, or network). Various software aspects are described in terms of this example computer system. After reading this description, it will become apparent to a person skilled in the relevant art(s) how to implement aspects hereof using other computer systems and/or architectures.

Computer system 5200 may include a display interface 5202 that forwards graphics, text, and other data from the communication infrastructure 5206 (or from a frame buffer not shown) for display on a display unit 5230. Computer system 5200 may include a main memory 5208, preferably random access memory (RAM), and may also include a secondary memory 5210. The secondary memory 5210 may include, for example, a hard disk drive 5212 and/or a removable storage drive 5214, representing a floppy disk drive, a magnetic tape drive, an optical disk drive, etc. The removable storage drive 5214 may read from and/or write to a removable storage unit 5218 in a well-known manner. Removable storage unit 5218, represents a floppy disk, magnetic tape, optical disk, etc., which may be read by and written to removable storage drive 5214. As will be appreciated, the removable storage unit 5218 may include a computer usable storage medium having stored therein computer software and/or data.

Alternative aspects may include secondary memory 5210 and may include other similar devices for allowing computer programs or other instructions to be loaded into computer system 5200. Such devices may include, for example, a removable storage unit 5222 and an interface 5220. Examples of such may include a program cartridge and cartridge interface (such as that found in video game devices), a removable memory chip (such as an erasable programmable read only memory (EPROM), or programmable read only memory (PROM)) and associated socket, and other removable storage units 5222 and interfaces 5220, which allow software and data to be transferred from the removable storage unit 5222 to computer system 5200.

Computer system 5200 may also include a communications interface 5224. Communications interface 5224 may allow software and data to be transferred among computer system 400 and external devices. Examples of communications interface 5224 may include a modem, a network interface (such as an Ethernet card), a communications port, a Personal Computer Memory Card International Association (PCMCIA) slot and card, etc. Software and data transferred via communications interface 5224 may be in the form of signals 5228, which may be electronic, electromagnetic, optical or other signals capable of being received by communications interface 5224. These signals 5228 may be provided to communications interface 5224 via a communications path (e.g., channel) 5226. This path 5226 may carry signals 5228 and may be implemented using wire or cable, fiber optics, a telephone line, a cellular link, a radio frequency (RF) link and/or other communications channels. As used herein, the terms "computer program medium" and "computer usable medium" refer generally to media such as a removable storage drive 480, a hard disk installed in hard disk drive 5212, and/or signals 5228. These computer program products may provide software to the computer system 5200. Aspects are directed to such computer program products.

Computer programs (also referred to as computer control logic) may be stored in main memory 5208 and/or secondary memory 5210. Computer programs may also be received via communications interface 5224. Such computer programs, when executed, may enable the computer system 5200 to perform the features in accordance with aspects presented herein, as discussed herein. In particular, the computer programs, when executed, may enable the processor 5210 to perform the features in accordance with aspects of the present invention. Accordingly, such computer programs may represent controllers of the computer system 5200.

Where aspects presented herein may be implemented using software, the software may be stored in a computer program product and loaded into computer system 5200 using removable storage drive 5214, hard drive 5212, or communications interface 5220. The control logic (software), when executed by the processor 5204, may cause the processor 5204 to perform the functions described herein. In another aspect, the system may be implemented primarily in hardware using, for example, hardware components, such as application specific integrated circuits (ASICs). Implementation of the hardware state machine so as to perform the functions described herein will be apparent to persons skilled in the relevant art(s).

Example control system architectures may comprise, among others, any of a PLC-HMI based system, a custom hardware/custom software system, and a labView based system. A PLC (Programmable Logic Controller), also referred to as a PAC (Programmable Automation Controller), such as Allen Bradley ControlLogix system provides process control, e.g., PLC software in ladder logic and function block programming languages may be used. A panel mounted or desktop PC may be used for the Human Machine Interface (HMI). The HMI software may use development software such as Wonderware InTouch or Rockwell RSView. A data historian such as Wonderware Historian or similar product may be used for data acquisition, data export, trending, and reporting. Custom embedded hardware may be used to interface field devices with process control provided by custom PC based and/or embedded software. The HMI and control software may be in C/C++/C# programming languages. National Instruments LabView CompactRIO hardware may be used for process control. A panel mounted or desktop PC may be used for the HMI. Both the control and HMI software may use LabView Developer Suite Core development software. The software may be written in LabView's custom graphical programming language.

In yet another variation, aspects presented herein may be implemented using a combination of both hardware and software.

Figure 53:
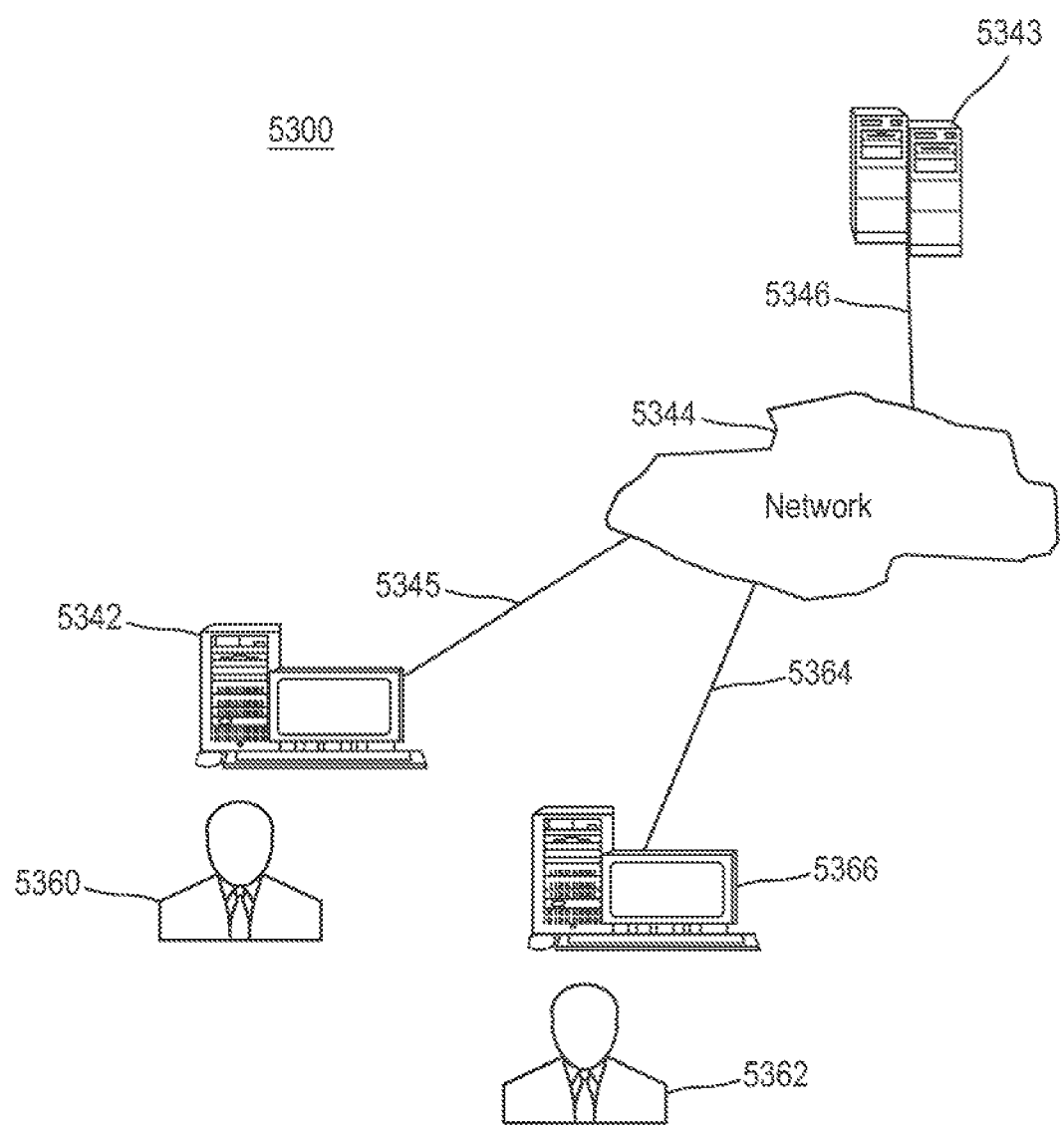

FIG. 53 shows a communication system 5300 usable in accordance with aspects of the present invention. The communication system 5300 includes one or more accessors 5360, 5362 (also referred to interchangeably herein as one or more "users") and one or more terminals 5342, 5366. In one aspect of the present invention, data for use is, for example, input and/or accessed by accessors 5360, 5364 via terminals 5342, 5366, such as personal computers (PCs), minicomputers, mainframe computers, microcomputers, telephonic devices, or wireless devices, such as personal digital assistants ("PDAs") or a hand-held wireless devices coupled to a server 5343, such as a PC, minicomputer, mainframe computer, microcomputer, or other device having a processor and a repository for data and/or connection to a repository for data, via, for example, a network 5344, such as the Internet or an intranet, and couplings 5345, 5346, 5364. The couplings 5345, 5346, and 5364 include, for example, wired, wireless, or fiberoptic links. In another aspect of the present invention, the method and system of the present invention operate in a stand-alone environment, such as on a single terminal.

Example aspects have now been described in accordance with the above advantages. It will be appreciated that these examples are merely illustrative hereof. Many variations and modifications will be apparent to those skilled in the art.

What is claimed is:

1. A radiopharmaceutical production system comprising:
   a cyclotron;
   a synthesis unit operatively connected to the cyclotron and to a reagent pack, the synthesis unit comprising at least one modular, disposable cassette unit for receiving a radionuclide from the cyclotron and one or more pharmaceutical reagents from the reagent pack;
   a vial filler operatively connected to the synthesis unit for dispensing a radiopharmaceutical produced by the synthesis unit into a vial;
   a quality control unit operatively connected to the synthesis unit for performing automated quality control on a sample of at least one dose of the radiopharmaceutical; and
   a control platform operatively connected to at least one of the synthesis unit and the quality control unit for receiving therefrom and for associating a unique identifier with each dose of the radiopharmaceutical synthesized by the system.

2. The radiopharmaceutical production system according to claim 1, further comprising a purifying component to purify the at least one dose of the radiopharmaceutical prior to the at least one dose of the radiopharmaceutical being received in the vial.

3. The radiopharmaceutical production system according to claim 2, wherein the purifying component comprises a solid phase extraction component.

4. The radiopharmaceutical production system according to claim 2, wherein the purifying component comprises an HPLC component.

5. The radiopharmaceutical production system according to claim 2, wherein at least a portion of the purifying component is disposable.

6. The radiopharmaceutical production system according to claim 1, further comprising at least one reagent pack, wherein the at least one reagent pack is attachable to the synthesis unit.

7. The radiopharmaceutical production system according to claim 6, wherein the at least one reagent pack is disposable.

8. The radiopharmaceutical production system according to claim 6, wherein the at least one reagent pack is detachable from the at least one cassette unit.

9. The radiopharmaceutical production system according to claim 6, wherein the at least one reagent pack is receivable for one or more disposable reagent capsules.

10. The radiopharmaceutical production system according to claim 1, wherein the radionuclide comprises F-18.

11. The radiopharmaceutical production system according to claim 1, comprising at least two modular, disposable cassette units.

12. The radiopharmaceutical production system according to claim 11, further comprising a splitter operatively connected to the cyclotron for routing the radionuclide to each of the at least two cassette units.

13. The radiopharmaceutical production system according to claim 12, wherein the splitter comprises a pump to dispose a predetermined amount of the radionuclide to each of the at least two cassette units.

14. The radiopharmaceutical production system according to claim 1, further comprising a check valve to deliver a metered amount of a fluid containing O-18 atoms to a target cell irradiated by a proton beam, wherein the proton beam converts the O-18 to F-18.

15. The radiopharmaceutical production system according to claim 1, further comprising a communication connection to a dispensing pharmacy.

16. The radiopharmaceutical production system according to claim 1, wherein the vial filler comprises a sensor to measure at least one of an activity level and a volume of the at least one dose of the radiopharmaceutical received in the vial.

17. The radiopharmaceutical production system according to claim 16, wherein the sensor comprises a cadmium zinc telluride element.

18. The radiopharmaceutical production system according to claim 1, comprising six modular, disposable cassette units.

19. The radiopharmaceutical production system according to claim 1, wherein the at least one cassette unit comprises a reaction vessel and at least one of a quaternary methylammonium cartridge, heating provisions, a mixing chamber, a neutralizing chamber, a final production collection chamber, and a solid phase exchange cartridge.

20. The radiopharmaceutical production system according to claim 1, wherein the quality control unit is operatively connected to the synthesis unit to assess the sample of the at least one dose of the radiopharmaceutical for particle and color content, filter membrane integrity, pH value, residual solvent volume, Kryptofix concentration, bacterial endotoxins concentration, radionuclidic identify, radionuclidic purity, radiochemical identity, radiochemical purity, sterility, or a combination thereof.

* * * * *